United States Patent
Bredlau et al.

(10) Patent No.: US 12,350,318 B2
(45) Date of Patent: Jul. 8, 2025

(54) COMBINATION THERAPY TO TREAT BRAIN CANCER

(71) Applicants: Inovio Pharmaceuticals, Inc., Plymouth Meeting, PA (US); Regeneron Pharmaceuticals, Inc., Tarrytown, NY (US)

(72) Inventors: Amy-Lee Bredlau, Mahopac, NY (US); Israel Lowy, Dobbs Ferry, NY (US); Jeffrey Skolnik, Cherry Hill, NJ (US); Jian Yan, Wallingford, PA (US); Bernadette Ferraro, San Diego, CA (US); Jewell Walters, Poway, CA (US); Albert J. Sylvester, III, Croydon, PA (US); Kimberly A. Kraynyak, Norristown, PA (US); Matthew P. Morrow, Malvern, PA (US); Elisabeth Gillespie, Horsham, PA (US)

(73) Assignees: Inovio Pharmaceuticals, Inc., Plymouth Meeting, PA (US); Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 17/819,401

(22) Filed: Aug. 12, 2022

(65) Prior Publication Data
US 2023/0070723 A1 Mar. 9, 2023

Related U.S. Application Data
(60) Provisional application No. 63/232,966, filed on Aug. 13, 2021.

(51) Int. Cl.
| | |
|---|---|
| A61K 38/20 | (2006.01) |
| A61K 31/495 | (2006.01) |
| A61K 39/00 | (2006.01) |
| A61K 39/395 | (2006.01) |
| A61K 41/00 | (2020.01) |
| A61N 5/10 | (2006.01) |
| A61P 35/00 | (2006.01) |

(Continued)

(52) U.S. Cl.
CPC .......... *A61K 38/208* (2013.01); *A61K 31/495* (2013.01); *A61K 39/001153* (2018.08); *A61K 39/001157* (2018.08); *A61K 39/001195* (2018.08); *A61K 39/3955* (2013.01); *A61K 41/0047* (2013.01); *A61P 35/00* (2018.01); *C12Q 1/6886* (2013.01); *A61N 5/10* (2013.01); *C12Q 1/6869* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS
| | | |
|---|---|---|
| 3,805,783 A | 4/1974 | Ismach |
| 4,342,310 A | 8/1982 | Lindmayer et al. |
| 4,447,223 A | 5/1984 | Kaye et al. |

(Continued)

FOREIGN PATENT DOCUMENTS
| | | |
|---|---|---|
| CN | 105874061 A | 8/2016 |
| CN | 108884164 A | 11/2018 |

(Continued)

OTHER PUBLICATIONS

Clinical trial NCT03491683 (INO-5401 and INO-9012 Delivered by Electroporation (EP) in Combination With Cemiplimab (REGN2810) in Newly-Diagnosed Glioblastoma (GBM) [online] U.S. National Library of Medicine <URL https://clinicaltrials.gov/study/NCT03491683?tab=history&a=11 version Mar. 28, 2019 (Year: 2019).*

(Continued)

*Primary Examiner* — Amy E Juedes
*Assistant Examiner* — Peter Johansen
(74) *Attorney, Agent, or Firm* — BakerHostetler

(57) ABSTRACT

Provided herein are methods of treating brain cancer in a subject, comprising evaluating one or more biological samples from a subject who has brain cancer for the presence of a miRNAs and administering interleukin-12 (IL-12); an immunogenic composition of human telomerase reverse transcriptase (hTERT), Wilms Tumor-1 (WT-1), and prostate specific membrane antigen (PSMA); and an anti-programmed cell death receptor 1 (PD-1) antibody to said subject if the subject has an increased expression level of the miR-331-3p miRNA or isomiRs thereof and the miR-1537-3p miRNA or isomiRs thereof relative to a control population of subjects. Also provided herein are methods of treating brain cancer in a subject, comprising measuring an expression level of at least one mRNA biomarker selected from SYNGR3, OTX1, GABBR2, LHX1, CADM3, MLLT11, MNX1, GRB14, SLC34A2, PHYHIP, WNT10B, SLC17A6, CRLF1, HOXD13, TGFβR3, UBA7, SFRP4, or any combination thereof, in a tumor sample from a subject and administering IL-12; an immunogenic composition hTERT, WT-1, and PSMA; and an anti-PD-1 antibody to said subject if the expression level of SYNGR3, OTX1, GABBR2, LHX1, CADM3, MLLT11, MNX1, GRB14, SLC34A2, PHYHIP, WNT10B, SLC17A6, CRLF1 and HOXD13 is decreased or if the expression level of TGFβR3, UBA7, SFRP4 is increased.

23 Claims, 28 Drawing Sheets

Specification includes a Sequence Listing.

(51) Int. Cl.
  *C12Q 1/6869*   (2018.01)
  *C12Q 1/6886*   (2018.01)

(56) References Cited

U.S. PATENT DOCUMENTS

| | | | |
|---|---|---|---|
| 5,505,697 | A | 4/1996 | McKinnon et al. |
| 5,580,859 | A | 12/1996 | Felgner et al. |
| 5,676,646 | A | 10/1997 | Hofmann et al. |
| 5,679,647 | A | 10/1997 | Carson et al. |
| 5,702,359 | A | 12/1997 | Hofmann et al. |
| 5,703,055 | A | 12/1997 | Felgner et al. |
| 6,009,347 | A | 12/1999 | Hofmann |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,302,874 | B1 | 10/2001 | Zhang et al. |
| 6,520,950 | B1 | 2/2003 | Hofmann et al. |
| 6,763,264 | B2 | 7/2004 | Hofmann |
| 7,171,264 | B1 | 1/2007 | Hofmann et al. |
| 7,245,963 | B2 | 7/2007 | Draghia-Akli et al. |
| 7,328,064 | B2 | 2/2008 | Mathiesen et al. |
| 7,664,545 | B2 | 2/2010 | Westersten et al. |
| 2004/0175727 | A1 | 9/2004 | Draghia-Akli et al. |
| 2008/0234655 | A1 | 9/2008 | Mathiesen et al. |
| 2009/0137005 | A1* | 5/2009 | Felber ............... C07K 14/5434 435/325 |
| 2009/0326051 | A1 | 12/2009 | Corey et al. |
| 2015/0203579 | A1 | 7/2015 | Papadopoulos et al. |
| 2015/0328298 | A1 | 11/2015 | Weiner et al. |
| 2018/0185668 | A1 | 7/2018 | Papadopoulos et al. |
| 2019/0048085 | A1 | 2/2019 | Dotti et al. |
| 2019/0216868 | A1 | 7/2019 | Alkayyal et al. |
| 2019/0256924 | A1 | 8/2019 | Vogelstein et al. |
| 2021/0128710 | A1 | 5/2021 | Bredlau et al. |
| 2021/0147568 | A1 | 5/2021 | Chao et al. |
| 2021/0369781 | A1 | 12/2021 | Brentjens et al. |
| 2022/0125946 | A1 | 4/2022 | Larson et al. |
| 2022/0249659 | A1 | 8/2022 | Kroog et al. |
| 2023/0115179 | A1 | 4/2023 | Weiner et al. |

FOREIGN PATENT DOCUMENTS

| | | | |
|---|---|---|---|
| CN | 109486828 | A | 3/2019 |
| CN | 110050062 | A | 7/2019 |
| CN | 110573173 | A | 12/2019 |
| CN | 113248614 | A | 8/2021 |
| CN | 113825527 | A | 12/2021 |
| CN | 114599392 | A | 6/2022 |
| EA | 201990624 | A1 | 9/2019 |
| JP | 2017-505125 | A | 2/2017 |
| JP | 2020-521471 | A | 7/2020 |
| WO | 2016/186987 | A1 | 11/2016 |
| WO | WO-2018064588 | A2 * | 4/2018 ......... A61K 39/0011 |
| WO | 2018/187057 | A1 | 10/2018 |
| WO | 2018/218240 | A1 | 11/2018 |
| WO | 2021/051065 | A1 | 3/2021 |
| WO | 2021/092019 | A1 | 5/2021 |

OTHER PUBLICATIONS

Gezci et al. "Analysis of Circulating miRNA Profile in Plasma Samples of Glioblastoma Patients", Int J Mol Sci. May 11, 2021;22(10):5058 (Year: 2021).*
Akers et al. "A cerebrospinal fluid microRNA signature as biomarker for glioblastoma", Oncotarget. Jun. 1, 2017;8(40):68769-68779 (Year: 2017).*
An et al. "Comparison of Alterations in miRNA Expression in Matched Tissue and Blood Samples during Spinal Cord Glioma Progression", Sci Rep. Jun. 24, 2019;9(1):9169 (Year: 2019).*
ISA/220—Notification of Transmittal or Search Report and Written Opinion of the ISA, or the Declaration Mailed on Mar. 28, 2023 for WO Application No. PCT/US22/074901, 16 page(s).
Extended European Search Report Mailed on Nov. 8, 2023 for EP Application No. 20884253, 9 page(s).
Clinical trial NCT03491683 (INO-5401 and INO-9012 Delivered by Electroporation (EP) in Combination With Cemiplimab (REGN2810) in Newly-Diagnosed Glioblastoma (GBM) <URL https://clinicaltrials.gov/ct2/history/NCT03491683?V_6=View#StudyPageTop version Oct. 15, 2018. (Year: 2018).
ISA/220—Notification of Transmittal or Search Report and Written Opinion of the ISA, or the Declaration Mailed on Feb. 22, 2021 for WO Application No. PCT/US20/058891.
Lee et al. "DNA vaccines, electroporation and their applications in cancer treatment", Hum Vaccin Immunother. Aug. 2015; 11(8): 1889-1900 (Year: 2015).
Nayak et al.; "The Neurologic Assessment in Neuro-Oncology (NANO) scale: a tool to assess neurologic function for integration into the Response Assessment in Neuro-Oncology (RANO) criteria"; Neuro-Oncology; vol. 19; 2017; p. 625-635.
Okada et al.; "Immunotherapy Response Assessment in Neuro-Oncology (iRANO): A Report of the RANO Working Group"; Lancet Oncol.; vol. 16; Nov. 2015; p. e534-e542.
Reardon et al. Abstract CT114: INO-5401 and INO-9012 delivered by electroporation (EP) in combination with cemiplimab (REGN2810) in newly-diagnosed glioblastoma (GBM) (NCT03491683). Cancer Research. Jul. 2019, vol. 79, No. 13 Supplemental (p. 1-4); especially p. 1-2 (Abstract Only).
Reardon et al.; "Impact of imaging measurements on response assessment in glioblastoma clinical trials"; Neuro-Oncology; vol. 16; 2004; p. vii24-vii35.
U.S. Appl. No. 62/899,543, filed Sep. 12, 2019, U.S. Appl. No. 62/899,543.
Wen et al.; "Updated Response Assessment Criteria for High-Grade Gliomas: Response Assessment in Neuro-Oncology Working Group"; Journal of Clinical Oncology; vol. 28; Apr. 2010; p. 1963-1972.
Langer et al.; "New methods of drug delivery"; Science; vol. 249; 1990; p. 1527-1533.
Stupp et al.; "Radiotherapy plus Concomitant and Adjuvant Temozolomide for Glioblastoma"; The New England Journal of Medicine; vol. 352; 2005; p. 987-996.
Wu et al.; "Receptor-mediated in Vitro Gene Transformation by a Soluble DNA Carrier System"; The Journal of Biological Chemistry; vol. 262; Apr. 1987; p. 4429-4432.
"Inovio Announces Survival Results for INO-5401 + INO-9012 in Combination with Libtayo® (cemiplimab) in Patients with Newly Diagnosed GBM at ASCO Annual Meeting 2022"; Inovio—Powering DNA Medicines™; News Release; May 2022; 5 pages.
Wang et al.; "Research progress in the relationship between PD-1/PD-L1 and glioblastoma"; Modern Oncology; vol. 31 No. 7; Apr. 2023; p. 1344-1348 (English Abstract on p. 1344).
Inovio Announces Survival Results for INO-5401 + INO-9012 in Combination with Libtayo® (cemiplimab) in Patients with Newly Diagnosed GBM at ASCO Annual Meeting 2022 < https://s23.q4cdn.com/479936946/files/doc_news/INOVIO-Announces-Survival-Results-for-INO-5401--INO-9012-in-Combination-with-Libtayo-cemiplimab-in-Patients-with-Newly-Diagnosed-GBM--8TI11.pdf (accessed May 9, 2024).
Lin et al., Treatment of Established Tumors with a Novel Vaccine That Enhances Major Histocompatibility Class II Presentation of Tumor Antigen, Cancer Res., 1996; 56: 21-26.
Omuro et al., Radiotherapy combined with nivolumab or temozolomide for newly diagnosed glioblastoma with unmethylated MGMT promoter: An international randomized phase III trial, Neruo-Oncology 25(1), 123-134, 2023.
"Bristol-Myers Squibb Announces Phase 3 CheckMate-498 Study Did Not Meet Primary Endpoint of Overall Survival with Opdivo (nivolumab) Plus Radiation in Patients with Newly Diagnosed MGMT-Unmethylated Glioblastoma Multiforme"; https://news.bms.com/news/corporate-financial/2019/Bristol-Myers-Squibb-Announces-

(56) References Cited

OTHER PUBLICATIONS

Phase-3-CheckMate=498-Study-Did-Not-Meet-Primary-Endpoint-of-Overall-Survival-with-Opdivo-nivolumab-Plus-Radiation-in-Patients-with-MGMT-Unmethylated-Glioblastama-Multiforme/default.aspx.

"Bristol-Myers Squibb Provides Update on Phase 3 Opdivo (nivolumab) CheckMate 548 Trial in Patients with Newly Diagnosed MGMT-Methylated Glioblastoma Multiforme"; https://news:bms.com/news/corporate-financial/2019/Bristol-Myers-Squibb-Provides-Update-on-Phase-3-Opdivo-nivolumab-CheckMate--548-Trial-in-Patients-with-Newly-Diagnosed-MGMTMethylated-Glioblastoma-Multiforme/default.aspx.

Lim et al.; "Phase III trial of chemoradiotherapy with temozolomide plus nivolumab or placebo for newly diagnosed glioblastoma with methylated MGMT promoter"; Neuro-Oncology; vol. 24(11); 2022; p. 1935-1949.

* cited by examiner

STUDY SCHEMA

Figure 2A
Study Population Demographics

|  | Cohort A (n=32) | Cohort B (n=20) |
|---|---|---|
| Age ≤65 years (%) | 25 (78) | 13 (65) |
| Age ≥65 years (%) | 7 (22) | 7 (35) |
| Median Age in Years (range) | 59 (19-71) | 63 (33-78) |
| Female Sex (%) | 11 (34) | 7 (35) |
| Male Sex (%) | 21 (66) | 13 (65) |
| Karnofsky Performance Score 90-100 (%) | 23 (72) | 17 (85) |
| Karnofsky Performance Score 70-80 (%) | 9 (28) | 3 (15) |
| Median Time on Study from First Dose (Days; range) | 541 (113-722) | 557 (40-750) |
| Median Exposure* (Dosing cycles; range) of INO-5401 | 6 (1-14) | 7.5 (1-13) |
| Median Exposure* (Dosing cycles; range) of cemiplimab | 10 (1-34) | 17 (1-29) |
| Subjects of dexamethasone at Day 0 (N, %) | 14 (44) | 5 (25) |
| Discontinued Therapy to Date (N)** | 28 | 13 |

\* INO-5401 is given Q3 weeks x 4 and then Q9 weeks; cemiplimab is given Q3 weeks \*\* The majority of subjects who discontinued have discontinued therapy for progressive disease. 11 subjects continue therapy as of date of analysis.

Demographics

| | Cohort A (n=32)<br>Unmethylated MGMT | Cohort B (n=20)<br>Methylated MGMT |
|---|---|---|
| Median age (range) | 59 (19-71) | 63 (33-78) |
| Age ≤65 Years (%) | 25 (78) | 13 (65) |
| Female Sex (%) | 11 (34) | 7 (35) |
| Karnofsky Performance Score 90-100 (%) | 23 (72) | 17 (85) |
| Karnofsky Performance Score 70-80 (%) | 9 (28) | 3 (15) |
| Median Time on Study from First Dose (Mo.; range) | 17.9 (3.7-42.3) | 30.7 (1.3-41.9) |
| Median Exposure* (Dosing cycles; range) of INO-5401 | 6 (1-22) | 8 (1-20) |
| Median Exposure* (Dosing cycles; range) of cemiplimab | 10 (1-60) | 17 (1-53) |
| Subjects on dexamethasone at Day 0 (N, %) | 16 (50) | 6 (30) |
| Discontinued Study Therapy to date (N)** | 30 | 19 |

*INO-5401 is given Q3 weeks x 4 and then Q9 weeks; cemiplimab is given Q3 weeks
**The majority of subjects who discontinued have discontinued therapy for progressive disease. 3 subjects continue therapy as of April 2022

FIG. 2B

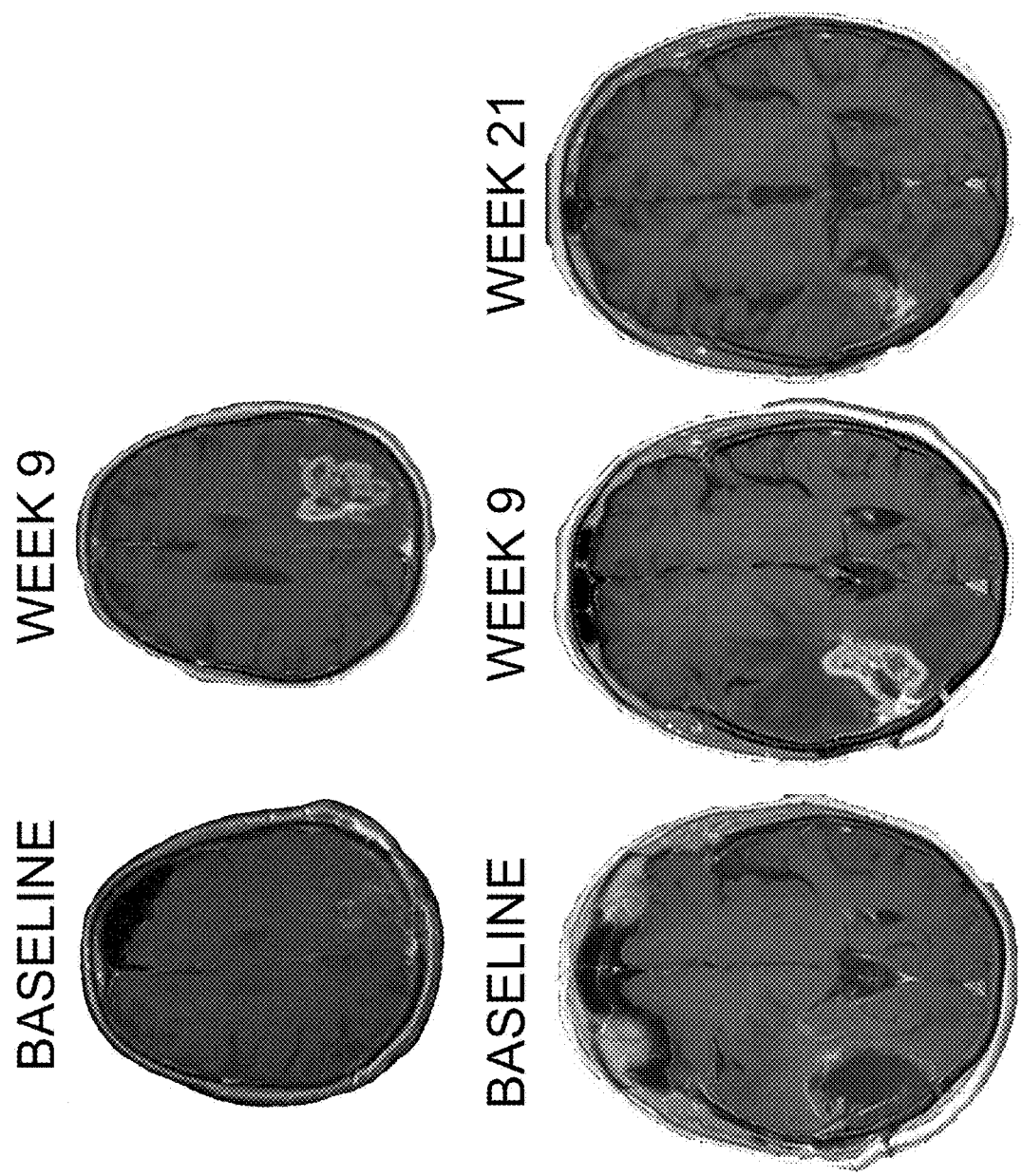

Figure 4
Immunogenicity by ELISpot
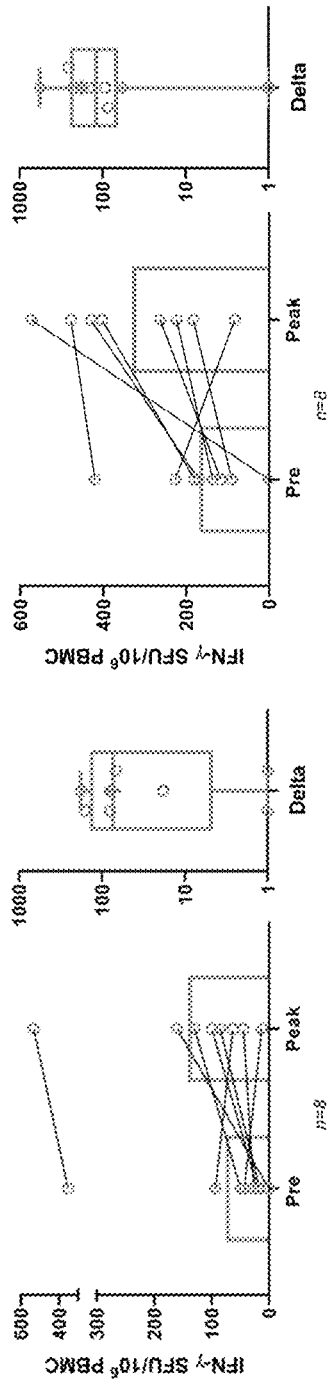
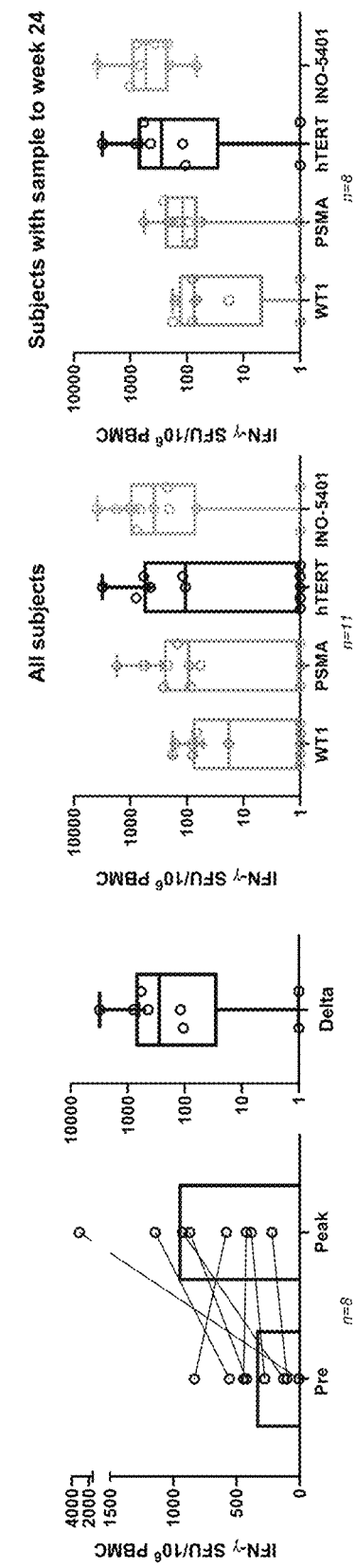

Figure 6 - Confirmed PFS (Cohort A)
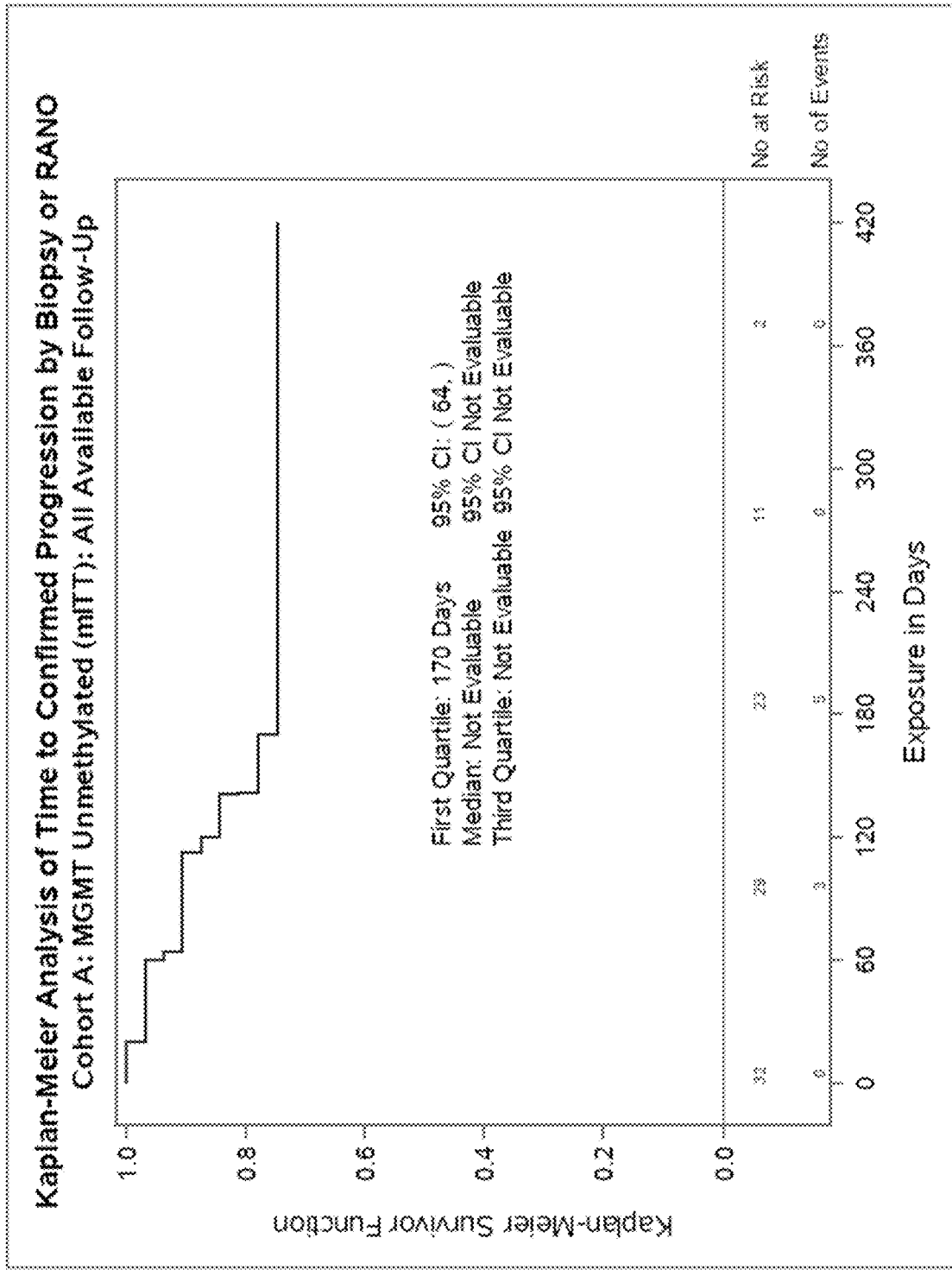

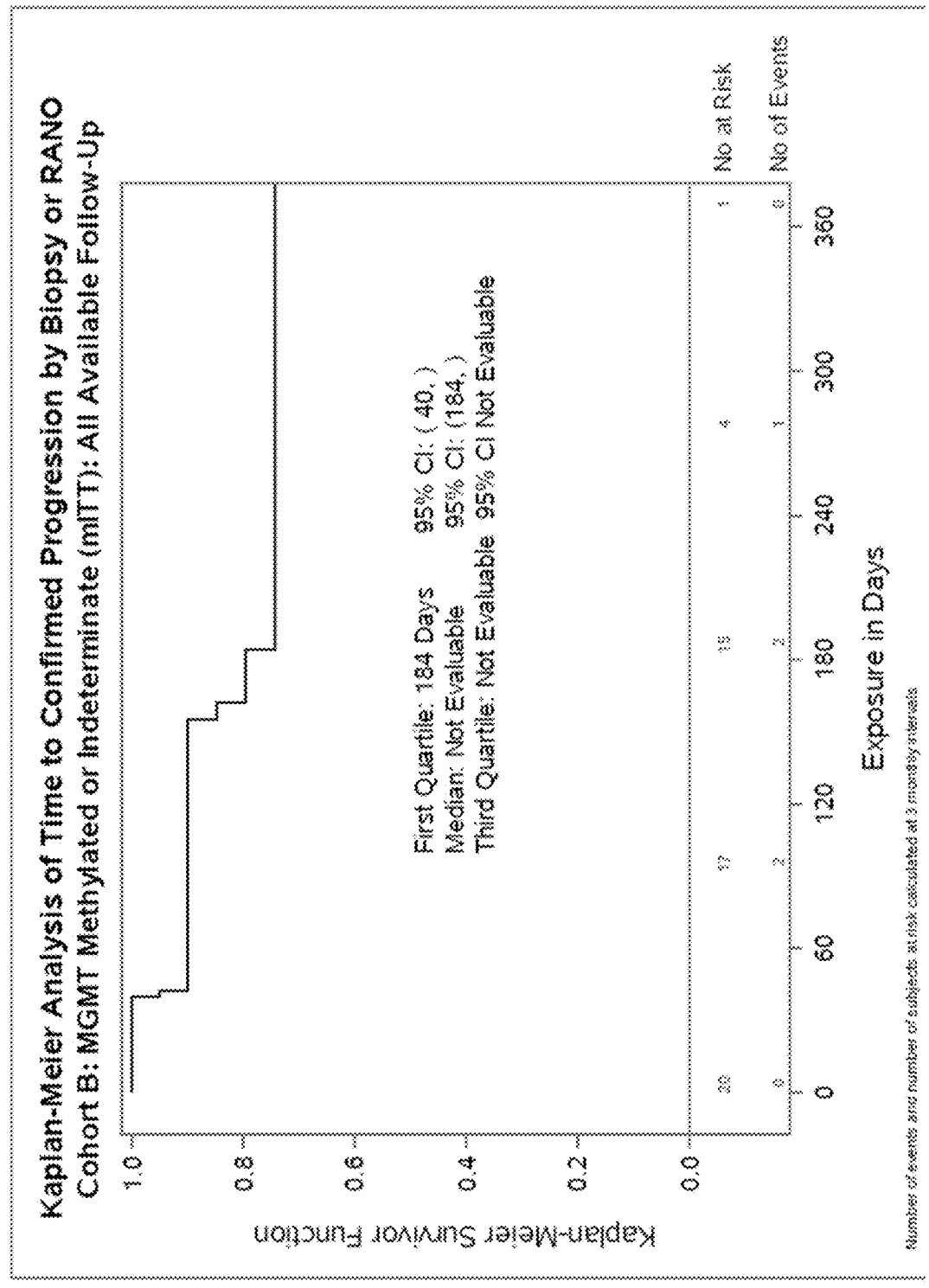
Figure 7 – Confirmed PFS (Cohort B)

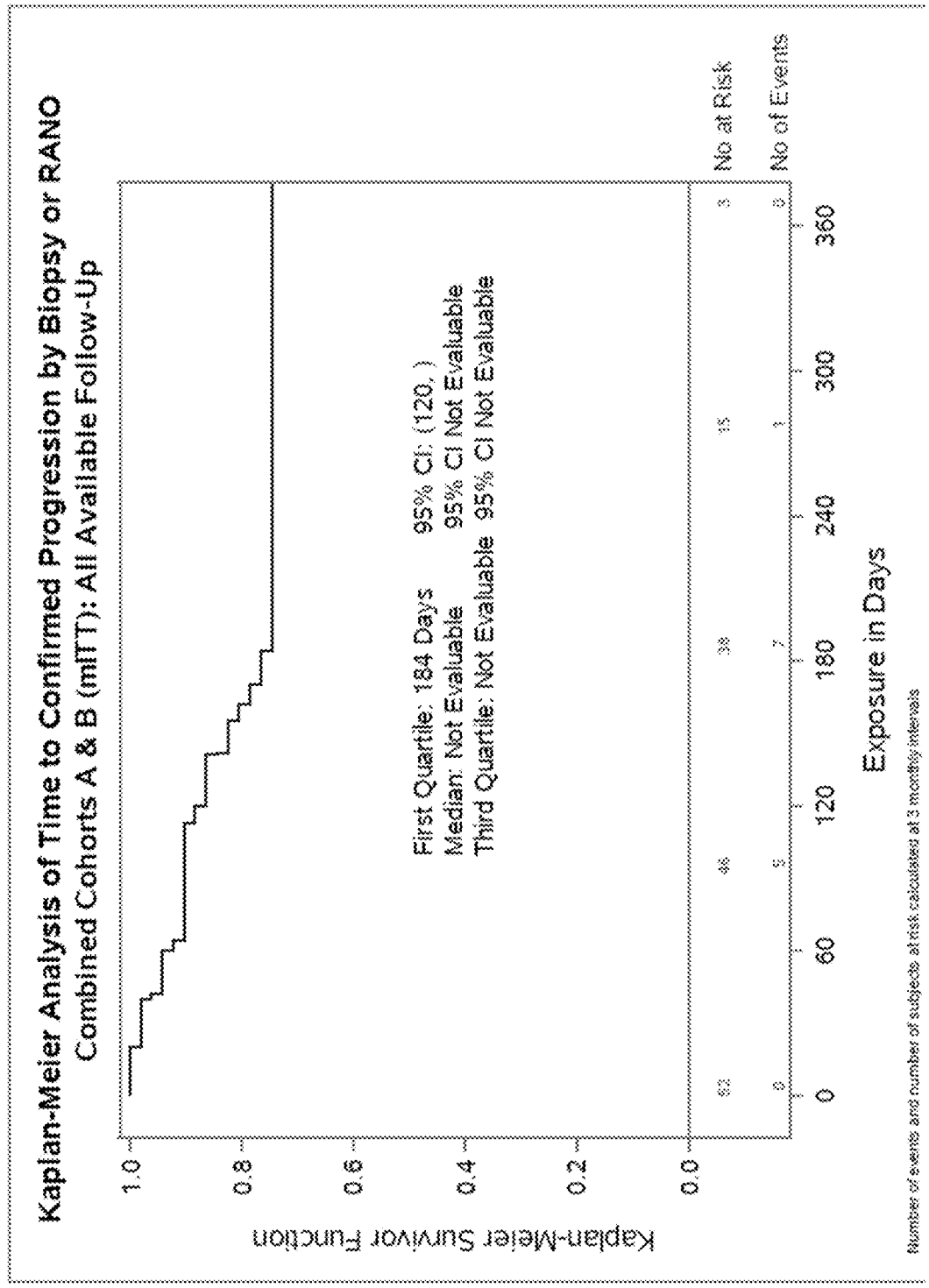
Figure 8 – Confirmed PFS (Cohort A + B)

Figure 9

| Cohort | N Total Subjects | N Event-free Subjects | PFS6 (%) | 95% CI Lower Bound | 95% CI Upper Bound |
|---|---|---|---|---|---|
| Cohort A (MGMT Unmethylated) | 32 | 24 | 75.00 | 56.60 | 88.54 |
| Cohort B (MGMT Methylated) | 20 | 16 | 80.00 | 56.34 | 94.27 |
| Both Cohorts Combined | 52 | 40 | 76.92 | 63.16 | 87.47 |

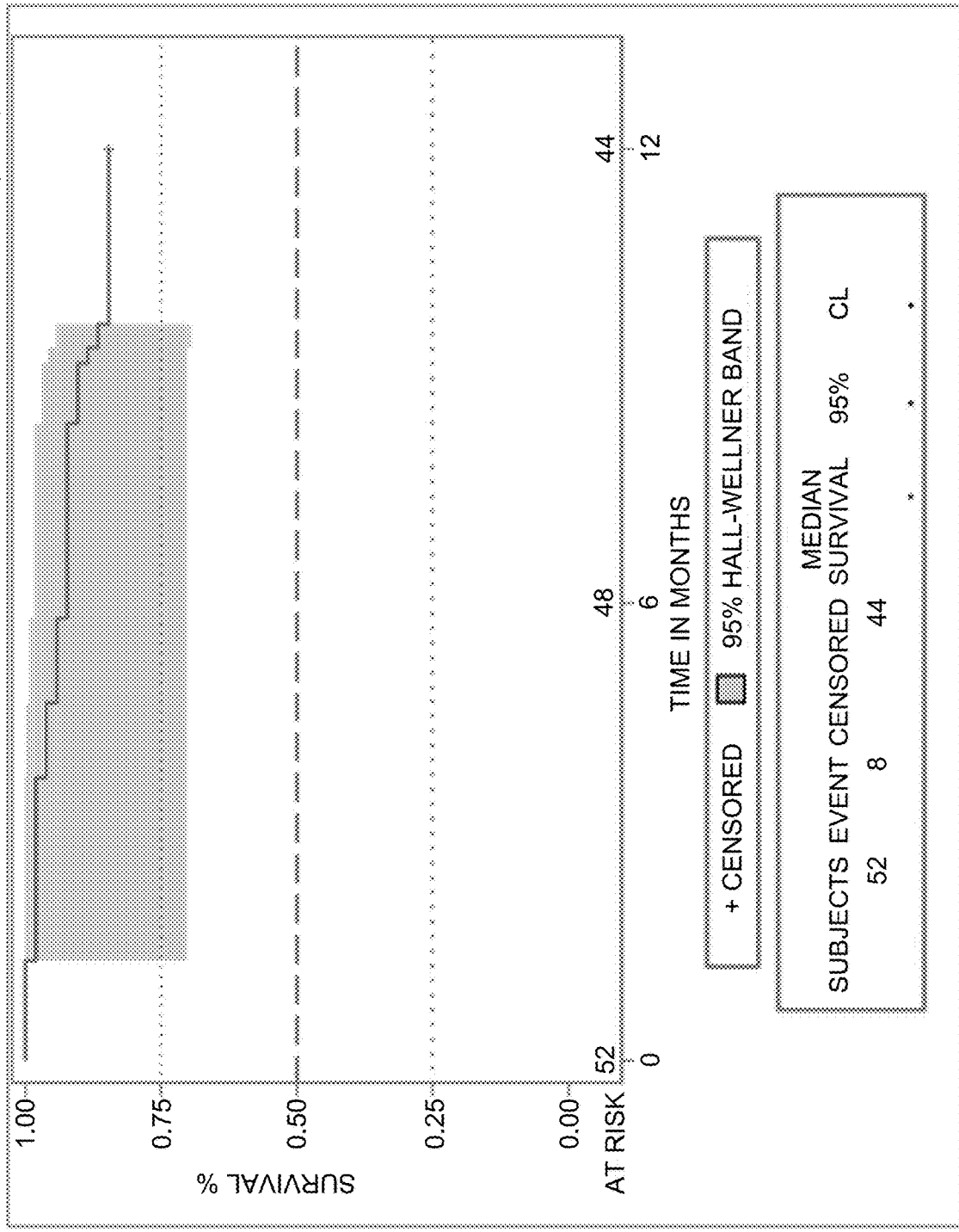

Figure 13 Interim Overall Survival at 18 Months

| | | |
|---|---|---|
| Median OS; unmethylated (Cohort A) | 17.9 mo (14.5-NR) | |
| Median OS; methylated (Cohort B) | NR (18.4-NR) | |
| Overall Survival at 12 Months | n Alive/N Total | OS12 (95% CI) |
| MGMT Unmethylated (Cohort A) | 27/32 | 84.4 (67.2-94.7) |
| MGMT Methylated (Cohort B) | 17*/20 | 85.0 (62.1-96.8) |
| Combined | 44/52 | 84.6 (71.9-93.1) |
| Overall Survival at 18 Months | n Alive/N Total | OS18 (95% CI) |
| MGMT Unmethylated (Cohort A) | 16/32 | 50 (31.9-68.1) |
| MGMT Methylated (Cohort B) | 14/20* | 70 (45.7-88.1) |
| Combined | 30/52 | 57.7 (14.5-71.3) |

* Two patients in Cohort B withdrew consent for additional follow-up at Week 3 and are included in the denominator NR: not reached Figure 14  NCI CTCAE ≥3 Adverse Events Reported in More than One Subject

| System Organ Class<br>Preferred Term | Unmethylated MGMT (Cohort A) (N=32) n(%) | Methylated MGMT (Cohort B) (N=20) n(%) | Combined Unmethylated/ Methylated MGMT (N=52) n(%) |
|---|---|---|---|
| Blood and lymphatic system disorders | | | |
| Anaemia | 1 (3.1) | 1 (5.0) | 2 (3.8) |
| Gastrointestinal disorders | | | |
| Diarrhoea | 2 (6.3) | 0 (0.0) | 2 (3.8) |
| Infections and infestations | | | |
| Pneumonia | 2 (6.3) | 0 (0.0) | 2 (3.8) |
| Investigations | | | |
| Amylase increased | 1 (3.1) | 1 (5.0) | 2 (3.8) |
| Alanine aminotransferase increased | 2 (6.3) | 2 (10.0) | 4 (7.7) |
| Lipase increased | 1 (3.1) | 2 (10.0) | 3 (5.8) |
| Lymphocyte count decreased | 4 (12.5) | 2 (10.0) | 6 (11.5) |
| Neutrophil count decreased | 0 (0.0) | 3 (15.0) | 3 (5.8) |
| Platelet count decreased | 2 (6.3) | 4 (20.0) | 6 (11.5) |
| White blood cell count decreased | 0 (0.0) | 3 (15.0) | 3 (5.8) |
| Metabolism and nutrition disorders | | | |
| Hyponatraemia | 2 (6.3) | 0 (0.0) | 2 (3.8) |
| Musculoskeletal and connective tissue disorders | | | |
| Muscular weakness | 2 (6.3) | 0 | 2 (3.8) |
| Neoplasms benign, malignant and unspecified (incl cysts and polyps) | | | |
| Tumour inflammation | 3 (9.4) | 1 (5.0) | 4 (7.7) |
| Nervous system disorders | | | |
| Hemiparesis | 1 (3.1) | 1 (5.0) | 2 (3.8) |
| Seizure | 4 (12.5) | 0 (0.0) | 4 (7.7) |
| Respiratory, thoracic and mediastinal disorders | | | |
| Pneumonitis | 2 (6.3) | 0 (0.0) | 2 (3.8) |
| Pulmonary embolism | 2 (6.3) | 1 (5.0) | 3 (5.8) |
| Skin and subcutaneous tissue disorders | | | |
| Rash maculo-papular | 2 (6.3) | 0 (0.0) | 2 (3.8) |

Note: MGMT = O6-methylguanine methyltransferase. TEAE = Treatment-emergent adverse event. Adverse events are coded using Medical Dictionary for Regulatory Activities (MedDRA) version 22. If a subject experienced more than one event in a given system organ class, that subject is counted once for that system organ class. If a subject experienced more than one event with a given preferred term, that subject is counted only once for that preferred term by highest severity grade.

Figure 15 Immune-Related Adverse Events

| System Organ Class Preferred Term | Unmethylated MGMT (Cohort A) (N=32) | Methylated MGMT (Cohort B) (N=20) | Combined Unmethylated/ Methylated MGMT (N=52) |
|---|---|---|---|
| Cardiac disorders | | | |
| Myocarditis | | 1 | 1 |
| Endocrine disorders | | | |
| Diabetes insipidus | 0 | 1 | 1 |
| Immune-related hypothyroidism | 2 | 0 | 2 |
| Gastrointestinal disorders | | | |
| Diarrhoea | 3 | 1 | 4 |
| Immune-mediated enterocolitis | 1 | 0 | 1 |
| Pancreatitis | 0 | 1 | 1 |
| General disorders and administration site conditions | | | |
| Fatigue | | 1 | 1 |
| Influenza like illness | 1 | 1 | 2 |
| Night sweats | 0 | 1 | 1 |
| Pyrexia | 2 | 2 | 4 |
| Hepatobiliary disorders | | | |
| Immune-mediated hepatitis* | 3 | 0 | 3 |
| Immune system disorders | | | |
| Hypersensitivity | 1 | 0 | 1 |
| Myasthenia gravis | 0 | 1 | 1 |
| Investigations | | | |
| Alanine aminotransferase increased | 4 | 1 | 5 |
| Amylase increased | 1 | 0 | 1 |
| Aspartate aminotransferase increased | 4 | 0 | 1 |
| Increased alkaline phosphatase | 1 | 0 | 1 |
| Lipase increased | 0 | 1 | 1 |
| Transaminitis | 1 | 0 | 1 |
| Musculoskeletal and connective tissue disorders | | | |
| Arthralgia* | 4 | 0 | 4 |
| Eosinophilic fasciitis | 0 | 1 | 1 |
| Muscular weakness | 0 | 1 | 1 |
| Myositis | 0 | 1 | 1 |
| Nervous system disorders | | | |
| Brain Oedema | 2 | 0 | 2 |
| Encephalitis autoimmune | 0 | 1 | 1 |
| Headache | 0 | 1 | 1 |
| Neoplasms benign, malignant and unspecified (incl cysts and polyps) | | | |

Figure 15 Immune-Related Adverse Events - continued

| | | | |
|---|---|---|---|
| Tumour inflammation | 4 | 1 | 5 |
| Renal and urinary disorders | | | |
| Acute kidney injury | 1 | 1 | 2 |
| Autoimmune nephritis* | 3 | 0 | 3 |
| Haematuria | 0 | 1 | 1 |
| Respiratory, thoracic and mediastinal disorders | | | |
| Pneumonitis | 3 | 0 | 3 |
| Skin and subcutaneous tissue disorders | | | |
| Pruritus | 1 | 1 | 2 |
| Rash | 0 | 1 | 1 |
| Rash erythematous | 1 | 0 | 1 |
| Rash maculo-papular | 2 | 0 | 2 |
| Rash papular | 1 | 0 | 1 |
| Urticaria | 1 | 0 | 1 |

*Subject experienced same event more than one time.
Arthralgia: 2 events reported for one subject
Autoimmune nephritis: 3 events reported for one subject
Immune-mediated hepatitis: 2 events reported for one subject

```
                            SEQUENCE LISTING

Sequence total quantity: 31
SEQ ID NO: 1            moltype = AA  length = 117
FEATURE                 Location/Qualifiers
source                  1..117
                        mol_type = protein
                        organism = synthetic construct
SEQUENCE: 1
EVQLLESGGV LVQPGGSLRL SCAASGFTFS NFGMTWVRQA PGKGLEWVSG ISGGGRDTYF   60
ADSVKGRFTI SRDNSKNTLY LQMNSLKGED TAVYYCVKWG NIYFDYWGQG TLVTVSS     117

SEQ ID NO: 2            moltype = AA  length = 107
FEATURE                 Location/Qualifiers
source                  1..107
                        mol_type = protein
                        organism = synthetic construct
SEQUENCE: 2
DIQMTQSPSS LSASVGDSIT ITCRASLSIN TFLNWYQQKP GKAPNLLIYA ASSLHGGVPS   60
RFSGSGSGTD FTLTIRTLQP EDFATYYCQQ SSNTPFTFGP GTVVDFR                107

SEQ ID NO: 3            moltype = AA  length = 8
FEATURE                 Location/Qualifiers
source                  1..8
                        mol_type = protein
                        organism = synthetic construct
SEQUENCE: 3
GFTFSNFG                                                             8

SEQ ID NO: 4            moltype = AA  length = 8
FEATURE                 Location/Qualifiers
source                  1..8
                        mol_type = protein
                        organism = synthetic construct
SEQUENCE: 4
ISGGGRDT                                                             8

SEQ ID NO: 5            moltype = AA  length = 10
FEATURE                 Location/Qualifiers
source                  1..10
                        mol_type = protein
                        organism = synthetic construct
SEQUENCE: 5
VKWGNIYFDY                                                          10

SEQ ID NO: 6            moltype = AA  length = 6
FEATURE                 Location/Qualifiers
source                  1..6
                        mol_type = protein
                        organism = synthetic construct
SEQUENCE: 6
LSINTF                                                               6

SEQ ID NO: 7            moltype =     length =
SEQUENCE: 7
000

SEQ ID NO: 8            moltype = AA  length = 9
FEATURE                 Location/Qualifiers
source                  1..9
```

```
                        mol_type = protein
                        organism = synthetic construct
SEQUENCE: 8
QQSSNTPFT                                                            9

SEQ ID NO: 9            moltype = AA   length = 444
FEATURE                 Location/Qualifiers
source                  1..444
                        mol_type = protein
                        organism = synthetic construct
SEQUENCE: 9
EVQLLESGGV LVQPGGSLRL SCAASGFTFS NFGMTWVRQA PGKGLEWVSG ISGGGRDTYF    60
ADSVKGRFTI SRDNSKNTLY LQMNSLKGED TAVYYCVKWG NIYFDYWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGK                                         444

SEQ ID NO: 10           moltype = AA   length = 214
FEATURE                 Location/Qualifiers
source                  1..214
                        mol_type = protein
                        organism = synthetic construct
SEQUENCE: 10
DIQMTQSPSS LSASVGDSIT ITCRASLSIN TFLNWYQQKP GKAPNLLIYA ASSLHGGVPS    60
RFSGSGSGTD FTLTIRTLQP EDFATYYCQQ SSNTPFTFGP GTVVDFRRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 11           moltype = DNA   length = 2283
FEATURE                 Location/Qualifiers
source                  1..2283
                        mol_type = unassigned DNA
                        organism = unidentified
SEQUENCE: 11
atgtggaacg cactgcatga gactgattct gctgtcgcac tgggacggag accccggtgg    60
ctgtgcgctg gagcactggt gctggccggc gggggattcc tgctgggatt cctgtttgga   120
tggtttatca aaagctccag cgaggctacc aatattaccc ctaagcacaa taagaaagca   180
ttcctggatg aactgaaagc cgagaacatc aagaaattcc tgtacaactt cacaagaatt   240
ccacatctgc tgcactga gcagaacttc agctgcaa aacagatcca gagtcagtgg       300
aaggaatttg ggctggactc agtggagctg acccactacg atgtcctgct gtcctatcca   360
aataagactc atcccaacta catctctatc attaacgaag acggaaatga gattttcaac   420
acctctctgt tgaaccccc tccacccggc tatgagaatg tcagtgacgt ggtccctcca   480
ttctcagcct tcagccccca ggggatgcct gagggagatc tggtgtacgt caattatgct   540
agaacagaag acttctttaa gctggagagg gatatgaaca tcaactgttc cggcaagatc   600
gtgattgccc ggtacgggaa ggtgttcaga ggaaataagg tcaaaaacgc tcagctggcc   660
ggagctaccg cgctgatcct gtacagcgac cccgctgatt attttgcacc tggcgtgaag   720
tcctatccag acgatggaaa tctgcccggc ggggagtgc agaggggaaa catcctgaac   780
ctgaatggag ccggcgatcc tctgactcca ggatacccg caacgaata cgcttatgcc   840
cggggaattg cagaggccgt gggcctgcct agcatcccag tccatcccat ggctatac    900
gatgcccaga agctgctgga gaaaatgggg gggagcgctc ccctgactc tagttggaag   960
ggctccctga agtgcctta caatgtcggg ccaggattca ctgggaactt ttctacccag  1020
aaggtgaaaa tgcacatcca tagtaccagc gaggtgacga gaatctacaa cgtcattggc  1080
accctgagag cgccgtgga gcctgatcgc tatgtcattc tggaggcca cagagactca  1140
tgggtgttcg ggggaatcga tccacagagc ggagcagctg tggtccatga aattgtgcgc  1200
agctttggga ccctgaagaa agagggatgg cgacccaggc gcacaatcct gttcgcatcc  1260
tgggacgccg aggaatttgg gctgctgggc agcacagaat gggccgagga aaattctcgc  1320
ctgctgcagg agcgagggt ggcttacatc aatgcagact caagcattga aggaaactat  1380
accctgcggg tggattgcac acccctgatg tacagtctgg tctataacct gacaaaggag  1440
ctgaaatcac ctgacgaggg cttcgaaggg aaaagcctgt acgaatcctg gactgagaag  1500
agcccatccc ccgaattcag cggcatgcct aggatctcta agctgggcag tgggaacgat  1560
tttgaggtgt tctttcagcg cctgaggaatt gcctctgact cggtcattgg cacaaaaaat  1620
tgggagacta acaagttctc ctcttaccca ctgtatcaca gcgtgtacga gacttatgaa  1680
ctggtcgaga aattctacga cccccacttt aagtatcatc tgaccgtggc acaggtcagg  1740
ggcgggatgg tgttcgaact ggccaatagc atcgtcctgc catttgactg tcagattac  1800
gctgtggtcc tgcggaagta cgcagacaag atctataaca tctccatgaa gcaccccag  1860
gagatgaagg cctattctgt gagtttcgat tccctgtttt ctgccgtcaa aaatttcacc  1920
gaaatcgcta gtaagtttc agagcgcctg caggactgg ataagtccaa tcccatcctg  1980
ctgcggatta tgaacgatca gctgatgttc ctggaaagag cctttatcga ccctctgggc  2040
ctgcctgata gaccattcta caggcacgtg atctacgcac tagttcaca taacaagtac  2100
gccggcgagt ctttcccagg gatctatgac gctctgtttg atattgaatc aaaggtggac  2160
cccagcaaag catgggggcga ggtcaagaga cagatcagca ttgcagcctt tacagtgcag  2220
gccgccgccg aaaccctgtc cgaagtcgct tacccatacg atgtccccga ttacgcatga  2280
taa                                                                2283

SEQ ID NO: 12           moltype = DNA   length = 2334
FEATURE                 Location/Qualifiers
```

| source | 1..2334 |
| --- | --- |
| | mol_type = unassigned DNA |
| | organism = unidentified |

SEQUENCE: 12

```
atggactgga catggattct gttcctggtc gccgccgcaa ctcgcgtgca ttcctggaac    60
gcactgcatg agactgattc tgctgtcgca ctgggacgga gaccccggtg gctgtgcgct   120
ggagcactgg tgctggccgg cggggggatt ctgctgggat tcctgtttgg ctggtttatc   180
aaaagctcca gcgaggctac caatattacc cctaagcaca ataagaaagc attcctggat   240
gaactgaaag ccgagaacat caagaaattc ctgtacaact tcacaagaat tccacatctg   300
gctggcactg agcagaactt ccagctggca aaacagatcc agagtcagtg gaaggaattt   360
gggctggact cagtggagct gacccactac gatgtcctgc tgtcctatcc aaataagact   420
catcccaact acatctctat cattaacgaa gacggaaatg agattttcaa cacctctctg   480
tttgaacccc ctccaccccgg ctatgagaat gtcagtgacg tggtccctcc attctcagcc   540
ttcagccccc aggggatgcc tgaggagat ctggtgtacg tcaattatgc tagaacagaa   600
gacttcttta gctggagag ggatatgaaa atcaactgtt ccggcaagat cgtgattgcc   660
cggtacggga aggtgttcag aggaaataag gtcaaaaacg ctcagctggc cggagctacc   720
ggcgtgatcc tgtacagcga ccccgctgat tattttgcac ctggcgtgaa gtcctatcca   780
gacggatgga atctgccccgg cggggagtg cagaggggaa acatcctgaa cctgaatgga   840
gccggcgatc ctctgactcc aggatacccc gccaacgaat acgcttatcg ccggggaatt   900
gcagaggccg tgggcctgcc tagcatccca gtccatccca ttggctatta cgatgcccag   960
aagctgctgg agaaaatggg cgggagcgct ccccctgact ctagttggaa gggctccctg  1020
aaagtgcctt acaatgtcgg gccaggattc actgggaact tttctaccca gaaggtgaaa  1080
atgcacatcc atagtaccag cgaggtgaca cgaatctaca acgtcattgg caccctgaga  1140
ggcgccgtgg agcctgatcg ctatgtcatt ctgggaggcc acagagactc atgggtgttc  1200
gggggaatcg atccacagag cggagcagct gtggtccatg aaattgtgcg cagctttggg  1260
acgctgaaga aagagggatg gcgacccgaa gcgcacaatc tgttcgcatc ctgggacgcc  1320
gaggaatttg gctgctggg cagcacagaa tgggccgagg aaaattctcg cctgctgcag  1380
gagcgagggg tggcttacat caatgcagac tcaagcattg aaggaaacta ccccctgcgg  1440
gtggattgca caccccctgat gtacagtctg gtctataacc tgacaaagga gctgaaatca  1500
cctgacgagg gcttcgaagg gaaaagcctg tacgaatcct ggactgagaa gagcccatcc  1560
cccgaattca gcggcatgcc taggatctct aagctgggca gtgggaacga ttttgaggtg  1620
ttctttcagc gcctgggaat tgcctctggc cgagctcggt acacaaaaaa ttgggagact  1680
aacaagttct cctcttaccc actgtatcac agcgtgtacg agacttatga actggtcgag  1740
aaattctacg accccacttt taagtatcat ctgaccgtgg cacaggtcag gggcgggatg  1800
gtgttcgaac tggccaatag catcgtcctg ccatttgact gtcgagatta cgctgtggtc  1860
ctgcggaagt acgcagacaa gatctataac atctccatga agcaccccca ggagatgaag  1920
gcctattctg tgagtttcga ttccctgttt tctgccgtca aaaatttcac cgaaatcgct  1980
agtaagttt cagagcgcct gcaggacctg ataagtcca atcccatcct gctgcggatt  2040
atgaacgatc agctgatgtt cctggaaaga gcctttatcg accctctggg cctgcctgat  2100
agaccattct acaggcacgt gatctacgca cctagttcac ataacaagta cgccggcgag  2160
tctttcccag ggatctatga cgctctgttt gatattgaat caaaggtgga ccccagcaaa  2220
gcatgggggc aggtcaagag acagatcagc attgcagcct tacagtgca ggccgccgcc  2280
gaaacccctgt ccgaagtcgc ttacccatac gatgtccccg attacgcatg ataa         2334
```

| SEQ ID NO: 13 | moltype = AA length = 750 |
| --- | --- |
| FEATURE | Location/Qualifiers |
| source | 1..750 |
| | mol_type = protein |
| | organism = unidentified |

SEQUENCE: 13

```
MWNALHETDS AVALGRRPRW LCAGALVLAG GGFLLGFLFG WFIKSSSEAT NITPKHNKKA    60
FLDELKAENI KKFLYNFTRI PHLAGTEQNF QLAKQIQSQW KEFGLDSVEL THYDVLLSYP   120
NKTHPNYISI INEDGNEIFN TSLFEPPPPG YENVSDVVPP FSAFSPQGMP EGDLVYNYA    180
RTEDFFKLER DMKINCSGKI VIARYGKVFR GNKVKNAQLA GATGVILYSD PADYFAPGVK   240
SYPDGWNLPG GGVQRGNILN LNGAGDPLTP GYPANEYAYR RGIAEAVGLP SIPVHPIGYY   300
DAQKLLEKMG GSAPPDSSWK GSLKVPYNVG PGFTGNFSTQ KVKMHIHSTS EVTRIYNVIG   360
TLRGAVEPDR YVILGGHRDS WVFGGIDPQS GAAVVHEIVR SFGTLKKEGW RPRRTILFAS   420
WDAEEFGLLG STEWAEENSR LLQERGVAYI NADSSIEGNY TLRVDCTPLM YSLVYNLTKE   480
LKSPDEGFEG KSLYESWTEK SPSPEFSGMP RISKLGSGND FEVFFQRLGI ASGRARYTKN   540
WETNKFSSYP LYHSVYETYE LVEKFYDPTF KYHLTVAQVR GGMVFELANS IVLPFDCRDY   600
AVVLRKYADK IYNISMKHPQ EMKAYSVSFD SLFSAVKNFT EIASKFSERL QDLDKSNPIL   660
LRIMNDQLMF LERAFIDPLG LPDRPFYRHV IYAPSSHNKY AGESFPGIYD ALFDIESKVD   720
PSKAWGEVKR QISIAAFTVQ AAAETLSEVA                                    750
```

| SEQ ID NO: 14 | moltype = AA length = 767 |
| --- | --- |
| FEATURE | Location/Qualifiers |
| source | 1..767 |
| | mol_type = protein |
| | organism = unidentified |

SEQUENCE: 14

```
MDWTWILFLV AAATRVHSWN ALHETDSAVA LGRRPRWLCA GALVLAGGGF LLGFLFGWFI    60
KSSSEATNIT PKHNKKAFLD ELKAENIKKF LYNFTRIPHL AGTEQNFQLA KQIQSQWKEF   120
GLDSVELTHY DVLLSYPNKT HPNYISIINE DGNEIFNTSL FEPPPPGYEN VSDVVPPFSA   180
FSPQGMPEGD LVYNYARTE DFFKLERDMK INCSGKIVIA RYGKVFRGNK VKNAQLAGAT   240
GVILYSDPAD YFAPGVKSYP DGWNLPGGGV QRGNILNLNG AGDPLTPGYP ANEYAYRRGI   300
AEAVGLPSIP VHPIGYYDAQ KLLEKMGGSA PPDSSWKGSL KVPYNVGPGF TGNFSTQKVK   360
MHIHSTSEVT RIYNVIGTLR GAVEPDRYVI LGGHRDSWVF GGIDPQSGAA VVHEIVRSFG   420
TLKKEGWRPR RTILFASWDA EEFGLLGSTE WAEENSRLLQ ERGVAYINAD SSIEGNYTLR   480
VDCTPLMYSL VYNLTKELKS PDEGFEGKSL YESWTEKSPS PEFSGMPRIS KLGSGNDFEV   540
```

```
FFQRLGIASG RARYTKNWET NKFSSYPLYH SVYETYELVE KFYDPTFKYH LTVAQVRGGM    600
VFELANSIVL PFDCRDYAVV LRKYADKIYN ISMKHPQEMK AYSVSFDSLF SAVKNFTEIA    660
SKFSERLQDL DKSNPILLRI MNDQLMFLER AFIDPLGLPD RPFYRHVIYA PSSHNKYAGE    720
SFPGIYDALF DIESKVDPSK AWGEVKRQIS IAAFTVQAAA ETLSEVA                  767

SEQ ID NO: 15          moltype = DNA  length = 1332
FEATURE                Location/Qualifiers
source                 1..1332
                       mol_type = unassigned DNA
                       organism = unidentified
SEQUENCE: 15
ggatccgcca ccatggactg gacctggatt ctgttcctgg tcgccgccgc aacacgggtg     60
catagtggga gtgatgtgag agacctgaac gccctgctgc cagcagtgcc atccctgcct    120
ggcggggag gctgcgctct gccagtctct ggagcagctc agtggggtcc cgtgctggac    180
tttgcacccc ctgcagcccc ttacggaagt ctgggcggcc acactcatt catcaaacag    240
gagccaagct ggggcgggc agatcctcat gaggaacagt gcctgtcagc cttcacagtc    300
cactttagcg ggcagttcac tggaaccgca ggagcttgta gataccggacc ctttggagca    360
ccacccccctt cccaggcacc ttctggacag gcacgcatgt tcccaaacgc tcccatctcg    420
cctaattgtc tggaaagcca gcccgctatt aggaaccagg gctactccac agtggcattt    480
gacgggactc ctagctatgg acataccca tccaccatg ctgcacagtt tcctaatcac    540
tccttcaagc atgaggaccc catgggacag caggggtccc tggagaaaca gcagtactct    600
gtgcccctc ccgtgtacgg atgccacaca ccaactgaca gttgtacagg ctcacaggcc    660
ctgctgctgc gaactccata acagtgat aatctgtatc agatgaccct cacagctgag    720
tgcatgacat ggaaccagat gaatctgggc agcacactga aaggccatgc cactgggtac    780
gaatctgaca ccacaccac acctatgctg tacagttgtg gagcccagta tagaatccac    840
actcatggag tcttcagagg cattcaggat gtgcggagag tcccaggagt ggcaccaact    900
atcgtgcgga gcgcctccga gaccaacgaa aagcgcccct ttatgggcgc ctaccctgga    960
ggcaataagc ggtatttcaa actgtctcac ctgcagatgg ggagtagaaa ggggaccgga   1020
gagaaaccctt atcagggcga ctttaaagat ggggaaaggc gcttctctcg cagtgaccag   1080
ctgaagcgag gacagcgacg aggaaccggg gtgaagccat ttcagtgcaa aacatgtcag   1140
agaaagttct caaggagcga tcacctgaag acccatacaa gaactcacac cggcaagacc   1200
agcgagaaac cattttcctg ccgatggccc tcttgtcaga gaaattcgc ccgctccgac   1260
gaactggtcc gacaccacaa tatgcatcag agaaatatga caaaactgca gctggctctg   1320
tgataactcg ag                                                       1332

SEQ ID NO: 16          moltype = AA  length = 436
FEATURE                Location/Qualifiers
source                 1..436
                       mol_type = protein
                       organism = unidentified
SEQUENCE: 16
MDWTWILFLV AAATRVHSGS DVRDLNALLP AVPSLPGGGG CALPVSGAAQ WAPVLDFAPP     60
AAPYGSLGGP HSFIKQEPSW GGADPHEEQC LSAFTVHFSG QFTGTAGACR YGPFGAPPPS    120
QAPSGQARMF PNAPYLPNCL ESQPAIRNQG YSTVAFDGTP SYGHTPSHHA AQFPNHSFKH    180
EDPMGQQGSL GEQQYSVPPP VYGCHTPTDS CTGSQALLLR TPYNSDNLYQ MTSQLECMTW    240
NQMNLGSTLK GHATGYESDN HTTPMLYSCG AQYRIHTHGV FRGIQDVRRV PGVAPTIVRS    300
ASETNEKRPF MGAYPGGNKR YFKLSHLQMG SRKGTGEKPY QGDFKDGERR FSRSDQLKRG    360
QRRGTGVKPF QCKTCQRKFS RSDHLKTHTR THTGKTSEKP FSCRWPSCQK KFARSDELVR    420
HHNMHQRNMT KLQLAL                                                   436

SEQ ID NO: 17          moltype = DNA  length = 3447
FEATURE                Location/Qualifiers
source                 1..3447
                       mol_type = other DNA
                       organism = synthetic construct
SEQUENCE: 17
atggattgga catggattct gttcctggtc gcagccgcca cacgagtgca tagccctaga     60
gccccacggg gtagagcagt ccgcagcctg ctgcgcagcc gataccggga agtgctgcct    120
ctggccacct ttgtccggag actgggacca cagggcaggc gcctggtgca gcgcggcgac    180
cccgcagctt tccgagcact ggtggccaca tgcctggtgt gcgtgccatg ggatgcacgg    240
cccctccag cagcccctag ctttagacag gtgtcctgcc tgaaagaact ggtcgcaagg    300
gtggtccagc ggctgtgcga gagagcgcc aggaacgtgc tggcattcgg ctttgcactg    360
ctggacgag ctagggcgg gccccctgag gcattcacca caagcgtgcg ctcctactg    420
ccaaatacag tcactgatac cctgcgaggc tccggacgac agggagtgct gcccggacgg    480
gtggggacg atgtgctggt ccacctgctg ctagatgcg cactgtatgt gctggtcgct    540
ccctcttgcg cataccaggt gtgcggacca cccctgtatg acctgggcgc tgcaacccag    600
gcaagacctc caccccacgc ctctggcact agaagggag tgggcaccga acaggcatgg    660
aaccatagtg tcagggaggc aggagtgcca ctgggactgc cagcacctgg ggctcgccga    720
cggagagga gtgccggacg gtcactgcca cgtgctaaga caccaaggcg cggagcccgg    780
ccagaaccag agaggacacc tgtgggacag ggaagctggg cacacccctgg aagaactagg    840
gggccaagta atagggcctt ctgcctggtc tcaccagcac gaccagcaga ggaagctact    900
tctctggagg gagctctgag tggcaccggg cactcatcc ctagtgtggg aagacagcac    960
catgcaggcc ctcaagcac agccggcct cccggccat gggacactcc ttgtccaccc   1020
gtgtcactga aaaccaaaca cttttctgtat agctccggga ataaggagca gctgcggcc   1080
tcttttcctg tgtctagtct gagaccagt ctgaccggaa cacgacggct ggtgaaaaca   1140
atctttctgg gtcccgccc ttgatgcca ggaacccca aaggacacc tcgactgcca   1200
cagcggtact ggcagatgcg gccactgttc ctggagctgc tggcaatca cgtcagtgc   1260
ccctatgggg cactgctgcg aacacattgt cctctgcggg cagccgtgac tccagctgca   1320
ggagtctgcg ccagggaaaa gccacagggc agcgtgcag ctcctgagga agaggacacc   1380
```

```
gatccacgcc gactggtgca gctgctgaga cagcactcaa gccctggca ggtgtacgga    1440
tttctgaggg cctgtctgcg gagactggtg cctccaggac tgtggggtc caggcacaac    1500
gaaaggcgct ttctgcgcaa tactaagaaa ttcatcagcc tgggcaagca tgctaaactg    1560
tccctgcagg agctgacctg gaaaatgagt gtgcgcgact cgcatggct gcgacggtca    1620
ccaggagtcg ggtgcgtgcc tgcagccgag caccgcctgc gagaagagat tctggccaag    1680
tttctgcatt ggctgatgtc agtgtacgtg gtcgaactgc tgcggagctt cttttatgtg    1740
acagagacta ccttccagaa aaactacctg ttctttatc gcaagtcagt gtggagcaaa    1800
ctgcagtcaa tcggcattcg gcagcacctg aagagagtgc agctgaggga actgagtgaa    1860
gccgaggtcc ggcagcatag agaggcaagg cctgccctgc tgacctcccg gctgagattc    1920
ctgcctaagc cagacgggct gagaccaatc gtgaacatgt attacgtggt cggagcacgg    1980
accttccgga gggaaaaacg cgctgagcga ctgacatccc gcgtgaagac tctgttctct    2040
gtcctgaatt atgagcgagc tcgccgaccc ggactgctgg gagcatcgt gctgggactg    2100
gacgatattc accgggcttg gagagcattt gtcctgaggg tgcgcgcaca ggaccctccc    2160
ccagaactgt acttcgtgaa agtcgccgtg accggggctt atgacacaat ccctcaggat    2220
cggctgactg aagtgatcgc ctccatcatt aagccacaga atacctactg cgtcgtggaga   2280
tatgctgtgg tcaggcgcgc tgcacacggc catgtgagga gagcttcaa cgccacgtc    2340
agcacactga ctgatctgca gccctacatg agacagttcg tggctcatct gcaggagacc    2400
agccctctga gggacgcagt ggtcatcgaa cagtcctcca gtctgaacga ggcatcaagc    2460
gggctgttcg atgtctttct gcggttcgtg tgccaccatg ccgtcagaat tggaggcaaa    2520
tcttacgtgc agtgtcaggg catccccag ggcagcattc tgtctaccct gctgtgcagc    2580
ctgtgctatg gcgacatgga aaataagctg tttgccggaa tccgacggga tggcctgctg    2640
ctgagactgg tggccgcttt tctgctggtc actccacacc tgacccatgc caaagctttc    2700
ctgcgcacac tggtccgagg ggtgccagag tacggatgcg tggtcaacct gaggaagacc    2760
gtggtcaatt tccagtgga agacgaggcc ctgggcggca cagcatttgt ccagctgcca    2820
gcacacggac tgttcccatg tgtggactg ctgctggaca cccgcacact ggaggtgcag    2880
tccgattact cctcttatgc ccggacaagc atcagagctt ccctgacttt taacagagac    2940
ttcaaggccg ggaggaatat gagaaggaaa ctgtttggcg tgctgcgcct gaagtgccat    3000
tccctgttcc tgtatctgca ggtgaactct ctgcagactg tctgtaccaa cgtgtacaaa    3060
atttttctgc tgcaggccta tcggttccac gcttgcgtgc tgcagctgcc attccatcag    3120
caggtcagga agaccccac cttctttctg cgcgtgatct ctgatacagc tagtctgtgc    3180
tactcaattc tgaaggccaa aaatgctggc atgagcctgg gagcaaaagg agcagcagga    3240
ccatttcctt ccgaggctgc acagtggctg tgccaccagg cattcctgct gaagctggcc    3300
cgacatcggg tgacatatag gtgcctgctg ggcgcactgc gaacagcaca gactcagctg    3360
tgcagaaagc tgcccgggc cactctggct gccctgaag ccgctgccga ccctgccctg    3420
acctccgatt tcaagactat tctggac                                      3447

SEQ ID NO: 18           moltype = AA   length = 1149
FEATURE                 Location/Qualifiers
source                  1..1149
                        mol_type = protein
                        organism = synthetic construct
SEQUENCE: 18
MDWTWILFLV AAATRVHSPR APRCRAVRSL LRSRYREVLP LATFVRRLGP QGRRLVQRGD     60
PAAFRALVAQ CLVCVPWDAR PPPAAPSFRQ VSCLKELVAR VVQRLCERGA RNVLAFGFAL    120
LDGARGGPPE AFTTSVRSYL PNTVTDTLRG SGAWGLLLRR VGDDVLVHLL ARCALYVLVA    180
PSCAYQVCGP PLYDLGAATQ ARPPPHASGT RRGLGTEQAW NHSVREAGVP LGLPAPGARR    240
RRGSAGRSLP LAKRPRRGAA PEPERTPVGQ GSWAHPGRTR GPSDRGFCVV SPARPAEEAT    300
SLEGALSGTR HSHPSVGRQH HAGPPSTSRP PRPWDTPCPP VYAETKHFLY SSGDKEQLRP    360
SFLLSSLRPS LTGARRLVET IFLGSRPWMP GTPRRTPRLP QRYWQMRPLF LELLGNHAQC    420
PYGALLRTHC PLRAAVTPAA GVCAREKPQG SVAAPEEEDT DPRRLVQLLR QHSSPWQVYG    480
FLRACLRRLV PPGLWGSRHN ERRFLRNTKK FISLGKHAKL SLQELTWKMS VRDCAWLRRS    540
PGVGCVPAAE HRLREEILAK FLHWLMSVYV VELLRSFFYV TETTFQKNYL FFYRKSVWSK    600
LQSIGIRQHL KRVQLRELSE AEVRQHREAR PALLTSRLRF LPKPDGLRPI VNMDYVVGAR    660
TFRREKRAER LTSRVKTLFS VLNYERARRP GLLGASVLGL DDIHRAWRAF VLRVRAQDPP    720
PELYFVKVAV TGAYDTIPQD RLTEVIASII KPQNTYCVRR VVRRAAHG HVRKSFKRHV    780
STLTDLQPYM RQFVAHLQET SPLRDAVVIE QSSSLNEASS GLFDVFLRFV CHHAVRIGGK    840
SYVQCQGIPQ GSILSTLLCS LCYGDMENKL FAGIRRDGLL LRLVAAFLLV TPHLTHAKAF    900
LRTLVRGVPE YGCVVNLRKT VVNFPVEDEA LGGTAFVQLP AHGLFPWCGL LLDTRTLEVQ    960
SDYSSYARTS IRASLTFNRG FKAGRNMRRK LFGVLRLKCH SLFLYLQVNS LQTVCTNVYK    1020
IFLLQAYRFH ACVLQLPFHQ QVRKNPTFFL RVISDTASLC YSILKAKNAG MSLGAKGAAG    1080
PFPSEAAQWL CHQAFLLKLA RHRVTYRCLL GALRTAQTQL CRKLPGATLA ALEAAADPAL    1140
TSDFKTILD                                                           1149

SEQ ID NO: 19           moltype = DNA   length = 3399
FEATURE                 Location/Qualifiers
source                  1..3399
                        mol_type = other DNA
                        organism = synthetic construct
SEQUENCE: 19
cctagagccc cacggtgtag agcagtccgc agcctgctgc gcagccgata ccggaagtg      60
ctgcctctgg ccacctttgt ccggagactg gaccacagg gcaggcgcct ggtgcagcgc    120
ggcgaccccg cagcttttcg agcactggtg gcacagtgcc tggtgtgcgt gccatgggat    180
gcacggcccc ctccagcagc cctagcttt gacaggtgt cctgcctgaa agaactggtc    240
gcaaggggtg tccagcggc gtgcgagaga ggcgccagca acgtgctggc attctggcttt    300
gcactgctga acggagctag gggcgggccc cctgaggcat tcaccacaag cgtgcgctcc    360
tacctgccaa atacagtcac tgataccctg cgaggctccg gagcatgggg actgctgctg    420
cgacgggtgg gggacgatgt gctggtccac ctgctggcta atgcgcact gtatgtgctg    480
gtcgctcccc cttgcgcata ccaggtgtgc ggaccacccc tgtatgacct gggcgctgca    540
acccaggcaa gacctccacc ccacgcctct ggcactagaa ggggactggg cacggaacag    600
```

```
gcatggaacc atagtgtcag ggaggcagga gtgccactgg gactgccagc acctggggct    660
cgccgacgga gagggagtgc cggacggtca ctgccactgg ctaagagacc aaggcgcgga    720
gccgctccag aaccagagag acacctgtg ggacagggaa gctgggcaca ccctggaaga    780
actaggggc caagtgatag gggcttctgc gtggtctcac cagcacgacc agcagaggaa    840
gctacttctc tggagggagc tctgagtggc acccggcact ctcatcctag tgtgggaaga    900
cagcaccatg caggccctcc aagcaccagc cggcctcccc ggccatggga cactccttgg    960
ccacccgtgt acgctgaaac caaacacttt ctgtatagct ccggagataa ggagcagctg   1020
cggccctctt tcctgctgtc tagtctgaga cctagtctga ccggagcacg acggctggtg   1080
gaaacaatct ttctggggtc ccgcccttgg atgccagaca ccccccagaag gacacctgga   1140
ctgccacagc ggtactggca gatgcggcca ctgttcctgg agctgctgga caatcacgt   1200
cagtgcccct atgggcact gctgcgaaca cattgtcctc tgcgggcagc cgtgactcca   1260
gctgcaggag tctgcgccag ggaaaagcca cagggcagcg tggcagctcc tgaggaagag   1320
gacaccgatc cacgccgact ggtgcagctg ctgagacagc actcaagccc ctggcaggtg   1380
tacggatttc tgaggcgctg tctgcggaga ctggtgcctc caggactgtg ggggtccagg   1440
cacaacgaaa ggcgctttct gcgcaatact aagaaattca tcagcctggg caagcatgct   1500
aaaactgtccc tgcaggagct gacctggaaa atgagtgtgc gcgactgcgc atggctgcga   1560
cggtcaccag gagtcgggtg cgtgcctgca gccgagcacc gctgcgaga agagattctg   1620
gccaagtttc tgcattggct gatgtcagtg tacgtggtcg aactgctgcg gagcttcttt   1680
tatgtgacag agactacctt ccagaaaaac tacctgttct tttatcgcaa gtcagtgtgg   1740
agcaaactgc agtcaatcgg cattcggcag cacctgaaga gagtgcagct gagggaactg   1800
agtgaagccg aggtccggca gcatagagag gcaaggcctg ccctgctgac ctcccggctg   1860
agattcctgc ctaagccaga cgggctgaga ccaatcgtga acatggatta cgtggtcgga   1920
gcacggacct tccggaggga aaaacgcgct gagcgactga catcccgcgt gaagactctg   1980
ttctctgtcc tgaattatga gcgagctcgc cgacccggac tgctgggagc atctgtgctg   2040
ggactggacg atattcaccg ggcttggaga gcatttgtcc tgagggtgcg cgcacaggac   2100
cctccccccag aactgtactt cgtgaaagtc gccgtgaccg gggcttatga cacaatccct   2160
caggatcggc tgactgaagt gatcgcctcc atcattaagc cacagaatac ctactgcgtg   2220
cggagatatg ctgtggtcag gcgcgctgca cacggccatg tgaggaagag cttcaagcgc   2280
cacgtcagca cactgactga tctgcagccc tacatggaca gttcgtggc tcatctgcag   2340
gagaccgcc ctctgagga cgcagtggtc atcgaacagt cctctagtct gaacgaggca   2400
tcaagcgggc tgttcgatgt ctttctgcgg ttcgtgtgcc accatgccgt cagaattgga   2460
ggcaaatctt acgtgcagtg tcagggcatc ccccagggca gcattctgtc taccctgctg   2520
tgcagcctgt gctatggcga catggaaaat aagctgtttg ccggaatccg acgggatggc   2580
ctgctgctga gactggtggc cgcttttctg ctggcactc cacacctgac ccatgccaaa   2640
gctttcctgc gcacactggt ccgagggggtg ccagagtacg gatgcgtggt caacctgagg   2700
aagaccgtgg tcaatttccc agtggaagac gaggccctgg gcggcacagc atttgtccag   2760
ctgccagcac acggactgtt cccatggtgt ggactgctgc tggacacccg cacactggag   2820
gtgcagtccg attactcctc ttatgcccgg acaagcatca gagcttccct gactttaac   2880
agaggcttca aggcccggag gaatatgaga aggaaactgt ttggcgtgct gcgcctgaag   2940
tgccattccc tgttcctgta tctgcaggtg aactctctgc agactgtctg taccaacgtg   3000
tacaaaattt ttctgctgca ggcctatcgg ttccacgctt gcgtgctgca gctgccattc   3060
catcagcagg tcaggaagaa cccccacctc ttcctgcgcg tgatctctga tacagctagt   3120
ctgtgctact caattctgaa ggccaaaaat gctggcatga gcctgggaag aaaaggagga   3180
gcaggaccat ttccttccga ggctgcacag tggctgtgcc accaggcatt cctgctgaag   3240
ctggcccgac atcgggtgac atataggtgc ctgctgggcg cactgcgaac agcacagact   3300
cagctgtgca gaaagctgcc cggggccact ctggctgccc tggaagccgc tgccgaccct   3360
gccctgacct ccgatttcaa gactattctg gactgataa                          3399

SEQ ID NO: 20           moltype = AA  length = 1131
FEATURE                 Location/Qualifiers
source                  1..1131
                        mol_type = protein
                        organism = synthetic construct
SEQUENCE: 20
PRAPRCRAVR SLLRSRYREV LPLATFVRRL GPQGRRLVQR GDPAAFRALV AQCLVCVPWD     60
ARPPPAAPSF RQVSCLKELV ARVVQRLCER GARNVLAFGF ALLDGARGGP PEAFTTSVRS    120
YLPNTVTDTL RGSGAWGLLL RRVGDDVLVH LLARCALYVL VAPSCAYQVC GPPLYDLGAA    180
TQARPPPHAS GTRRGLGTEQ AWNHSVREAG VPLGLPAPGA RRRRGSAGRS LPLAKRPRRG    240
AAPEPERTPV GQGSWAHPGR TRGPSDRGFC VVSPARPAEE ATSLEGALSG TRHSHPSVGR    300
QHHAGPPSTS RPPRPWDTPC PPVYAETKHF LYSSGDKEQL RPSFLLSSLR PSLTGARRLV    360
ETIFLGSRPW MPGTPRRTPR LPQRYWQMRP LFLELLGNHA QCPYGALLRT HCPLRAAVTP    420
AAGVCAREKP QGSVAAPEEE DTDPRRLVQL LRQHSSPWQV YGFLRACLRR LVPPGLWGSR    480
HNERRFLRNT KKFISLGKHA KLSLQELTWK MSVRDCAWLR RSPGVGCVPA AEHRLREEIL    540
AKFLHWLMSV YVVELLRSFF YVTETTFQKN YLFFYRKSVW SKLQSIGIRQ HLKRVQLREL    600
SEAEVRQHRE ARPALLTSRL RFLPKPDGLR PIVNMDYVVG ARTFRREKRA ERLTSRVKTL    660
FSVLNYERAR RPGLLGASVL GLDDIHRAWR AFVLRVRAQD PPPELYFVKV AVTGAYDTIP    720
QDRLTEVIAS IIKPQNTYCV RRYAVVRRAA HGHVRKSFKR HVSTLTDLQP YMRQFVAHLQ    780
ETSPLRDAVV IEQSSSLNEA SSGLFDVFLR FVCHHAVRIG GKSYVQCQGI PQGSILSTLL    840
CSLCYGDMEN KLFAGIRRDG LLLRLVAAFL LVTPHLTHAK AFLRTLVRGV PEYGCVVNLR    900
KTVVNFPVED EALGGTAFVQ LPAHGLFPWC GLLLDTRTLE VQSDYSSYAR TSIRASLTFN    960
RGFKAGRNMR RKLFGVLRLK CHSLFLYLQV NSLQTVCTNV YKIFLLQAYR FHACVLQLPF   1020
HQQVRKNPTF FLRVISDTAS LCYSILKAKN AGMSLGAKGA AGPFPSEAAQ WLCHQAFLLK   1080
LARHRVTYRC LLGALRTAQT QLCRKLPGAT LAALEAAADP ALTSDFKTIL D            1131

SEQ ID NO: 21           moltype = DNA  length = 2307
FEATURE                 Location/Qualifiers
source                  1..2307
                        mol_type = unassigned DNA
                        organism = unidentified
```

```
SEQUENCE: 21
atggactgga catgattct  gttcctggtc gccgccgcaa ctcgcgtgca ttcctggaac   60
gcactgcatg agactgattc tgctgtcgca ctgggacgga gaccccgtg  gctgtgcgct  120
ggagcactgg tgctggccgg cgggggattc tgctgggat  tcctgtttgg ctggtttatc  180
aaaagctcca gcgaggctac caatattacc cctaagcaca ataagaaagc attcctggat  240
gaactgaaag ccgagaacat caagaaattc ctgtacaact tcacaagaat tccacatctg  300
gctggcactg agcagaactt ccagctggca aaacagatcc agagtcagtg gaaggaattt  360
gggctggact cagtggagct gacccactac gatgtcctgc tgtcctatcc aaataagact  420
catcccaact acatctctat cattaacgac acggaaatg  agattttcaa cacctctctg  480
tttgaacccc ctccacccgg ctatgagaat gtcagtgacg tggtccctcc attctcagcc  540
ttcagccccc aggggatgcc tgagggagat ctggtgtacg tcaattatgc tagaacagaa  600
gacttcttta gctggagag  ggatatgaaa atcaactgtt ccggcaagat cgtgattgcc  660
cggtacggga aggtgttcag aggaaataag gtcaaaaacg ctcagctggc cggagctacc  720
ggcgtgatcc tgtacagcga ccccgctgat tattttcac  ctggcgtgaa gtcctatcca  780
gacggatgga atctgcccgg cgggggagtg cagaggggaa acatcctgaa cctgaatgga  840
gccggcgatc ctctgactcc aggataccc  gccaacgaat acgcttatcg ccgggg aatt  900
gcagaggccg tgggcctgcc tagcatccca gtccatccca ttggctatta cgatgcccag  960
aagctgctgg agaaaatggg cgggagcgct cccctgact  ctagttggaa ggctccctg  1020
aaagtgcctt acaatgtcgg gccaggattc actgggaact tttctaccca gaaggtgaaa  1080
atgcacatcc atagtaccag cgaggtgaca cgaatctaca acgtcattgg caccctgaga  1140
ggcgccgtga gcctgatcg  ctatgtcatt ctgggaggcc acagagactc atgggtgttc  1200
ggggaatcg  atccacagag cggagcagct gtggtccatg aaattgtgcg cagctttggg  1260
accctgaaga aagagggatg gcgacccagg cgcacaatcc tgttcgcatc ctgggacgcc  1320
gaggaatttg gctgctggg  cagcacagaa tgggccgagg aaaattctcg cctgctgcag  1380
gagcgagggg tggcttacat caatgcagac tcaagcattg aaggaaacta ccctgcgcg  1440
gtggattgca caccctgat  gtacagtctg gtctataacg tgacaaagga gctgaaatca  1500
cctgacgagg gcttcgaagg gaaaagcctg tacgaatcct ggactgagaa gagcccatcc  1560
cccgaattca gcggcatgcc taggatctct aagctgggca gtgggaacga ttttgaggtg  1620
ttctttcagc gcctgggaat tgcctctggc cgagctcggt acacaaaaaa ttgggagact  1680
aacaagttct cctcttaccc actgtatcac agcgtgtacg agacttatga actggtcgag  1740
aaattctacg accccacttt taagtatcat ctgaccgtgg cacaggtcag ggcgcgggatg  1800
gtgttcgaac tggccaatag catcgtcctg ccatttgact gtcgagatta cgctgtggtc  1860
ctgcggaagt acgcagacaa gatctataac atctccatga agcaccccca ggagatgaag  1920
gcctattctg tgagtttga  ttccctgttt tctgccgtca aaaatttcac cgaaatcgtt  1980
agtaagtttt cagagcgcct gcaggacctg gataagtcca atcccatcct gctgcgcgatt  2040
atgaacgatc agctgatgtt cctggaaaga gccttatcg  acccctctgg cctgcctgat  2100
agaccattct acaggcacgt gatctacgca cctagttcac ataacaagta cgccggcgag  2160
tctttcccag ggatctatga cgctctgttt gatattgaat caaaggtgga ccccagcaaa  2220
gcatgggggcg aggtcaagag acagatcagc attgcagcct tacagtgca  ggccgccgcc  2280
gaaaccctgt ccgaagtcgc ttgataa                                      2307

SEQ ID NO: 22          moltype = DNA length = 660
FEATURE                Location/Qualifiers
source                 1..660
                       mol_type = unassigned DNA
                       organism = unidentified
SEQUENCE: 22
atgtgtccag cgcgcagcct cctccttgtg gctaccctgg tcctcctgga ccacctcagt   60
ttggccagaa acctccccgt ggccactcca gacccaggaa tgttcccatg ccttcaccac  120
tcccaaaacc tgctgagggc cgtcagcaac atgctccaga aggccagaca aactctagaa  180
ttttacccct gcacttctga agagattgat catgaagata tcacaaaaga taaaaccagc  240
acagtggagg cctgtttacc attgaattac caagaatg   agagttgcct aaattccaga  300
gagacctctt tcataactaa tgggagttgc ctggcctcca gaaagacctc ttttatgatg  360
gccctgtgcc ttagtagtat ttatgaagac ttgaagatgt accaggtgga gttcaagacc  420
atgaatgcaa agcttctgat ggatcctaag aggcagatct ttctagatca aaacatgctg  480
gcagttattg atgagctgat gcaggccctg aatttcaaca gtgagactgt gccacaaaaa  540
tcctcccttg aagaaccgga ttttataaaa actaaaatca agctctgcat acttcttcat  600
gctttcagaa tcgggcagt  gactattgat agagtgatga gctatctgaa tgcttcctaa  660

SEQ ID NO: 23          moltype = AA length = 219
FEATURE                Location/Qualifiers
source                 1..219
                       mol_type = protein
                       organism = unidentified
SEQUENCE: 23
MCPARSLLLV ATLVLLDHLS LARNLPVATP DPGMFPCLHH SQNLLRAVSN MLQKARQTLE   60
FYPCTSEEID HEDITKDKTS TVEACLPLEL TKNESCLNSR ETSFITNGSC LASRKTSFMM  120
ALCLSSIYED LKMYQVEFKT MNAKLLMDPK RQIFLDQNML AVIDELMQAL NFNSETVPQK  180
SSLEEPDFYK TKIKLCILLH AFRIRAVTID RVMSYLNAS                         219

SEQ ID NO: 24          moltype = DNA length = 987
FEATURE                Location/Qualifiers
source                 1..987
                       mol_type = unassigned DNA
                       organism = unidentified
SEQUENCE: 24
atgtgtcacc agcagttggt catctcttgg ttttccctgg ttttctggc  atctcccctc   60
gtggccatat gggaactgaa gaaagatgtt tatgtctag  aattggattg gtatccggat  120
gcccctggag aaatggtggt cctcacctgt gacacccctg aagaagatgg tatcacctgg  180
```

```
accttggacc agagcagtga ggtcttaggc tctggcaaaa ccctgaccat ccaagtcaaa    240
gagtttggag atgctggcca gtacacctgt cacaaaggag gcgaggttct aagccattcg    300
ctcctgctgc ttcacaaaaa ggaagatgga atttggtcca ctgatatttt aaaggaccag    360
aaagaaccca aaaataagac ctttctaaga tgcgaggcca agaattattc tggacgtttc    420
acctgctggt ggctgacgac aatcagtact gatttgcat tcagtgtcaa aagcagcaga     480
ggctcttctg acccccaagg ggtgacgtgc ggagctgcta cactctctgc agagagagtc    540
agagggaca caaggagta tgagtactca gtggagtgcc aggaggacag tgcctgccca     600
gctgctgagg agagtctgcc cattgaggtc atggtggatg ccgttcacaa gctcaagtat    660
gaaaactaca ccagcagctt cttcatcagg gacatcatca aacctgaccc acccaagaac    720
ttgcagctga agccattaaa gaattctcag caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttag                                       987

SEQ ID NO: 25          moltype = AA  length = 328
FEATURE                Location/Qualifiers
source                 1..328
                       mol_type = protein
                       organism = unidentified
SEQUENCE: 25
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCS                                      328

SEQ ID NO: 26          moltype = AA  length = 418
FEATURE                Location/Qualifiers
source                 1..418
                       mol_type = protein
                       organism = unidentified
SEQUENCE: 26
GSDVRDLNAL LPAVPSLPGG GGCALPVSGA AQWAPVLDFA PPAAPYGSLG GPHSFIKQEP     60
SWGGADPHEE QCLSAFTVHF SGQFTGTAGA CRYGPFGAPP PSQAPSGQAR MFPNAPYLPN    120
CLESQPAIRN QGYSTVAFDG TPSYGHTPSH HAAQFPNHSF KHEDPMGQQG SLGEQQYSVP    180
PPVYGCHTPT DSCTGSQALL LRTPYNSDNL YQMTSQLECM TWNQMNLGST LKGHATGYES    240
DNHTTPMLYS CGAQYRIHTH GVFRGIQDVR RVPGVAPTIV RSASETNEKR PFMGAYPGGN    300
KRYFKLSHLQ MGSRKGTGEK PYQGDFKDGE RRFSRSDQLK RGQRRGTGVK PFQCKTCQRK    360
FSRSDHLKTH TRTHTGKTSE KPFSCRWPSC QKKFARSDEL VRHHNMHQRN MTKLQLAL     418

SEQ ID NO: 27          moltype = DNA  length = 1260
FEATURE                Location/Qualifiers
source                 1..1260
                       mol_type = unassigned DNA
                       organism = unidentified
SEQUENCE: 27
gggagtgatg tgagagacct gaacgccctg ctgccagcag tgccatccct gcctggcggg     60
ggaggctgcg ctctgccagt ctctggagca gctcagtggg ctcccgtgct ggactttgca    120
ccccctgcag ccccttacgg aagtctgggc ggcccacact cattcatcaa acaggagcca    180
agctggggcg gggcagatcc tcatgaggaa cagtgcctgt cagccttcac agtccacttt    240
agcgggcagt tcactggaac cgcaggagct tgtagatacg gacccttggg agcaccaccc    300
ccttcccagg caccttctgg acaggcacgc atgttcccaa acgctcccta tctgcctaat    360
tgtctggaaa gccagcccgc tattaggaac cagggctact ccacagtgge atttgacggg    420
actcctagct atggacatac ccatcccac catgctgcac agtttcctaa tcactccttc    480
aagcatgagg accccatggg acagcagggg tccctgggag aacagcagta ctctgtgccc    540
cctcccgtgt acggatgcca cacaccaact gacagttgta caggctcaca ggccctgctg    600
ctgcgaactc catacaacag tgataatctg tatcagatga cctcacagct ggagtgcatg    660
acatggaacc agatgaatct gggcagcaca ctgaaaggcc atgccactgg gtacgaatct    720
gacaaccaca ccacacctat gctgtacagt tgtggagccc agtatagaat ccacactcat    780
ggagtcttca gaggcattca ggatgtgcgg agagtcccag gagtggcacc aactatcgtg    840
cggagcgcct ccgagaccaa cgaaaagcgc ccctttatgg gcgcctaccc tggaggcaat    900
aagcggtatt tcaaactgtc tcacctgcag atgggggagta aaggggac ggagagaaa     960
ccttatcagg gcgactttaa agatgggaa aggcgcttct ctcgcagtga ccagctgaag   1020
cgaggacagc gacgaggaac cggggtgaag ccatttcagt gcaaaacatg tcagagaaag   1080
ttctcaagga gcgatcacct gaagacccat acaagaactc acaccggcaa gaccagcgag   1140
aaaccatttt cctgccgatg gccctcttgt cagaagaaat tcgcccgctc cgacgaactg   1200
gtccgacacc acaatatgca tcagagaaat atgacaaaac tgcagctggc tctgtgataa   1260

SEQ ID NO: 28          moltype = AA  length = 749
FEATURE                Location/Qualifiers
source                 1..749
                       mol_type = protein
                       organism = unidentified
SEQUENCE: 28
WNALHETDSA VALGRRPRWL CAGALVLAGG GFLLGFLFGW FIKSSSEATN ITPKHNKKAF     60
LDELKAENIK KFLYNFTRIP HLAGTEQNFQ LAKQIQSQWK EFGLDSVELT HYDVLLSYPN    120
KTHPNYISII NEDGNEIFNT SLFEPPPPGY ENVSDVVPPF SAFSPQGMPE GDLVYVNYAR    180
```

```
TEDFFKLERD MKINCSGKIV IARYGKVFRG NKVKNAQLAG ATGVILYSDP ADYFAPGVKS  240
YPDGWNLPGG GVQRGNILNL NGAGDPLTPG YPANEYAYRR GIAEAVGLPS IPVHPIGYYD  300
AQKLLEKMGG SAPPDSSWKG SLKVPYNVGP GFTGNFSTQK VKMHIHSTSE VTRIYNVIGT  360
LRGAVEPDRY VILGGHRDSW VFGGIDPQSG AAVVHEIVRS FGTLKKEGWR PRRTILFASW  420
DAEEFGLLGS TEWAAENSRL LQERGVAYIN ADSSIEGNYT LRVDCTPLMY SLVYNLTKEL  480
KSPDEGFEGK SLYESWTEKS PSPEFSGMPR ISKLGSGNDF EVFFQRLGIA SGRARYTKNW  540
ETNKFSSYPL YHSVYETYEL VEKFYDPTFK YHLTVAQVRG GMVFELANSI VLPFDCRDYA  600
VVLRKYADKI YNISMKHPQE MKAYSVSFDS LFSAVKNFTE IASKFSERLQ DLDKSNPILL  660
RIMNDQLMFL ERAFIDPLGL PDRPFYRHVI YAPSSHNKYA GESFPGIYDA LFDIESKVDP  720
SKAWGEVKRQ ISIAAFTVQA AAETLSEVA                                   749

SEQ ID NO: 29           moltype = DNA  length = 2253
FEATURE                 Location/Qualifiers
source                  1..2253
                        mol_type = unassigned DNA
                        organism = unidentified
SEQUENCE: 29
tggaacgcac tgcatgagac tgattctgct gtcgcactgg gacgagaccc ccggtggctg   60
tgcgctggag cactggtgct ggccggcggg ggattcctgc tgggattcct gtttggctgg  120
tttatcaaaa gctccagcga ggctaccaat attacccta agcacaataa gaaagcattc  180
ctggatgaac tgaaagccga aacatcaag aaattcctgt acaacttcac aagaattcca  240
catctggctg gcactgagca gaacttccag ctggcaaaac agatccagag tcagtggaag  300
gaatttgggc tggactcagt ggagctgacc cactacgatg tcctgctgtc ctataccaat  360
aagactcatc ccaactacat ctctatcatt aacgaagacg gaaatgagat tttcaacacc  420
tctctgtttg aaccccctcc acccggctat gagaatgtca gtgacgtggt ccctccattc  480
tcagccttca gccccaggg gatgcctgag ggagatctgg tgtacgtcaa ttatgctaga  540
acagaagact tctttaagct ggagagggat atgaaaatca actgttccgg caagatcgtg  600
attgcccggt acgggaaggt gttcagagga ataaggtcaa aaacgctca gctggccgga  660
gctaccggcg tgatcctgta cagcgacccc gctgattatt ttgcacctgg cgtgaagtcc  720
tatccagacg gatggaatct gccccggcgg ggagtgcaga ggggaaacat cctgaacctg  780
aatggagccg gcgatcctct gactccagga taccccgcca acgaatacgc ttatcgccgg  840
ggaattgcag aggccgtggg cctgcctagc atcccagtcc atccattgg ctattacgat  900
gcccagaagc tgctggagaa aatgggcggg agcgctcccc ctgactctag ttggaagggc  960
tccctgaaag tgccttacaa tgtcgggcca ggattcactg gaactttttc tacccagaag 1020
gtgaaaatgc acatccatag taccagcgag gtgacacgaa tctacaacgt cattggcacc 1080
ctgagaggcg ccgtggagcc tgatcgctat gtcattctgg gaggccacag agactcatgg 1140
gtgttcgggg gaatcgatcc acagagcgga gcagctgtgg tccatgaaat tgtcgcgagc 1200
tttgggaccc tgaagaaaga gggatgggga cccaggcgca caatcctgtt cgcatcctgg 1260
gacgccgagg aatttgggct gctgggcagc acagaatggg ccgaggaaaa ttctcgcctg 1320
ctgcaggagc gaggggtggc ttacatcaat gcagactcaa gcattgaagg aaactatacc 1380
ctgcgggtgg attgcacacc cctgatgtac agtctggtct ataacctgac aaaggagctg 1440
aaaatcacctg acgagggctt cgaagggaaa gcctgtacg aatcctggac tgagaagagc 1500
ccatcccccg aattcagcgg catgcctagg atctctaagc tgggcagtgg aacgattttt 1560
gaggtgttct ttcagcgcct gggaattgcc tctggccgag ctcggtacac aaaaaattgg 1620
gagactaaca agttctcctc ttacccactg tatcacagcg tgtacgagac ttatgaactg 1680
gtcgagaaat tctacgaccc cacttttaag tatcatctga ccgtggcaca ggtcaggggc 1740
gggatggtgt tcgaactggc caatagcatc gtcctgccat ttgactgtcg agattacgct 1800
gtggtcctgc ggaagtacgc agacaagatc tataacatct ccatgaagca ccccagag 1860
atgaaggcct attctgtgag tttcgattcc ctgttttctg ccgtcaaaaa tttcaccgaa 1920
atcgctagta agttttcaga gcgcctgcag gacctggata gtccaatcc catcctgctg 1980
cggattatga acgatcagct gatgttcctg gaaagagcct ttatcgaccc tctgggcctg 2040
cctgatagac cattctacag gcacgtgatc tacgcaccta gttcacataa caagtacgcc 2100
ggcgagtctt tcccaggdat ctatgacgct ctgtttgata ttgaatcaaa ggtgacccc 2160
agcaaagcat ggggcgaggt caagagacag atcagcattg cagcctttac agtgcaggcc 2220
gccgccgaaa ccctgtccga agtcgcttga taa                             2253

SEQ ID NO: 30           moltype = RNA  length = 21
FEATURE                 Location/Qualifiers
source                  1..21
                        mol_type = genomic RNA
                        organism = Homo sapiens
SEQUENCE: 30
gcccctgggc ctatcctaga a                                            21

SEQ ID NO: 31           moltype = RNA  length = 22
FEATURE                 Location/Qualifiers
source                  1..22
                        mol_type = genomic RNA
                        organism = Homo sapiens
SEQUENCE: 31
aaaaccgtct agttacagtt gt                                           22
```

COMBINATION THERAPY TO TREAT BRAIN CANCER

CROSS-REFERENCE TO RELATED APPLICATIONS

This application claims priority to U.S. Provisional Patent Application No. 63/232,966, filed Aug. 13, 2021, the disclosure of which is incorporated by reference in its entirety for all purposes.

SEQUENCE LISTING

The instant application contains a Sequence Listing which is being submitted herewith electronically in ASCII format and is hereby incorporated by reference in its entirety. Said ASCII copy, created on Nov. 2, 2022, is named 104409_000727_SL.txt and is 54,099 bytes in size.

TECHNICAL FIELD

The present invention relates to combination therapies and methods for treating brain cancer.

BACKGROUND

Despite advances in therapy, glioblastoma (GBM) remains one of the deadliest cancers. The current standard treatment for GBM is surgery, followed by concurrent radiation therapy (RT) and temozolomide (TMZ) chemotherapy administered daily during RT and then for 6-12 maintenance (adjuvant) cycles following the completion of RT for select patients [Stupp R, Mason W P, van den Bent M J, et al. Radiotherapy plus concomitant and adjuvant temozolomide for glioblastoma. N Engl J Med 2005, 352: 987-996].

Checkpoint inhibitors, such as programmed cell death-1 (PD-1) inhibitors, have increased response rates in many cancers, but have not yet shown clinical benefit in GBM.

Accordingly, a need exists for the identification and development of methods for the treatment and prognosis of GBM to facilitate clinical management and progression of disease.

SUMMARY

Provided herein are methods of treating brain cancer in a subject, comprising: (a) measuring an expression level of a miR-331-3p miRNA comprising SEQ ID NO: 30 or isomiRs thereof and a miR-1537-3p miRNA comprising SEQ ID NO: 31 or isomiRs thereof in a biological sample from a subject who has brain cancer; and (b) administering interleukin-12 (IL-12); an immunogenic composition of human telomerase reverse transcriptase (hTERT), Wilms Tumor-1 (WT-1), and prostate specific membrane antigen (PSMA); and an anti-programmed cell death receptor 1 (PD-1) antibody to said subject if the subject has an increased expression level of the miR-331-3p miRNA or isomiRs thereof and the miR-1537-3p miRNA or isomiRs thereof relative to a control population of subjects. In certain embodiments, the presence of the miRNA is determined by RNA sequencing. In certain embodiments, the biological sample is a plasma sample. In certain embodiments, the biological sample is taken from the subject prior to administration of the IL-12; an immunogenic composition of hTERT, WT-1, and PSMA; and the anti-PD-1 antibody.

Also provided herein are methods of treating brain cancer in a subject, comprising: (a) measuring an expression level of a miR-331-3p miRNA comprising SEQ ID NO: 30 or isomiRs thereof and a miR-1537-3p miRNA comprising SEQ ID NO: 31 or isomiRs thereof in a biological sample from a subject who has brain cancer; and (b) administering interleukin-12 (IL-12); an immunogenic composition of human telomerase reverse transcriptase (hTERT), Wilms Tumor-1 (WT-1), and prostate specific membrane antigen (PSMA); and an anti-programmed cell death receptor 1 (PD-1) antibody to said subject if the subject has an increased expression level of the miR-331-3p miRNA or isomiRs thereof and the miR-1537-3p miRNA or isomiRs thereof relative to a control population of subjects. In certain embodiments, the biological sample is a primary tumor sample. In certain embodiments, the biological sample is taken from the subject prior to administration of the IL-12; an immunogenic composition of hTERT, WT-1, and PSMA; and the anti-PD-1 antibody.

In certain embodiments, administration of IL-12; an immunogenic composition of hTERT, WT-1, and PSMA; and an anti-PD-1 antibody results in survival at 18 months post administration. In certain embodiments, the control population of subjects is deceased at 18 months post administration of IL-12; an immunogenic composition of hTERT, WT-1, and PSMA; and an anti-PD-1 antibody. In certain embodiments, the subject has an unmethylated MGMT gene promoter.

In certain embodiments, IL-12 is encoded by a DNA plasmid, for example, INO-9012 or a biosimilar or bioequivalent thereof. In certain embodiments, hTERT, WT-1, and PSMA are encoded by one or more DNA plasmids, for example, INO-5401 or a biosimilar or bioequivalent thereof. In certain embodiments, the anti-PD-1 antibody is cemiplimab or a biosimilar or bioequivalent thereof. In certain embodiments, the methods further comprise administering radiation therapy and/or a chemotherapeutic agent, for example, temozolomide or a bioequivalent thereof.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the thereof; however, the methods are not limited to the specific embodiments disclosed. In the drawings:

FIG. 2A and FIG. 2B show the study population demographics for the example for the 18-month (FIG. 2A) and 42-month (FIG. 2B) analysis timepoints.

FIG. 3 shows representative MRI Images from two patients demonstrating increase in MRI signal at timepoints following first dose of INO-5401+INO-9012 and cemiplimab-rwlc, suggestive of edema or tumor. Biopsy on several patients shows treatment-related changes with necrosis and mixed inflammation; absence of mitotic activity; and no evidence of viable tumor. The subject represented by the MRI images in the lower panel showed evidence of disease progression at Week 9 but resolution at Week 21. Subjects with similar findings on MRI who were resected showed only immune infiltrate with an absence of viable tumor.

FIG. 4 demonstrates ELISpot results supporting the combination of INO-5401 and cemiplimab-rwlc as immunogenic-with IFN-g magnitudes above baseline to all 3 antigens in 5/11 subjects and to at least one antigen in 9 subjects obtained at the 12-month data cut-off.

FIG. 5A shows the frequencies of live, antigen specific, activated (CD38+) CD3+CD8+ T cells with lytic potential (expressing Granzyme A, Perforin) from before treatment (pre) and the highest magnitude (peak) after treatment with INO-5401 and cemiplimab-rwlc. Each subject is represented by an open circle, bars represent the mean. The difference from pre to peak, delta, is shown for each antigen graph as well as together for 8 subjects assayed (FIG. 5B) and for the 5 subjects with sample available to week 12 (FIG. 5C). INO-5401 is the sum of WT1, PSMA and hTERT. Box plots extend from the 25th to 75th percentile, with a horizontal line at the median, and "+" at the mean.

FIG. 6 shows the visual representation of the Kaplan-Meier estimator of the progression-free survival at six months (PFS6) for Cohort A, patients with the O6- methylguanine methyltransferase gene promoter unmethylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 7 shows the visual representation of the Kaplan-Meier estimator of the progression-free survival at six months (PFS6) for Cohort B, patients with the O6- methylguanine methyltransferase gene promoter methylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 8 shows the visual representation of the Kaplan-Meier estimator of the progression-free survival at six months (PFS6) for Cohort A and Cohort B, patients with the O6-methylguanine methyltransferase gene promoter unmethylated or methylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 9 shows the tabular representation of the Kaplan-Meier estimator of the progression-free survival at six months (PFS6) for Cohort A, Cohort B, and both cohorts combined. The total number of subjects per cohort, number of events, estimation of the event (PFS6), and the 95% confidence interval (CI) in which the numerical estimate of the event (PFS6) exists are all provided.

FIG. 12 shows the visual representation of the Kaplan-Meier estimator of the overall survival probability over twelve months for Cohorts A+B combined. The stepwise curve shows the probability of surviving up to and beyond a specific time point. The survival probability is represented numerically on the y-axis, and survival time in days on the x-axis.

FIG. 13 shows the efficacy data of the overall survival at 12 months and 18 months for Cohort A, for Cohort B, and combined. The figure shows the total number of subjects who were reported alive at 12 months and at 18 months. The total number of subjects, estimation of the event (OS12 or OS18), and the 95% confidence interval (CI) in which the numerical estimate of the event (OS12 or OS18) exists are all provided. The 95% CI were calculated using the exact Clopper-Pearson method.

FIG. 14 illustrates all Adverse Events as defined by the clinical study protocol ≥NCI CTCAE Grade 3 from the example at the 18-month analysis timepoint.

FIG. 15 illustrates Immune Related Adverse Events as defined by the clinical study protocol from the example at the 18-month analysis timepoint.

DETAILED DESCRIPTION OF ILLUSTRATIVE EMBODIMENTS

Figure 1:
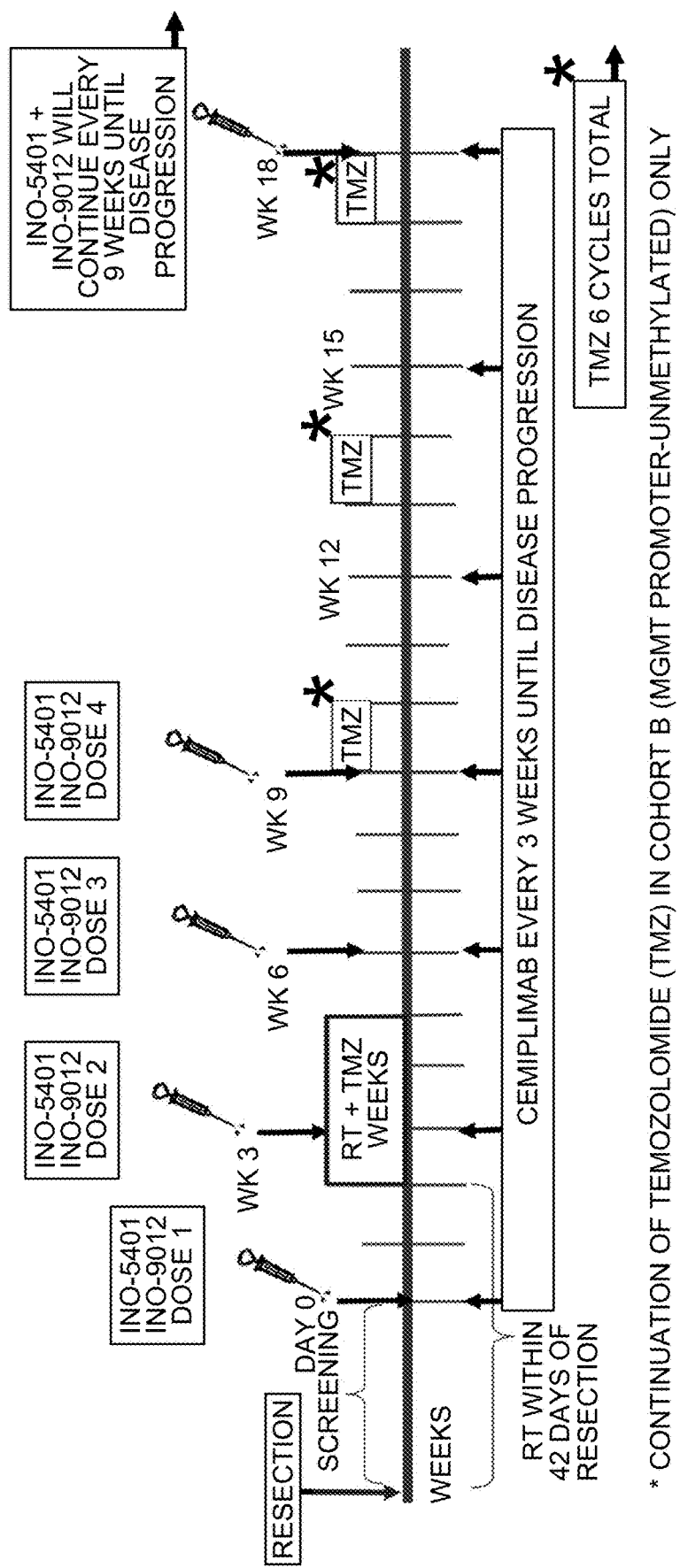
FIG. 1 illustrates the study design for the examples.

The disclosed nucleic acid molecules, proteins, vaccines, and methods may be understood more readily by reference to the following detailed description taken in connection with the accompanying figures, which form a part of this disclosure. It is to be understood that the disclosed nucleic acid molecules, proteins, vaccines, and methods are not limited to the specific nucleic acid molecules, proteins, vaccines, and methods described and/or shown herein, and that the terminology used herein is for the purpose of describing particular embodiments by way of example only and is not intended to be limiting of the claimed nucleic acid molecules, proteins, vaccines, and methods.

Unless specifically stated otherwise, any description as to a possible mechanism or mode of action or reason for improvement is meant to be illustrative only, and the disclosed nucleic acid molecules, proteins, vaccines, and methods are not to be constrained by the correctness or incorrectness of any such suggested mechanism or mode of action or reason for improvement.

For recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

It is to be appreciated that certain features of the disclosed nucleic acid molecules, proteins, vaccines, and methods which are, for clarity, described herein in the context of separate embodiments, may also be provided in combination in a single embodiment.

Conversely, various features of the disclosed nucleic acid molecules, proteins, vaccines, and methods that are, for brevity, described in the context of a single embodiment, may also be provided separately or in any subcombination.

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

Certain Terminology

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of," and "consisting essentially of" the embodiments or elements presented herein, whether explicitly set forth or not.

Some of the quantitative expressions given herein are not qualified with the term "about". It is understood that, whether the term "about" is used explicitly or not, every quantity given is intended to refer to the actual given value, and it is also meant to refer to the approximation to such given value that would reasonably be inferred based on the ordinary skill in the art, including approximations due to the experimental and/or measurement conditions for such value.

"Adjuvant" as used herein means any molecule added to the immunogenic compositions described herein to enhance the immunogenicity of the antigens encoded by the nucleic acid molecules and the encoding nucleic acid sequences described hereinafter.

"Biosimilar" (of an approved reference product/biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance.

The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the antibody (or antigen-binding portion thereof) may be identical to the human germline sequences or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3- CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-CH1; (ii) VH-CH2; (iii) VH-CH3; (iv) VH-CH1-CH2; (V) VH-CH1-CH2-CH3; VH-CH2-CH3; (vii) VH-CL; (Viii) VL-CH1; (ix) VL-CH2; (x) VL-CH3; (xi) VL-CH1-CH2; (xii) VL-CH2-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Immunogenic compositions comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acid sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

The term "therapeutically effective amount" refers to a therapeutically effective amount of a biologic, compound, or composition that can produce a therapeutic effect in a human subject. A therapeutically effective amount is an amount that can treat, ameliorate, or prevent an identified disease or condition, or to exhibit a detectable therapeutic effect. A therapeutically effective amount is an amount that results in one or more of: (a) a reduction in the severity or duration of a symptom or an indication of a cancer, e.g., glioblastoma; (b) inhibition of tumor growth, or an increase in tumor necrosis, tumor shrinkage and/or tumor disappearance; (c) delay in tumor growth and development; (d) inhibition of tumor metastasis; (e) prevention of recurrence of tumor growth; (f) increase in survival of a subject with a cancer; and/or (g) a reduction in the use or need for conventional anti-cancer therapy (e.g., reduced or eliminated use of chemotherapeutic or cytotoxic agents) as compared to an untreated subject or a subject administered the anti-cancer therapy as monotherapy. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

As used herein, "therapeutic effect" is a consequence of a medical treatment of any kind, the results of which are judged to be desirable and beneficial. This is true whether the result was expected, unexpected, or even an unintended consequence of the treatment. A therapeutic effect may also be an objectively identifiable improvement as noted by the clinician or other qualified observer.

"Variant" used herein with respect to a nucleic acid means (i) a portion or fragment of a referenced nucleotide sequence; (ii) the complement of a referenced nucleotide sequence or portion thereof (iii) a nucleic acid that is substantially identical to a referenced nucleic acid or the complement thereof or (iv) a nucleic acid that hybridizes under stringent conditions to the referenced nucleic acid, complement thereof, or a sequence substantially identical thereto. A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof.

"Variant" with respect to a polypeptide is one that differs in amino acid sequence by the insertion, deletion, or conservative substitution of amino acids, but retains at least one biological activity of the reference polypeptide. Variant can also mean a protein with an amino acid sequence that is substantially identical to a referenced protein with an amino acid sequence that retains at least one biological activity. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and in one embodiment, is an expression plasmid. The vector can contain or include one or more heterologous nucleic acid sequences.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double-stranded or can contain portions of both double-stranded and single-stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating, or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein can facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

As used herein, the expression "a subject in need thereof" means a human or non-human mammal that exhibits one or more symptoms or indications of brain cancer, and/or who has been diagnosed with brain cancer, including for example glioblastoma, and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. The term includes subjects with primary or metastatic tumors (advanced malignancies). For example, the expression includes subjects who have been newly diagnosed. In some embodiment, the expression includes subjects for whom treatment in accordance with the disclosed methods is an initial treatment (e.g., "first line" treatment, wherein the patient has not received prior systemic treatment for the cancer). In certain embodiments, the expression includes subjects for whom treatment in accordance with the disclosed methods is "second-line" treatment, wherein the patient has been previously treated with "standard-of-care" therapy including, but not limited to chemotherapy, surgery and radiation.

As used herein, the term "treat", "treating", or the like, means to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

As used herein, the phrase "in combination with" means that the cancer antigens hTERT, PSMA, and WT-1 are administered to the subject at the same time as, just before, or just after administration of the adjuvant, the PD-1 checkpoint inhibitor, radiation therapy, and/or chemotherapeutic agent. In certain embodiments, the cancer antigens are administered as a co-formulation with the adjuvant.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMA or a corresponding national regulatory agency. For example, proof may be provided by the clinical trial described in the example provided herein.

The term "clinically proven safe", as it relates to a dose, dosage regimen, treatment or method with cancer antigens hTERT, PSMA, WT1 (for example, administered as INO-5401 or a biosimilar or bioequivalent thereof) in combination with the adjuvant, such as IL-12 (for example, administered as INO-9012 or a biosimilar or bioequivalent thereof) and a PD-1 checkpoint inhibitor, such as an anti-PD-1 antibody (e.g., the anti-PD-1 antibody REGN2810 or a biosimilar or bioequivalent thereof), refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a patient administered a medicinal product. One index of safety is the National Cancer Institute (NCI) incidence of adverse events (AE) graded per Common Toxicity Criteria for Adverse Events CTCAE v4.03.

The terms "clinically proven efficacy" and "clinically proven effective" as used herein in the context of a dose, dosage regimen, treatment or method refer to the effectiveness of a particular dose, dosage, or treatment regimen. Efficacy can be measured based on change in the course of the disease in response to an agent of the present invention. For example, a combination of cancer antigens hTERT, PSMA, WT1, and adjuvant, (for example, INO-5401 or a biosimilar or bioequivalent thereof in combination with INO-9012 or a biosimilar or bioequivalent thereof) with a PD-1 checkpoint inhibitor, such as an anti-PD-1 antibody (e.g., the anti-PD-1 antibody cemiplimab or a biosimilar or bioequivalent thereof), is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, the combination of cancer antigens hTERT, PSMA, WT1, and adjuvant, (for example, INO-5401 or a biosimilar or bioequivalent thereof in combination with INO-9012 or a biosimilar or bioequivalent thereof) with an anti-PD-1 antibody (e.g., the anti-PD-1 antibody cemiplimab or a biosimilar or bioequivalent thereof), may be administered to achieve an improvement in a patient's condition related to brain cancer, such as glioblastoma (GBM). Improvement may be indicated by an improvement in an index of disease activity, by amelioration of clinical symptoms or by any other measure of disease activity.

As used herein, "INO-5401" refers to an immunologic composition of three DNA plasmids: a DNA plasmid comprising an insert encoding hTERT operably controlled by a promoter, a DNA plasmid comprising an insert encoding WT1 operably controlled by a promoter, and a DNA plasmid comprising an insert encoding PSMA operably controlled by a promoter.

As used herein, the term "radiation therapy", also referred to as "XRT," means using ionizing radiation to kill cancer cells, generally as part of anti-cancer therapy. X-rays, gamma rays or charged particles (e.g., protons or electrons) are used to generate ionizing radiation.

Radiation therapy may be delivered by a machine placed outside the patient's body (external-beam radiation therapy), or by a source placed inside a patient's body (internal radiation therapy or brachytherapy), or through systemic radioisotopes delivered intravenously or orally (systemic radioisotope therapy). Radiation therapy may be planned and administered in conjunction with imaging-based techniques such a computed tomography (CT), magnetic resonance imaging (MRI) to accurately determine the dose and location of radiation to be administered. In various embodiments, radiation therapy is selected from the group consisting of total all-body radiation therapy, conventional external beam radiation therapy, stereotactic radiosurgery, stereotactic body radiation therapy, 3-D conformal radiation therapy, intensity-modulated radiation therapy, image-guided radiation therapy, tomotherapy, brachytherapy, and systemic radiation therapy. Depending upon the intent, in certain embodiments, radiation therapy is curative, adjuvanating or palliative. In specific embodiments, the term "radiation therapy" refers to hypofractionated radiation therapy. Hypofractionated radiation therapy refers to a radiation treatment schedule in which the total dose of radiation is divided into large doses and treatments are given once a day or less often. Hypofractionated radiotherapy may provide more radiation per dose in fewer doses than standard radiotherapy. In various embodiments, each fraction comprises 2-20 Gy. For example, a radiation dose of 50 Gy may be split up into 10 fractions, each comprising 5 Gy. In certain embodiments, the 2 or more fractions are administered on consecutive or sequential days. In certain other embodiments, the 2 or more fractions are administered once in 2 days, once in 3 days, once in 4 days, once in 5 days, once in 6 days, once in 7 days, or in a combination thereof.

As used herein, the term "isomiR" refers to isoforms of canonical (mature) miRNAs. IsomiRs may have the following variations from the canonical miRNA: (1) addition and/or deletion of nucleotide(s) at the 5'-end of the canonical miRNA; (2) addition and/or deletion of nucleotide(s) at the 3'-end of canonical miRNA; (3) addition and/or deletion of nucleotide(s) at both 5'- and 3'-ends of the canonical miRNA; and (4) nucleotide substitution within the sequence of the canonical miRNA.

As used herein, the term "sensitivity" refers to the proportion of treated subjects with brain cancer who do not meet the defined TMM threshold.

As used herein, the term "specificity" refers to the proportion of treated subjects with brain cancer who meet the defined TMM threshold.

As used herein, the term "negative predictive value" refers to the ability to accurately select for subjects who would respond clinically to a disclosed prior to treatment with the disclosed therapy.

As used herein, the term "positive predictive value" refers to the ability to accurately predict for lack of response to treatment with a disclosed therapy.

As used herein, the term "defined TMM threshold" or "defined threshold" refers to a TMM value that causes both negative and positive predictive values as well as sensitivity and specificity to exceed 70% according to the Classification and Regression Tree (CART) analysis described in the Examples.

Methods of Treatment, Uses and Diagnosis

Provided herein are vaccines and methods of their use to prevent or treat cancer. Also provided herein are methods of selecting a subject for brain cancer therapy. The cancer can be brain cancer, for example, glioblastoma. The vaccine preferably includes at least three cancer antigens, hTERT, WT-1, and PSMA. In certain embodiments, the vaccine also includes an adjuvant, such as IL-12, and an anti-PD-1 antibody. The methods involve administering cancer antigens hTERT, WT-1, and PSMA, an adjuvant, and a PD-1 checkpoint inhibitor, such as an anti-PD-1 antibody to a subject in need thereof. In some embodiments, the methods prevent tumor growth. In some embodiments, the methods can reduce tumor growth and/or mass. In some embodiments, the methods can prevent metastasis of tumor cells. In some embodiments, the methods can increase a cellular immune response in the subject. In some embodiments, the methods increase tumor-free survival, progression-free survival, overall survival, or any combination thereof, of the subject.

In particular embodiments, the disclosed methods and uses can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8+ (CTL) to attack and kill tumor cells; (3) increase T helper cell responses; (4) and increase inflammatory responses via IFN-γ and TFN-α; or (5) any combination of the aforementioned. The methods can increase progression-free survival by 30%, 31%, 32%, 33%, 34%, 35%, 36%, 37%, 38%, 39%, 40%, 41%, 42%, 43%, 44%, and 45%. The methods can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The methods can prevent and block increases in monocyte chemoattractant protein 1 (MCP-1), a cytokine secreted by myeloid derived suppressor cells. The methods can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60%.

The disclosed methods and uses can increase a cellular immune response in a subject by about 50-fold to about 6000-fold, about 50-fold to about 5500-fold, about 50-fold to about 5000- fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the method or administered a standard-of-care treatment method. In some embodiments the methods can increase the cellular immune response in the subject by about 50-fold, 100-fold, 150-fold, 200-fold, 250-fold, 300-fold, 350-fold, 400-fold, 450-fold, 500- fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the method or administered a standard-of-care treatment method.

In some embodiments, the disclosed methods and uses can increase tumor-free survival, reduce tumor mass, increase progression-free survival, increase overall survival, or a combination thereof in the subject. The methods can increase tumor-free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The methods can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% in the subject. The methods can increase progression-free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject. The methods can increase overall survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% in the subject.

In certain embodiments, administration of IL-12; an immunogenic composition of hTERT, WT-1, and PSMA; and an anti-PD-1 antibody results in survival or improved overall survival at 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, or 42 months post administration.

In certain embodiments, administration of IL-12; an immunogenic composition of hTERT, WT-1, and PSMA; and an anti-PD-1 antibody results in survival at 18 months post administration. In further embodiments, administration of IL-12; an immunogenic composition of hTERT, WT-1, and PSMA; and an anti-PD-1 antibody results in improved overall survival at 18 months post administration. In further embodiments, administration of IL-12; an immunogenic composition of hTERT, WT-1, and PSMA; and an anti-PD-1 antibody results in improved overall survival at 18 months post administration relative to a patient population with brain cancer that has been administered a placebo. In certain embodiments, said administration or of hTERT, WT-1, and PSMA; and an anti-PD-1 antibody results in improved overall survival at 18 months post administration relative to a patient population with brain cancer that has not been administered an immunogenic composition of hTERT, WT-1, and PSMA; and an anti-PD-1 antibody. In certain embodiments, said administration or of hTERT, WT-1, and PSMA; and an anti-PD-1 antibody results in improved overall survival at 18 months post administration relative to a patient population with brain cancer that is deceased at 18 months post administration of IL-12; an immunogenic composition of hTERT, WT-1, and PSMA; and an anti-PD-1 antibody.

In certain embodiments, administration of IL-12; an immunogenic composition of hTERT, WT-1, and PSMA; and an anti-PD-1 antibody results in survival at 12 months post administration. In further embodiments, administration of IL-12; an immunogenic composition of hTERT, WT-1, and PSMA; and an anti-PD-1 antibody results in improved overall survival at 12 months post administration. In further embodiments, administration of IL-12; an immunogenic composition of hTERT, WT-1, and PSMA; and an anti-PD-1 antibody results in improved overall survival at 12 months post administration relative to a patient population with brain cancer that has been administered a placebo. In certain embodiments, said administration or of hTERT, WT-1, and PSMA; and an anti-PD-1 antibody results in improved overall survival at 12 months post administration relative to a patient population with brain cancer that has not been administered an immunogenic composition of hTERT, WT-1, and PSMA; and an anti-PD-1 antibody. In certain embodiments, said administration or of hTERT, WT-1, and PSMA; and an anti-PD-1 antibody results in improved overall survival at 12 months post administration relative to a patient population with brain cancer that is deceased at 12 months post administration of IL-12; an immunogenic composition of hTERT, WT-1, and PSMA; and an anti-PD-1 antibody.

In certain embodiments, administration of IL-12; an immunogenic composition of hTERT, WT-1, and PSMA; and an anti-PD-1 antibody results in improved median overall survival. In further embodiments, administration of IL-12; an immunogenic composition of hTERT, WT-1, and PSMA; and an anti-PD-1 antibody results in improved median overall survival relative to a patient population with brain cancer that has been administered a placebo. In certain embodiments, said administration or of hTERT, WT-1, and PSMA; and an anti-PD-1 antibody results in improved median overall survival relative to a patient population with brain cancer that has not been administered an immunogenic composition of hTERT, WT-1, and PSMA; and an anti-PD-1 antibody. In certain embodiments, said administration or of hTERT, WT-1, and PSMA; and an anti-PD-1 antibody results in improved median overall survival relative to a patient population with brain cancer that is deceased post administration of IL-12; an immunogenic composition of hTERT, WT-1, and PSMA; and an anti-PD-1 antibody. In certain embodiments, administration of IL-12; an immunogenic composition of hTERT, WT-1, and PSMA; and an anti-PD-1 antibody results in median overall survival of about 19.5 months. In certain embodiments, administration of IL-12; an immunogenic composition of hTERT, WT-1, and PSMA; and an anti-PD-1 antibody results in median overall survival in subjects having an unmethylated MGMT promoter of about 17.9 months. In certain embodiments, administration of IL-12; an immunogenic composition of hTERT, WT-1, and PSMA; and an anti-PD-1 antibody results in median overall survival in subjects having a methylated MGMT promoter of about 32.5 months.

The recombinant cancer antigens can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In certain embodiments, IL-12 is encoded by a DNA plasmid, for example, INO-9012 or a biosimilar or bioequivalent thereof. In certain embodiments, hTERT, WT-1, and PSMA are encoded by one or more DNA plasmids, for example, INO-5401 or a biosimilar or bioequivalent thereof. In further embodiments, the hTERT is encoded by a DNA plasmid, WT-1 is encoded by a DNA plasmid, and/or PSMA is encoded by a DNA plasmid. In still further embodiments, the hTERT, WT-1, and PSMA are encoded by the same DNA plasmid; two of hTERT, WT-1, and PSMA are encoded by the same DNA plasmid; or wherein hTERT, WT-1, and PSMA are each encoded by a different DNA plasmid.

In certain embodiments, the anti-PD-1 antibody is cemiplimab or a biosimilar or bioequivalent thereof. In certain embodiments, the methods further comprise administering radiation therapy and/or a chemotherapeutic agent, for example, temozolomide or a bioequivalent thereof. In certain embodiments, the anti-PD-1 antibody: comprises the heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2; comprises three HCDRs (HCDR1, HCDR2 and HCDR3) and three LCDRs (LCDR1, LCDR2 and LCDR3), wherein HCDR1 comprises the amino acid sequence of SEQ ID NO: 3, HCDR2 comprises the amino acid sequence of SEQ ID NO: 4, HCDR3 comprises the amino acid sequence of SEQ ID NO: 5, LCDR1 comprises the amino acid sequence of SEQ ID NO: 6, LCDR2 comprises the amino acid sequence AAS, and LCDR3 comprises the amino acid sequence of SEQ ID NO: 8; comprises a HCVR with 90% sequence identity to SEQ ID NO: 1; comprises a LCVR with 90% sequence identity to SEQ ID NO: 2; comprises a HCVR with 90% sequence identity to SEQ ID NO: 1 and a LCVR with 90% sequence identity to SEQ ID NO: 2; comprises a HCVR comprising the amino acid sequence of SEQ ID NO: 1 and a LCVR comprising the amino acid sequence of SEQ ID NO: 2; comprises a heavy chain comprising the amino acid sequence of SEQ ID NO: 9 and a light chain comprising the amino acid sequence of SEQ ID NO: 10; is an IgG4 antibody; or is REGN2810 or a biosimilar or bioequivalent thereof.

In certain embodiments, the IL12 p35 subunit comprises the amino acid sequence of SEQ ID NO: 23; the IL12 p40 subunit comprises the amino acid sequence of SEQ ID NO: 25; the IL12 p35 subunit comprises the amino acid sequence of SEQ ID NO: 23 and the IL12 p40 subunit comprises the amino acid sequence of SEQ ID NO: 25; the IL12 p35 subunit is encoded by the nucleic acid sequence of SEQ ID NO: 22; the IL12 p40 subunit is encoded by the nucleic acid sequence of SEQ ID NO: 24; or the IL12 p35 subunit is encoded by the nucleic acid sequence of SEQ ID NO: 22 and the IL12 p40 subunit is encoded by the nucleic acid sequence of SEQ ID NO: 24.

In certain embodiments, the hTERT comprises the amino acid sequence of SEQ ID NO: 20 or is encoded by the nucleic acid sequence of SEQ ID NO: 19; the WT-1 comprises the amino acid sequence of SEQ ID NO: 26 or is encoded by the nucleic acid sequence of SEQ ID NO: 27; and/or the PSMA comprises the amino acid sequence of SEQ ID NO: 28 or is encoded by the nucleic acid sequence of SEQ ID NO: 29.

The cancer can be brain cancer, for example, glioblastoma. In certain embodiments, the brain cancer is MGMT-methylated glioblastoma. In certain embodiments, the brain cancer is MGMT-unmethylated glioblastoma.

MicroRNA (miRNA) and IsomiRs

MicroRNAs (miRNAs) are a class of endogenous small noncoding RNA, typically ranging from 19 to 24 nucleotides. When loaded into the microribonucleoprotein (miRNP) or RNA induced silencing complex (RISC), miRNAs bind to miRNA recognition elements (MREs) on mRNA targets, exerting gene regulation through post-transcriptional and/or translational mechanisms. To date, there is no known miRNA or group of miRNAs that have been used in a fashion that allows for the prediction of a response to immunotherapy for a given disease state.

Thought to be the products of altered miRNA biogenesis, isomiRs may have additions or deletions at the 5'-, 3'- or both ends of the canonical miRNA. In some rare cases, isomiRs may have some nucleotides substituted within the canonical sequence (polymorphic isomiRs). These isomiRs, originally mistaken to be sequencing artifacts, have recently been confirmed by multiple, parallel sequencing and bioinformatic studies to be bona fide miRNA species, greatly expanding the miRNA repertoire.

Recent studies have increasingly shown that these isomiRs may be conserved across species and produced in a regulated cell-specific manner or at a particular developmental stage. IsomiRs can also be loaded into miRNPs/RISCs and the variations in length and sequences would potentially alter target selection, miRNA loading and stability, possibly with important and different biological functions.

With the advancement of molecular biological techniques, miRNAs can be detected using multiple platforms. Most current miRNA studies are reported using quantitative reverse transcription polymerase chain reaction (qRT-PCR), microarrays and high-throughput sequencing. The use of next generation sequencing has led to the discovery of miRNA isoforms (isomiRs), which are variants of the canonical mature miRNA sequences.

Provided herein are methods of treating brain cancer in a subject, comprising, consisting of, or consisting essentially of: (a) measuring an expression level of a miR-331-3p miRNA comprising SEQ ID NO: 30 or isomiRs thereof and a miR-1537-3p miRNA comprising SEQ ID NO: 31 or isomiRs thereof in a biological sample from a subject who has brain cancer; and (b) administering IL-12; an immunogenic composition of hTERT, WT-1, and PSMA; and an anti-PD-1 antibody to said subject if the subject has an increased expression level of the miR-331-3p miRNA or isomiRs thereof and the miR-1537-3p miRNA or isomiRs thereof relative to a control population of subjects.

Also provided herein are methods for selecting a subject for brain cancer therapy comprising, consisting of, or consisting essentially of: (a) evaluating one or more biological samples from a subject who has brain cancer for the presence of a mIR-331-3p miRNA comprising SEQ ID NO: 30 or isomiRs thereof and a miR-1537-3p miRNA comprising SEQ ID NO: 31 or isomiRs thereof; and (b) characterizing the subject as a candidate for brain cancer therapy with IL-12; an immunogenic composition of hTERT, WT-1, and PSMA; and an anti-PD-1 antibody if the subject has an increased expression level of the mIR-331-3p miRNA or isomiRs thereof and the miR-1537-3p miRNA or isomiRs thereof relative to a control population of subjects.

Further provided herein are vaccines for use in treating brain cancer in a subject who has brain cancer and who harbors an miR-331-3p miRNA comprising SEQ ID NO: 30 or isomiRs thereof and a miR-1537-3p miRNA comprising SEQ ID NO: 31 or isomiRs thereof, wherein the expression level of the mIR-331-3p miRNA and the miR-1537-3p miRNA is increased relative to a control population of subjects, and wherein the vaccine comprises an immunogenic composition of hTERT, WT-1, and PSMA; and an anti-PD-1 antibody.

Still further provided herein are uses of a vaccine in the manufacture of a medicament for treating brain cancer in a subject who has brain cancer and who harbors an mIR-331-3p miRNA comprising SEQ ID NO: 30 or isomiRs thereof and a miR-1537-3p miRNA comprising SEQ ID NO: 31 or isomiRs thereof, wherein the expression level of the mIR-331-3p miRNA and the miR-1537-3p miRNA is increased relative to a control population of subjects, and wherein the vaccine comprises an immunogenic composition of hTERT, WT-1, and PSMA; and an anti-PD-1 antibody.

In certain embodiments, the biological sample is taken from the subject at baseline, e.g. prior to administration of the therapeutic composition. In certain embodiments, the increase relative to a control population of subjects is measured at baseline for both the subject and the control population of subjects, e.g. prior to administration of the therapeutic composition.

In certain embodiments, the biological sample is taken from the subject prior to administration of the IL-12; an immunogenic composition of hTERT, WT-1, and PSMA; and the anti-PD-1 antibody. In certain embodiments, the biological sample is taken from the control population of subjects prior to administration of the IL-12; an immunogenic composition of hTERT, WT-1, and PSMA; and the anti-PD-1 antibody. In certain embodiments, the biological sample is taken from the subject and from the control population of subjects prior to administration of the IL-12; an immunogenic composition of hTERT, WT-1, and PSMA; and the anti-PD-1 antibody.

In certain embodiments, administration of IL-12; an immunogenic composition of hTERT, WT-1, and PSMA; and an anti-PD-1 antibody results in survival or improved overall survival at 1, 2, 3, 4, 5, 6, 7, 8, 9, 10, 11, 12, 13, 14, 15, 16, 17 or 18 months post administration. In certain embodiments, administration of IL-12; an immunogenic composition of hTERT, WT-1, and PSMA; and an anti-PD-1 antibody results in survival or improved overall survival at 18 months post administration. In certain embodiments, administration of IL-12; an immunogenic composition of hTERT, WT-1, and PSMA; and an anti-PD-1 antibody results in survival or improved overall survival at 12 months post administration.

In further embodiments, the control population of subjects is deceased at 1, 2, 3, 4, 5, 6, 7, 8, 9, 10, 11, 12, 13, 14, 15, 16, 17 or 18 months months post administration of IL-12; an immunogenic composition of hTERT, WT-1, and PSMA; and an anti-PD-1 antibody. In certain embodiments, the control population of subjects is deceased at 18 months post administration of IL-12; an immunogenic composition of hTERT, WT-1, and PSMA; and an anti-PD-1 antibody. In certain embodiments, the control population of subjects is deceased at 12 months post administration of IL-12; an immunogenic composition of hTERT, WT-1, and PSMA; and an anti-PD-1 antibody.

In some aspects of the present disclosure, the biological sample is a peripheral blood sample. In certain embodiments, the biological sample is a plasma sample.

In some aspects of the present disclosure, the methods comprise evaluating one or more biological sample. In certain embodiments, the methods comprising evaluating one biological sample. In certain embodiments, the methods comprising evaluating two biological samples. In certain embodiments, the methods comprising evaluating three biological sample. In certain embodiments, the methods comprising evaluating four biological samples. In certain embodiments, the methods comprising evaluating five biological samples.

In certain embodiments, the subject has an unmethylated MGMT gene promoter. In further embodiments, the subject has a methylated MGMT gene promoter.

Messenger RNA (mRNA)

Provided herein are methods of treating brain cancer in a subject, comprising, consisting of, or consisting essentially of: (a) measuring an expression level of at least one mRNA biomarker selected from SYNGR3, OTX1, GABBR2, LHX1, CADM3, MLLT11, MNX1, GRB14, SLC34A2, PHYHIP, WNT10B, SLC17A6, CRLF1, HOXD13, TGFβR3, UBA7, SFRP4, or any combination thereof, in a tumor sample from a subject who has brain cancer; and (b) administering IL-12; an immunogenic composition hTERT, WT-1, and PSMA; and an anti-PD-1 antibody to said subject if the expression level of SYNGR3, OTX1, GABBR2, LHX1, CADM3, MLLT11, MNX1, GRB14, SLC34A2, PHYHIP, WNT10B, SLC17A6, CRLF1 and HOXD13 is decreased or if the expression level of TGFβR3, UBA7, SFRP4 is increased relative to a control population of subjects.

Also provided herein are methods for selecting a subject for brain cancer therapy comprising, consisting of, or consisting essentially of: (a) measuring an expression level of at least one mRNA biomarker selected from SYNGR3, OTX1, GABBR2, LHX1, CADM3, MLLT11, MNX1, GRB14, SLC34A2, PHYHIP, WNT10B, SLC17A6, CRLF1, HOXD13, TGFβR3, UBA7, SFRP4, or any combination thereof, in a tumor sample from a subject who has brain cancer; and (b) characterizing the subject as a candidate for brain cancer therapy with IL-12; an immunogenic composition of hTERT, WT-1, and PSMA; and an anti-PD-1 antibody if the expression level of SYNGR3, OTX1, GABBR2, LHX1, CADM3, MLLT11, MNX1, GRB14, SLC34A2, PHYHIP, WNT10B, SLC17A6, CRLF1 and HOXD13 is decreased or if the expression level of TGFβR3, UBA7, SFRP4 is increased relative to a control population of subjects.

Further provided herein are vaccines for use in treating brain cancer in a subject who has brain cancer, who has an unmethylated MGMT gene promoter, and who harbors at least one mRNA biomarker selected from SYNGR3, OTX1, GABBR2, LHX1, CADM3, MLLT11, MNX1, GRB14, SLC34A2, PHYHIP, WNT10B, SLC17A6, CRLF1, HOXD13, TGFβR3, UBA7, SFRP4, or any combination thereof, wherein the expression level of SYNGR3, OTX1, GABBR2, LHX1, CADM3, MLLT11, MNX1, GRB14, SLC34A2, PHYHIP, WNT10B, SLC17A6, CRLF1 and HOXD13 is decreased or the expression level of TGFβR3, UBA7, SFRP4 is increased relative to a control population of subjects.

Still further provided herein are uses of a vaccine in the manufacture of a medicament for treating brain cancer in a subject who has brain cancer, who has an unmethylated MGMT gene promoter, and who harbors at least one mRNA biomarker selected from SYNGR3, OTX1, GABBR2, LHX1, CADM3, MLLT11, MNX1, GRB14, SLC34A2, PHYHIP, WNT10B, SLC17A6, CRLF1, HOXD13, TGFβR3, UBA7, SFRP4, or any combination thereof, wherein the expression level of SYNGR3, OTX1, GABBR2, LHX1, CADM3, MLLT11, MNX1, GRB14, SLC34A2, PHYHIP, WNT10B, SLC17A6, CRLF1 and HOXD13 is decreased or the expression level of TGFβR3, UBA7, SFRP4 is increased relative to a control population of subjects.

In certain embodiments, the biological sample is taken from the subject at baseline, e.g. prior to administration of the therapeutic composition. In certain embodiments, the increase relative to a control population of subjects is measured at baseline for both the subject and the control population of subjects, e.g. prior to administration of the therapeutic composition.

In certain embodiments, the biological sample is taken from the subject prior to administration of the IL-12; an immunogenic composition of hTERT, WT-1, and PSMA; and the anti-PD-1 antibody. In certain embodiments, the biological sample is taken from the control population of subjects prior to administration of the IL-12; an immunogenic composition of hTERT, WT-1, and PSMA; and the anti-PD-1 antibody. In certain embodiments, the biological sample is taken from the subject and from the control population of subjects prior to administration of the IL-12; an immunogenic composition of hTERT, WT-1, and PSMA; and the anti-PD-1 antibody.

In certain embodiments, administration of IL-12; an immunogenic composition of hTERT, WT-1, and PSMA; and an anti-PD-1 antibody results in survival or improved overall survival at 1, 2, 3, 4, 5, 6, 7, 8, 9, 10, 11, 12, 13, 14, 15, 16, 17 or 18 months post administration. In certain embodiments, administration of IL-12; an immunogenic composition of hTERT, WT-1, and PSMA; and an anti-PD-1 antibody results in survival or improved overall survival at 18 months post administration. In certain embodiments, administration of IL-12; an immunogenic composition of hTERT, WT-1, and PSMA; and an anti-PD-1 antibody results in survival or improved overall survival at 12 months post administration.

In further embodiments, the control population of subjects is deceased at 1, 2, 3, 4, 5, 6, 7, 8, 9, 10, 11, 12, 13, 14, 15, 16, 17 or 18 months months post administration of IL-12; an immunogenic composition of hTERT, WT-1, and PSMA; and an anti-PD-1 antibody. In certain embodiments, the control population of subjects is deceased at 18 months post administration of IL-12; an immunogenic composition of hTERT, WT-1, and PSMA; and an anti-PD-1 antibody. In certain embodiments, the control population of subjects is deceased at 12 months post administration of IL-12; an immunogenic composition of hTERT, WT-1, and PSMA; and an anti-PD-1 antibody.

In certain embodiments, the biological sample is a primary tumor sample.

In certain embodiments, the subject has an unmethylated MGMT gene promoter. In further embodiments, the subject has a methylated MGMT gene promoter.

Therapeutic Compositions

Disclosed herein are optimized consensus sequences of cancer antigens hTERT, WT-1, and PSMA. In one embodiment, the antigen encoded by the optimized consensus sequence is capable of eliciting an immune response in a mammal. In one embodiment, the antigen encoded by the optimized consensus sequence can comprise an epitope(s) that makes it particularly effective as an immunogen against which an immune response can be induced.

In one embodiment is provided an optimized consensus PSMA designed to break tolerance to native human PSMA. In one embodiment, a human optimized consensus PSMA encoding sequence is as set forth in SEQ ID NO:11, SEQ ID NO:12, SEQ ID NO: 21, or SEQ ID NO: 28. In one embodiment, a human optimized consensus PSMA encoded antigen has an amino acid sequence as set forth in SEQ ID NO:13, SEQ ID NO:14, or SEQ ID NO: 28.

In one embodiment, an optimized consensus WT-1 is designed to break tolerance to native human WT-1. In one embodiment, a human optimized consensus WT-1 encoding sequence is as set forth in SEQ ID NO:15 or SEQ ID NO: 27. In one embodiment, a human optimized consensus WT-1 encoded antigen has an amino acid sequence as set forth in SEQ ID NO:16 or SEQ ID NO: 26.

In one embodiment, an optimized consensus TERT is designed to break tolerance to native human TERT. In one embodiment, a human optimized consensus TERT encoding sequence is as set forth in SEQ ID NO:17 or SEQ ID NO:19. In one embodiment, a human optimized consensus TERT encoded antigen has an amino acid sequence as set forth in SEQ ID NO:18 and SEQ ID NO:20.

The disclosed vaccines may further comprise an adjuvant. In certain embodiments, the disclosed methods of treatment further comprise administering to the subject an adjuvant. In certain embodiments, the adjuvant is IL12. IL12 may be included in a vaccine in the form of its p35 and p40 subunits. The adjuvant IL12 may be administered to the subject as its p35 and p40 subunits. The IL12 p35 and p40 subunits may be encoded by the same expression vector or by separate expression vectors. In one embodiment, the IL12 p35 encoding sequence is as set forth in SEQ ID NO:22. In one embodiment, the IL12 p35 subunit has an amino acid sequence as set forth in SEQ ID NO:23. In one embodiment, the IL12 p40 encoding sequence is as set forth in SEQ ID NO:24. In one embodiment, the IL12 p40 subunit has an amino acid sequence as set forth in SEQ ID NO:25.

The cancer antigens TERT, WT-1, PSMA, and/or adjuvant can be present in the vaccine or administered to the subject as the polypeptide, fragment thereof, variant thereof, nucleic acid sequence encoding the polypeptide, fragment or variant thereof, or any combination thereof. The cancer antigen can be any form that induces an immune response in a subject. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The cancer antigens TERT, WT-1, PSMA, and/or adjuvant can be included in a vaccine or administered to the subject as the polypeptide, fragment thereof, variant thereof, nucleic acid sequence encoding the polypeptide, fragment or variant thereof, or any combination thereof. The cancer antigen can be any form that induces an immune response in a subject. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The cancer antigens TERT, WT-1, PSMA and/or IL-12 can be included in a vaccine or administered as one or more nucleic acid molecules, for example but not limited to, an expression vector(s). An expression vector can be a circular plasmid or a linear nucleic acid. An expression vector is capable of directing expression of a particular nucleotide sequence in an appropriate subject cell. An expression vector can have a promoter operably linked to the antigen-encoding nucleotide sequence, which may be operably linked to termination signals. An expression vector can also contain sequences required for proper translation of the nucleotide sequence. The expression vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

In one embodiment, the nucleic acid is an RNA molecule. Accordingly, in one embodiment, the invention provides an RNA molecule encoding one or more polypeptides of interest. The RNA may be plus-stranded. Accordingly, in some embodiments, the RNA molecule can be translated by cells without needing any intervening replication steps such as reverse transcription. An RNA molecule useful with the invention may have a 5' cap (e.g. a 7- methylguanosine). This cap can enhance in vivo translation of the RNA. The 5' nucleotide of an RNA molecule useful with the invention may have a 5' triphosphate group. In a capped RNA this may be linked to a 7-methylguanosine via a 5'-to-5' bridge. An RNA molecule may have a 3' poly-A tail. It may also include a poly-A polymerase recognition sequence (e.g., AAUAAA) near its 3' end. An RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

The expression vector may be a circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression. The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system. The LEC can be pcrM2. The LEC can be pcrNP. pcrNP and pcrMR can be derived from pNP (Puerto Rico/34) and pM2 (New Caledonia/99), respectively.

The vector can comprise heterologous nucleic acid encoding the above described antigens and can further comprise an initiation codon, which can be upstream of the one or more cancer antigen coding sequence(s), and a stop codon, which can be downstream of the coding sequence(s) of the above described antigens.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The initiation and termination codon can be in frame with the coding sequence(s) of the above described antigens. The vector can also comprise a promoter that is operably linked to the coding sequence(s) of the above described antigens. The promoter operably linked to the coding sequence(s) of the above described antigens can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metallothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens and/or antibodies. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the above described antigens.

The enhancer can be necessary for expression. The enhancer can be human actin, human myosin, human hemoglobin, human muscle creatine or a viral enhancer such as one from CMV, HA, RSV or EBV.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

The disclosed methods may comprise administration of a plurality of copies of a single nucleic acid molecule such as a single plasmid, or a plurality of copies of two or more different nucleic acid molecules such as two or more different plasmids. For example, the methods may comprise administration of two, three, four, five, six, seven, eight, nine or ten or more different nucleic acid molecules.

The nucleic acid molecules used in accordance with the disclosed methods, such as plasmids, may collectively contain coding sequence for a single antigen or for multiple antigens. As an example, in one embodiment, the antigens are multiple antigens selected from TERT and one or more additional cancer antigens. In one exemplary embodiment, the antigens are TERT and WT-1. In one exemplary embodiment, the antigens are TERT and PSMA. In one exemplary embodiment, the antigens are PSMA and one or more additional cancer antigens. In one exemplary embodiment, the antigens are PSMA and WT-1. In another exemplary embodiment, the antigens are TERT, WT-1 and PSMA.

The vector can further comprise elements or reagents that inhibit it from integrating into the chromosome. The vector can comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 base pair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811.

Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>—2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The one or more cancer antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), incorporated fully herein by reference.

Exemplary DNA plasmids encoding the cancer antigens hTERT, WT-1, and/or PSMA are disclosed in U.S. Application No. 62/899,543, filed Sep. 12, 2019, the entire contents of which are disclosed herein by reference.

Dosing and Routes of Administration

In accordance with the disclosed methods and uses, the subject may be administered about 5 nanograms to about 20 mg of a nucleic acid molecule(s) encoding an antigen or antigens. In some embodiments, the subject may be administered about 5 mg to about 15 mg of a nucleic acid molecule(s) encoding an antigen or antigens. In some embodiments, the subject may be administered about 9 mg to about 11 mg of a nucleic acid molecule(s) encoding an antigen or antigens. In some embodiments, the subject may be administered about 10 mg of a nucleic acid molecule(s) encoding an antigen or antigens.

In certain embodiments, the discloses methods and uses comprise administering to the subject 3 mg of the DNA plasmid encoding hTERT, 3 mg of the DNA plasmid encoding PSMA, 3 mg of the DNA plasmid encoding WT-1, and 1 mg of the plasmid encoding IL-12.

In certain embodiments, the IL-12 and the immunogenic composition are co-administered by intramuscular injection every three weeks for four doses and then every nine weeks. In further embodiments, the disclosed methods and uses further comprise electroporation following each intramuscular injection.

The DNA plasmid(s) can be delivered via a variety of routes. Typical delivery routes include parenteral administration, e.g., intradermal, intramuscular, or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The DNA plasmid(s) can also be administered to muscle, or can be administered via intradermal or subcutaneous injections, or transdermally, such as by iontophoresis. Epidermal administration of the DNA plasmid(s) can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The DNA plasmid(s) can be a liquid preparation such as a suspension, syrup, or elixir. The vaccine can also be a preparation for parenteral, subcutaneous, intradermal, intramuscular, or intravenous administration (e.g., injectable administration), such as a sterile suspension or emulsion.

The DNA plasmid(s) can be incorporated into liposomes, microspheres, or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The DNA plasmid(s) can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the DNA plasmid(s) into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver DNA plasmid(s) to all types of tissues, particularly to skin and mucosa. In some embodiments, a needle-free injector may be used to propel a liquid that contains the DNA plasmid(s) to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system are described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle injectors that deliver the DNA plasmid(s) and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15-volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA® (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated, and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The CELLECTRA® device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described DNA plasmid(s) herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprise means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected, and the size of electric field applied may be reduced while achieving a good fit between the electric field and the fluid.

Upon administration of nucleic acid molecule(s) encoding cancer antigens hTERT, PSMA, and WT-1 to the subject, the transfected cells will express and secrete one or more of the cancer antigens. These secreted proteins, or synthetic antigens, will be recognized as foreign by the immune system, which will mount an immune response that can include antibodies made against the one or more cancer antigens, and T-cell response specifically against the one or more cancer antigens. In some examples, a mammal administered the immunogenic composition discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

The recombinant cancer antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

Combination with Anti-PD-1 Antibody

The disclosed vaccines may further comprise an anti-PD-1 antibody. The disclosed methods of treatment may further comprise administering to the subject an anti-PD-1 antibody. According to certain embodiments of the present invention, the anti-PD-1 antibody comprises a heavy chain variable region (HCVR), light chain variable region (LCVR), and/or complementarity determining regions (CDRs) comprising the amino acid sequences of any of the anti-PD-1 antibodies as set forth in US Patent Publication No. 20150203579, hereby incorporated in its entirety. In certain exemplary embodiments, the anti-PD-1 antibody that can be used in the context of the disclosed methods comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-PD-1 antibody comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence AAS; and the LCDR3 comprises the amino acid sequence of SEQ ID NO: 8. In yet other embodiments, the anti-PD-1 antibody comprises an HCVR comprising SEQ ID NO: 1 and an LCVR comprising SEQ ID NO: 2. In certain embodiments, the methods of the present invention comprise the use of an anti-PD-1 antibody, wherein the antibody comprises a heavy chain comprising the amino acid sequence of SEQ ID NO: 9. In some embodiments, the anti-PD-1 antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-PD-1 antibody known as REGN2810 and also known as cemiplimab or cemiplimab-rwlc.

According to certain exemplary embodiments, the methods of the present invention comprise the use of REGN2810, or a biosimilar or bioequivalent thereof. The term "bioequivalent", as used herein, refers to anti-PD-1 antibodies or PD-1-binding proteins or fragments thereof that are pharmaceutical equivalents or pharmaceutical alternatives whose rate and/or extent of absorption do not show a significant difference with that of REGN2810 when administered at the same molar dose under similar experimental conditions, either single dose or multiple dose. In the context of the invention, the term refers to antigen-binding proteins that bind to PD-1 which do not have clinically meaningful differences with REGN2810 in their safety, purity and/or potency.

According to certain embodiments of the present invention, the anti-human PD-1 antibody comprises a HCVR having 90%, 95%, 98% or 99% sequence identity to SEQ ID NO: 1.

According to certain embodiments of the present invention, the anti-human PD-1 antibody comprises a LCVR having 90%, 95%, 98% or 99% sequence identity to SEQ ID NO: 2.

According to certain embodiments of the present invention, the anti-human PD-1 antibody comprises a HCVR comprising an amino acid sequence of SEQ ID NO: 1 having no more than 5 amino acid substitutions. According to certain embodiments of the present invention, the anti-human PD-1 antibody comprises a LCVR comprising an amino acid sequence of SEQ ID NO: 2 having no more than 2 amino acid substitutions.

Sequence identity may be measured by any method known in the art (e.g., GAP, BESTFIT, and BLAST).

The present invention also includes use of anti-PD-1 antibodies in methods to treat cancer, wherein the anti-PD-1 antibodies comprise variants of any of the HCVR, LCVR and/or CDR amino acid sequences disclosed herein having one or more conservative amino acid substitutions. For example, the present invention includes use of anti-PD-1 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

The amount of anti-PD-1 antibody administered to a subject according to the disclosed methods can be a therapeutically effective amount. As used herein, the phrase "therapeutically effective amount" of anti-PD-1 antibody is an amount that results in one or more of: (a) a reduction in the severity or duration of a symptom or an indication of a cancer, e.g., glioblastoma; (b) inhibition of tumor growth, or an increase in tumor necrosis, tumor shrinkage and/or tumor disappearance; (c) delay in tumor growth and development; (d) inhibition of tumor metastasis; (e) prevention of recurrence of tumor growth; (f) increase in survival of a subject with a cancer; and/or (g) a reduction in the use or need for conventional anti-cancer therapy (e.g., reduced or eliminated use of chemotherapeutic or cytotoxic agents) as compared to an untreated subject or a subject administered the antibody as monotherapy.

In the case of an anti-PD-1 antibody or antigen-binding fragment thereof, a therapeutically effective amount can be from about 0.05 mg to about 600 mg, from about 1 mg to about 500 mg, from about 10 mg to about 450 mg, from about 50 mg to about 400 mg, from about 75 mg to about 350 mg, or from about 100 mg to about 300 mg of the antibody. For example, in various embodiments, the amount of the anti-PD-1 antibody is about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PD-1 antibody. In one embodiment, 250 mg of an anti-PD-1 antibody is administered according to the methods of the present invention. In one embodiment, 200 mg of an anti-PD-1 antibody is administered according to the methods of the present invention. In one embodiment, 350 mg of an anti-PD-1 antibody is administered according to the methods of the present invention.

The anti-PD-1 antibody may be administered to the subject in multiple doses, e.g., as part of a specific therapeutic dosing regimen. For example, the therapeutic dosing regimen may comprise administering one or more doses of an anti-PD-1 antibody to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

In some embodiments, the anti-PD-1 antibody is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the anti-PD-1 antibody, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

The anti-PD-1 antibody can be delivered subcutaneously or intravenously with a standard needle and syringe. In addition, with respect to subcutaneous delivery, a pen delivery device readily has applications in delivering the anti-PD-1 antibody. Such a pen delivery device can be reusable or disposable. A reusable pen delivery device generally utilizes a replaceable cartridge that contains a pharmaceutical composition of the anti-PD-1 antibody. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the anti-PD-1 antibody can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

Injectable preparations of the anti-PD-1 antibody may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending, or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

In certain embodiments, the anti-PD-1 antibody is formulated in a pharmaceutical composition for use in intravenous administration.

Combination with Radiation Therapy or Chemotherapy

In certain embodiments, the methods further comprise administering radiation therapy to the subject. In certain embodiments, the one or more doses of radiation therapy are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

In certain embodiments, the radiation therapy is hypofractionated radiation therapy. In some embodiments, each dose of radiation therapy comprises 20-50 Gy. In some embodiments, the subject is administered 20-50 Gy in 2-20 fractions. In some embodiments, each dose of radiation therapy comprises 20-60 Gy. In some embodiments, the subject is administered 20-60 Gy in 2-20 fractions. In certain embodiments, the fractionated radiation therapy comprises 40 Gy in 15 fractions.

In certain embodiments, the hypofractionated radiation therapy comprises 15 fractions. In certain embodiments, the 15 fractions are administered on 15-25 consecutive days. In certain embodiments, the 15 fractions are administered on 21 consecutive days.

In certain embodiments, the methods further comprise administering a chemotherapeutic agent to the subject, for example, temozolomide (TMZ). The chemotherapeutic agent can be administered with the radiation therapy. For example, TMZ is administered at a daily dose of 75 mg/m$^2$ concomitant with hypofractionated radiation therapy. In some embodiments, subjects having a tumor with a methylated MGMT promoter will be administered maintenance therapy of the chemotherapeutic agent. For example, following radiation therapy, subjects having a tumor with a methylated MGMT promoter may receive TMZ at a starting dose of 150 mg/m$^2$/day for 6 cycles on the first 5 days of a 28-day cycle (5 days "on," 23 days "off") with increased each maintenance cycle by 50 mg/m$^2$/dose to a maximum of 200 mg/m$^2$/dose, in the absence of hematologic toxicity. In some embodiments, the maintenance therapy will start approximately three to five weeks, preferably about 4 weeks, after the last dose of radiation therapy.

EXAMPLES

The examples and embodiments described herein are for illustrative purposes only and various modifications or changes suggested to persons skilled in the art are to be included within the spirit and purview of this application and scope of the appended claims.

Example 1: A Study of INO-5401 and INO-9012 Delivered by Electroporation (EP) in Combination With Cemiplimab (REGN2810) in Newly-Diagnosed Glioblastoma (GBM)

A non-limiting example of a phase 1/2 trial to evaluate safety, immunogenicity, and preliminary efficacy of INO-5401 and INO-9012 in combination with cemiplimab (REGN2810), with radiation and chemotherapy, in subjects with newly-diagnosed glioblastoma (GBM) is provided herein.

Objectives

Primary Objective: To evaluate the safety and tolerability of INO-5401 and INO-9012 delivered by intramuscular (IM) injection followed by EP with CELLECTRA® 2000 in combination with cemiplimab-rwlc in adult subjects with newly-diagnosed GBM.

Primary Endpoint(s) and Assessments:
  Incidence of adverse events (AE) graded per Common Toxicity Criteria for Adverse Events (CTCAE) v4.03, classified by system organ class, preferred term, severity, and relationship to trial treatment.
  Clinically significant changes in safety laboratory parameters from baseline.

Secondary Objectives:
  To evaluate preliminary clinical efficacy and immunogenicity of INO-5401 and INO-9012 delivered by IM injection followed by EP with CELLECTRA® 2000 in combination with cemiplimab-rwlc in adult subjects with newly-diagnosed GBM.
  To evaluate preliminary immunogenicity of INO-5401 and INO-9012 delivered by IM injection followed by EP with CELLECTRA® 2000 in combination with REGN2810 in adult subjects with newly-diagnosed GBM.

Secondary Endpoint(s) and Assessments:
  Overall survival at 18 months (OS18);
  Antigen-specific cellular immune responses assessed by:
    Interferon-γ secreting T lymphocytes in peripheral blood mononuclear cells (PBMC) by ELISpot;
    T-cell phenotype (e.g. activation and cytolytic cell, myeloid derived suppressor cell frequency (MDSC)) in PBMC by Flow Cytometry;
    T cell receptor (TCR) sequencing from PBMCs to assess diversity and putative antigen specificity;
  Antigen-specific humoral responses (e.g. B cell activation/antibody secretion).

Exploratory Objective(s):
  To explore correlative association between clinical efficacy and tumor genetics and/or biomarkers.
  To further evaluate efficacy of INO-5401 and INO-9012 delivered by IM injection followed by EP with CELLECTRA® 2000 in combination with REGN2810 and hypofractionated radiation therapy in adult subjects with newly-diagnosed GBM.

Exploratory Endpoint(s):
  Tumor infiltrating lymphocytes (TILS) and immuno suppressive elements, where feasible;
  Expression of tumor oncoproteins, including but not limited to tumor expression of hTERT, WT1, and PSMA by IHC, immunofluorescence (IF) or genome sequencing;
  MicroRNA signatures in blood plasma and/or sera;
  Circulating tumor cells, circulating endothelial cells, and/or circulating cancer associated macrophage-like cells from peripheral blood where feasible;
  Assessment of tumor-associated antigen (TAA)-specific peripheral T cells by RNAseq;
  Assessment of cytokine profiles from plasma and/or sera;
  Progression-Free Survival, as assessed by RANO (Response Assessment in Neurooncology) criteria and Immunotherapy Response Assessment in Neurooncology (iRANO) criteria;
  Overall Survival (OS).

Study Design

The study described in this example corresponds to ClinicalTrials_gov identifier NCT03491683. The data presented herein as associated with this study reflects the state of this study as of the time of this filing. In this study, antigen-specific T cell-generating therapy, INO-5401, combined with INO-9012, followed by electroporation with the CEL-LECTRA® 2000 device, together with a PD-1 checkpoint inhibitor, cemiplimab-rwlc, was given to patients with newly-diagnosed GBM, together with radiation and temozolomide, in order to evaluate tolerability, immunogenicity and anti-tumor activity of the combination. Ethics Approval by NYU Ethics Board; approval number i17-00764.

This is a Phase 1/2, open-label, multi-center trial to evaluate the safety, immunogenicity, and preliminary efficacy of INO-5401 and INO-9012 in combination with cemiplimab (also known as REGN2810) in subjects with newly-diagnosed GBM. All patients provided written informed consent.

Subjects started immunotherapy with REGN2810 upon definitive histopathological diagnosis of GBM and adequate recovery from surgical intervention. Subjects were assigned to a cohort based on the results of the MGMT gene methylation assay performed in a CLIA-certified laboratory, which was available prior to the completion of RT. The start of immunotherapy is designated as Day 0. REGN2810 was administered intravenously (IV) every three weeks until disease progression defined by iRANO (Immune Response Assessment in Neuro-Oncology), unacceptable toxicity, withdrawal of consent, or death.

On Day 0, subjects received INO-5401 and INO-9012 intramuscularly (IM) followed by electroporation (EP). INO-5401 and INO-9012 were administered, followed by EP, every three weeks for four doses, and then every 9 weeks until disease progression defined by iRANO, unacceptable toxicity, withdrawal of consent, or death.

Temozolomide was administered to all subjects both with and without MGMT promoter methylation, unless clinically contraindicated, during radiation therapy. Radiation therapy (RT) began no later than 42 days after surgical intervention. Radiation therapy started approximately 1 to 2 weeks after Day 0, and was continue(d) for approximately three weeks. Temozolomide (TMZ) was given daily during radiation therapy (TMZ/RT). Subjects with MGMT promoter methylation received maintenance (adjuvant) TMZ for 6 cycles, following recovery from TMZ/RT. Maintenance (adjuvant) TMZ was administered for the first 5 days of a 28-day cycle. This study had two cohorts: Cohort A, consisting of subjects with an unmethylated MGMT promoter, and Cohort B consisting of subjects with a methylated MGMT promoter.

Study Population

Each potential subject satisfied all of the following criteria to be enrolled in the study:

Overview of Patient Eligibility

Adults with newly-diagnosed GBM who are post-definitive surgery, and are able to receive standard therapy. Estimated Number of Subjects: 52. Cohort A: MGMT promoter unmethylated (N=32 for 30 evaluable subjects). Cohort B: MGMT promoter methylated (N=20 for 19 evaluable subjects).

Inclusion Criteria:
  Subjects must provide written IRB approved informed consent in accordance with institutional guidelines;
  Be 18 years of age or older on the day of signing the informed consent, and able and willing to comply with all trial procedures;
  Newly-diagnosed brain cancer with histopathological diagnosis of glioblastoma (GBM);
  Karnofsky Performance Status (KPS) rating of ≥70 at baseline;
  Receipt of dexamethasone equivalent dose ≤2 mg per day, stable or decreased for ≥three days prior to Day 0;
  Recovery from the effects of prior GBM surgery as defined by the Investigator;
  ECG with no clinically significant findings as assessed by the Investigator performed within 28 days of signing the informed consent form (ICF);
  Adequate organ function as demonstrated by hematological, renal, hepatic parameters as defined in Table 1 below, obtained within 28 days prior to the first trial treatment;

TABLE 1

| | |
|---|---|
| Absolute neutrophil count (ANC) | ≥1500/mm$^3$ |
| Platelets | ≥100,000/mm$^3$ |
| Hemoglobin | ≥9 g/dL |
| Creatinine OR | ≤1.5 × upper limit ot normal (ULN), OR |
| Measured or calculated creatinine clearance or GFR* | ≥50 mL/min for subject with creatinine level > X institutional ULN |
| Total bilirubin | ≤1.5 × ULN |
| AST (SGOT) and ALT (SGPT) | ≤2.5 × ULN |

*Creatinine clearance should be calculated per Cockcroft-Gault equation

Agree that, during the trial, men will not father a child, and women cannot be or become pregnant if they are of child-bearing potential. Subjects must be of non-child bearing potential (≥12 months of non-therapy-induced amenorrhea, confirmed by follicle stimulating hormone [FSH], if not on hormone replacement); or surgically sterile (vasectomy in males or absence of ovaries and/or uterus in females); or agree to use one highly effective or combined contraceptive methods that result in a failure rate of <1% per year during the treatment period and at least through week 12 after last dose. Periodic abstinence (e.g., calendar, ovulation, symptothermal, or post-ovulation methods) and withdrawal are not acceptable methods of contraception. Examples of contraceptive methods with an expected failure rate of <1% per year include male sterilization and hormonal implants. Alternatively, proper use of combined oral or injected hormonal contraceptives and certain intrauterine devices (IUDs) or two methods (e.g., two barrier methods such as a condom and a cervical cap) may be combined to achieve a failure rate of <1% per year (barrier methods must always be supplemented with the use of aspermicide);
  Ability to tolerate magnetic resonance imaging (MRI).

Exclusion Criteria:
  Presence of greater than 1 cm×1 cm residual tumor enhancement on post-operative MRI;
  Multifocal disease or leptomeningeal disease (LM) disease on post-operative MRI;
  Are not able to start radiation within 42 days of surgical resection of their tumor;
  Receive dexamethasone equivalent dose >2 mg per day;
  Prior treatment with an agent that blocks the PD-1/PD-L1 pathway at any point in the past;
  Receipt of previous approved or investigative immune modulatory agent (for example, anti-TNF, therapeutic anti-cancer vaccines, cytokine treatments (other than G-CSF or erythropoietin), or agents that target cytotoxic T-lymphocyte antigen 4 (CTLA-4), 4-1BB (CD137), PI3K-delta, or OX-40) within 28 days of receiving the first dose of treatment;
  Have received prior treatment with idelalisib at any point in the past;

Past, current, or planned treatment with tumor treatment fields (Optune; NovoTTF); oncolytic viral treatment; or prior exposure to an investigational agent or device, including Gliadel wafer (Carmustine) implant for chemotherapy; within 28 days of receiving the first dose of treatment;

Allergy or hypersensitivity to REGN2810 or to any of its excipients;

History of documented allergic reactions or acute hypersensitivity reaction attributed to antibody treatments;

Ongoing or recent (within 5 years) evidence of autoimmune disease that required treatment with systemic immunosuppressive treatments, which may suggest risk for immune-related adverse events (irAEs), with the exception of: vitiligo, childhood asthma that has resolved, type 1 diabetes, residual hypothyroidism that required only hormone replacement, or psoriasis that does not require systemic treatment;

Diagnosis of immunodeficiency or treatment with systemic immunosuppressive therapy within 28 days prior to the first dose of trial treatment, other than dexamethasone for the underlying disease under investigation, as noted in the inclusion criteria;

Positive serological test for human immunodeficiency virus (HIV), or a history of HIV infection; or positive tests for hepatitis B virus surface antigen (HBV sAg) or hepatitis C virus ribonucleic acid (HCV RNA) indicating active or chronic infection, as these infections may interfere with the ability to mount an appropriate immune response to vaccination;

Current malignancy at another site, with the exception of adequately treated basal or squamous cell skin cancers, or carcinoma of the cervix in situ, with no evidence of disease within 3 years. Cancer survivors who have undergone curative therapy for a prior malignancy, have no evidence of disease for 3 years and are deemed at low risk for recurrence are eligible for the trial;

Receipt of any vaccine within 4 weeks prior to first dose of trial treatment with the exception of the inactivated influenza vaccine, which may be given up to 2 weeks prior;

History of clinically significant, medically unstable disease which, in the judgment of the investigator, would jeopardize the safety of the subject, interfere with trial assessments or endpoint evaluation, or otherwise impact the validity of the trial results (e.g. chronic renal failure, angina, myocardial ischemia or infarction, New York Heart Association (NYHA) class III/IV cardiac disease); or any cardiac pre-excitation syndromes (such as Wolff-Parkinson-White; cardiomyopathy, or clinically significant arrhythmias);

History of pneumonitis within the last 5 years;

Acute or chronic bleeding or clotting disorder that would contraindicate IM injections or use of blood thinners (e.g. anticoagulants or antiplatelet drugs, excluding over-the-counter aspirin or non-steroidal anti-inflammatory drugs, such as ibuprofen) within 2 weeks of Day 0;

Fewer than two acceptable sites available for IM injection considering the deltoid and anterolateral quadriceps muscles. The following are unacceptable sites:

Tattoos, keloids, or hypertrophic scars located within 2 cm of intended treatment site;

Cardioverter-defibrillator or pacemaker (to prevent a life-threatening arrhythmia) that is located ipsilateral to the deltoid injection site (unless deemed acceptable by a cardiologist);

Metal implants or implantable medical device within the intended treatment site (i.e. EP area);

Active drug or alcohol use or dependence that, in the opinion of the Investigator, would interfere with adherence to trial requirements;

Imprisonment, or compulsory detainment (involuntary incarceration) for treatment of either a psychiatric or physical (i.e. infectious disease) illness;

Pregnant or current breastfeeding;

As determined by the Investigator, any medical or psychological or non-medical condition that might interfere with the subject's ability to participate or affect the safety of the subject.

Dosage and Administration

Investigational Drug Products are provided in Table 2.

TABLE 2

| Product | Formulation | Unit |
|---|---|---|
| INO-5401 | 10.0 ± 0.5 mg/mL total plasmid (pGX1108, pGX1404, pGX1434; 1:1:1 w/w) in 165 mM sodium chloride and 16.5 mM sodium citrate | 1.4 mL/ 2-mL vial |
| INO-9012 | 10.0 ± 0.5 mg/mL pGX6001 in water for injection | 0.2 mL/ 2-mL vial |
| REGN2810 | REGN2810 is supplied as a sterile liquid solution of 5.5 mL in a 10 mL glass vial (50 mg/mL) for IV administration. REGN2810 may also be supplied as a sterile liquid solution of 7.44 mL in a 10 mL glass vial (50 mg/mL) for IV administration. | 5.5 mL/ 10-mL vial Or 7.44 mL/ 10-mL vial |

The active pharmaceutical ingredients (APIs) in INO-5401 are DNA plasmid sequences that were designed and constructed using proprietary synthetic consensus (SynCon®) technology. This process involves synthetically deriving consensus genes across multiple strains and optimizing DNA inserts at the genetic level to allow high expression in human cells. The INO-5401 plasmids are as follows:

pGX1108, a plasmid for expression of prostate-specific membrane antigen (PSMA; SEQ ID NO: 28). 3 mg of pGX1108 will be present in each 10 mg dose of trial treatment (INO-5401+INO-9012).

pGX1404, a plasmid for expression of Wilms' tumor gene-1 (WT1) antigen (SEQ ID NO: 26). 3 mg of pGX1404 will be present in each 10 mg dose of trial treatment.

pGX1434, a plasmid for expression of human telomerase reverse transcriptase (hTERT) (SEQ ID NO: 20). 3 mg of pGX1434 will be present in each 10 mg dose of trial treatment.

The API in drug product INO-9012 is pGX6001, a DNA plasmid for expression of human IL-12 p35 (SEQ ID NO: 22) and p40 (SEQ ID NO: 25) subunit proteins. 1 mg of pGX6001 will be present in each 10 mg dose of trial treatment. Both DNA plasmid products INO-5401 and INO-9012, are administered using a syringe and the investigational CELLECTRA® 2000 electroporation (EP) device.

Cemiplimab-rwlc (REGN2810) is a covalent heterotetramer consisting of two disulfide-linked human heavy chains, each of which is covalently bonded through disulfide linkages to a human kappa light chain. The antibody possesses an approximate molecular weight of 143.6 kDa based on the primary sequence. There is a single N-linked glycosylation site on each heavy chain, located within the constant region in Fc portion of the molecule.

The REGN2810 heavy chain possesses an IgG4 isotype-constant region. The variable domains of the heavy and light chains combine to form PD-1 binding site within the antibody. Antibody generation by VelocImmune® mice is carried out using standard techniques after immunization with PD-1. The genes encoding the heavy and light chains of REGN2810 were introduced into CHO cells, and a stable expression cell line with a higher titer (Cell Line 2) was developed for this antibody. For both cell lines, the recombinant CHO cells were grown in suspension culture and chemically induced to initiate antibody expression and secretion into the cell culture medium. Antibody is harvested via filtration and purified though a series of preparative column chromatographic and filtration steps to generate drug substance. Drug substance is then formulated and sterile-filtered to produce the final drug product.

REGN2810 (50 mg/mL) is formulated in an aqueous buffered solution at pH 6.0 containing 10 mM histidine, 5% (w/v) sucrose, 1.5% (w/v) L-proline, and 0.2% (w/v) polysorbate 80. REGN2810 is supplied as a sterile liquid solution of 5.5 mL in a 10 or 20 mL glass vial for IV administration. A maximum volume of 5.0 mL can be withdrawn from each vial containing 250 mg of REGN2810. Seven mLs are needed to provide a 350 mg dose of REGN2810, thus 2 vials must be used when supplied with the 5 mL vials. REGN2810 (50 mg/mL) may also be supplied as a sterile liquid solution of 7.44 mL in a 10 or 20 mL glass vial for IV administration. A maximum volume of 7.0 mL can be withdrawn from each vial containing 350 mg of REGN2810.

Treatment

Subjects who meet all of the inclusion criteria and none of the exclusion criteria started immunotherapy with REGN2810 and INO-5401+INO-9012 on Day 0. REGN2810 was administered IV every three weeks at a dose of 350 mg per dose, in the absence of dose holding, until disease progression as defined by iRANO, unacceptable toxicity, withdrawal of consent, or death. INO-5401 and INO-9012 IM followed by EP was administered every three weeks for four doses, and then every 9 weeks, at a dose of 10 mg/DNA per dose, in the absence of dose holding, until disease progression as defined by iRANO, unacceptable toxicity, withdrawal of consent, or death. RT began no later than 42 days after surgical intervention and approximately 1 to 2 weeks after Day 0. RT continued for approximately three weeks. The total dose of RT was 40 Gy given over 3 weeks.

Daily TMZ with radiation therapy (TMZ/RT) began no later than 42 days after surgical intervention and approximately 2 weeks after Day 0. TMZ/RT continued for approximately three weeks. TMZ was given at a dose of 75 mg/m²/dose, in the absence of dose reduction. Subjects should then receive maintenance (adjuvant) TMZ for an additional 6 cycles. Cohort B received TMZ following radiotherapy for up to six cycles. Maintenance (adjuvant) TMZ was administered to subjects in Cohort B for the first 5 days of a 28-day cycle at 150-200 mg/m²/dose, following peripheral blood count recovery from TMZ/RT per standard guidelines TMZ treatment.

Day 0 (first dose of INO 5401, INO 9012 and REGN2810) was at least 14 days after completion of resection of primary tumor and the subject has recovered from surgery, but no later than post-operative day 28.

For subjects who discontinued one therapy (either INO-5401+INO-9012 or REGN2810) for reasons other than progression, the other therapy was allowed to continue after consultation with the Medical Monitor.

FIG. 1 illustrates the trial design for Cohorts A and B.

INO-5401 (3 mg each of hTERT, WT-1 and PSMA plasmids) combined with 1 mg INO-9012 (IL-12), for a total of 10 mg of DNA, administered via intramuscular (IM) injection followed by electroporation (EP) with CELLECTRA® 2000 device, and delivered every three weeks for four doses, then every 9 weeks.

Chemoradiation: Radiation (RT) given in a hypofractionated schedule (40 Gy over three weeks)

Temozolomide (TMZ) concurrent with radiation (Cohorts A and B), followed by six maintenance (adjuvant) cycles (Cohort B only)

Cemiplimab-rwlc (REGN2810) was administered IV at a dose of 350 mg every three weeks (Q3W) over approximately 30 minutes, starting at Day 0, and continued until disease progression as defined by iRANO, unacceptable toxicity, withdrawal of consent, or death.

INO-5401 is a mixture of three separate synthetic plasmids that target WT1, PSMA and hTERT proteins. Each plasmid was dosed at 3 mg DNA, for a total of 9 mg DNA per dose of INO-5401. INO-5401 was administered IM at Day 0, Week 3, Week 6, and Week 9, and then every 9 weeks thereafter, and continued until disease progression as defined by iRANO, unacceptable toxicity, withdrawal of consent, or death. INO-9012 is a synthetic plasmid that expresses human IL-12, and is dosed at 1 mg DNA, and was administered IM together with INO-5401. The total dose of DNA in each dose of INO-5401+INO-9012 when mixed and administered together was 10 mg. INO-5401 (3 mg each of hTERT, WT-1 and PSMA plasmids) combined with 1 mg INO-9012 (IL-12), for a total of 10 mg of DNA, was administered via intramuscular (IM) injection followed by electroporation (EP) with CELLECTRA® 2000 device, and delivered every three weeks for four doses, then every 9 weeks.

All subjects received a total of 40 Gy in 15 fractions (three weeks).

Hypofractionated radiation therapy (hfRT) began no later than 42 days after surgery. Radiotherapy was given for three weeks.

All patients received TMZ, regardless of MGMT methylation status, unless clinically contraindicated, during radiotherapy. TMZ was administered at 75 mg/m² daily by mouth for 21 days concomitant (7 days a week for three weeks) with hfRT therapy.

Following radiation therapy, subjects with MGMT promoter methylation (Cohort B) continued TMZ maintenance therapy at a starting dose of 150 mg/m²/day for 6 cycles on the first 5 days of a 28-day cycle (5 days "on," 23 days "off"), and increased each maintenance cycle by 50 mg/m²/dose to a maximum of 200 mg/m²/dose, in the absence of hematologic toxicity. Maintenance (adjuvant) TMZ started approximately four weeks after the last dose of RT (±3 days) and following peripheral blood count recovery, per TMZ treatment guidelines. The dose was determined using actual body surface area (BSA) as calculated in square meters at the beginning of each treatment cycle.

The daily dose was rounded to the nearest 5 mg.

For detailed information on efficacy evaluations/endoints ELISpot, lytic granule loading, safety assessments, medical and clinical assessments, physical assessments, medical post-treatment reaction assessment, vital signs, weight, height, and body mass index, 12-lead EGC, pregnancy test, laboratory evaluations, peripheral blood immunogenicity assessments, tissue immunology, clinical assessments, documentation of overall survival and progression, rano and irano (immunotherapy) response assessment in neuro-oncology), nanoscale neurological assessment in neuro-oncology, statistical and analytical plan, statistical hypothesis, analysis populations and datasets, subject disposition, and safety data are described in WO 2021/092019, the entirety of which is incorporated herein by reference.

Exploratory Analyses

Exploratory tumor genetics and/or biomarker responses were presented using descriptive statistics at each time point and as changes from baseline for the mITT population and per protocol population.

Results

Demographics of enrolled patients at the 18-month analysis timepoint are shown in FIG. 2A (Demographics Table). Updated patient demographics as assessed at the 42-month analysis timepoint are provided in FIG. 2B. Assessment of gene transcripts from tumors at diagnosis confirmed expression of antigens encoded by INO-5401 and a diverse immune gene profile. 5 of 47 subjects (811%) with available tissue for assessment exhibited transcript expression of one or more Tumor Associated Antigens encoded by INO-5401 (WT1, PSMA and hTERT). 43 of 47 subjects (89%) with available tissue for assessment exhibited transcript expression of two (2) or more Tumor Associated Antigens encoded by INO-5401 (WT1, PSMA and hTERT). 19 of 47 subjects (40%) exhibited transcript expression of all three Tumor Associated Antigens. No subject exhibited PD-1 expression without concomitant PD-L1 expression. 27 of 47 subjects (57%) exhibited PD-L1 expression with no concomitant PD-1 expression. 20 of 47 subjects (43%) showed co-expression of PD-1 and PD-L1. Normalized transcript read counts >1 were considered "positive."

MRI Imaging

Several patients have experienced pseudo-progression, with radiographic evidence of progression on MRI without evidence of tumor on repeat biopsy. Images from example patients demonstrate increase in MRI signal at timepoints following first dose of INO-5401+INO-9012 and cemiplimab-rwlc, suggestive of edema or tumor. Biopsy on several patients shows treatment-related changes with necrosis and mixed inflammation; absence of mitotic activity; and no evidence of viable tumor. Representative images from two patients are presented in FIG. 3.

ELISpot

ELISpot is/was employed to give a qualitative measure of whether antigen specific T cells are present in a peripheral blood mononuclear cell (PBMC) sample. PBMCs are collected from subjects at study weeks 0, 3, 6, 9, 12, and 24 and assayed by IFN-g ELISpot. At the 12-month data cut-off, antigen specific IFNg spot forming units (SFU) per million PBMCs are shown from before (pre) and the highest magnitude (peak) after treatment with INO-5401 and cemiplimab-rwlc from 8 subjects with sample to week 24 (FIG. 4). Each subject is represented by an open circle, bars represent the mean. The difference from pre to peak, delta, is shown for each antigen graph as well as together for 11 subjects assayed and for the 8 with sample available to week 24. INO-5401 is the sum of WT1, PSMA and hTERT. Box plots extend from the 25th to 75th percentile, with a horizontal line at the median, and "+" at the mean. ELISpot results support the combination of INO-5401 and cemiplimab-rwlc are immunogenic-with IFN-g magnitudes above baseline to all 3 antigens in 5/11 subjects and to at least one antigen in 9 subjects as shown in FIG. 4.

Figure 16A:
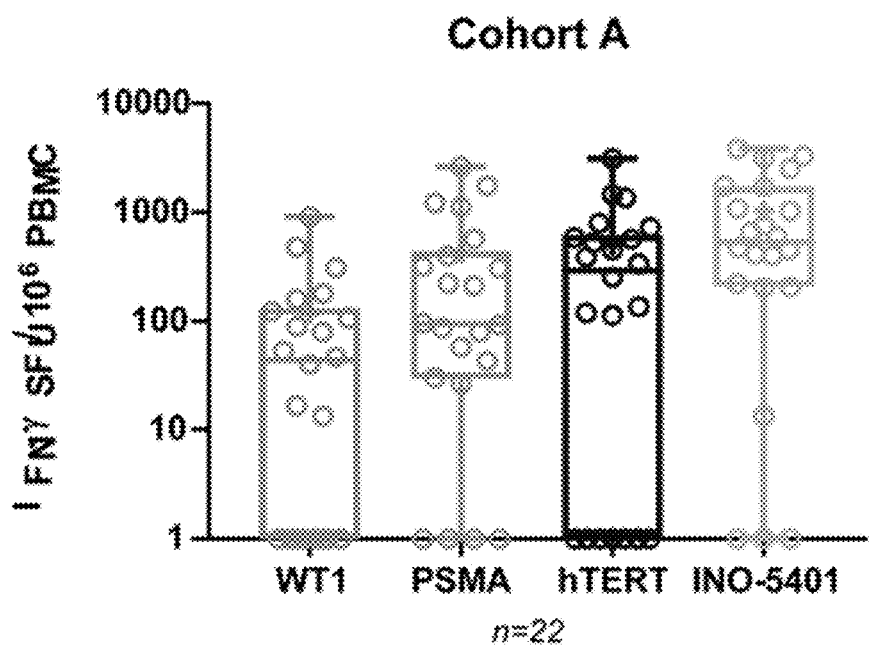
FIG. 16A and FIG. 16B provide ELISpot results by Cohort at the 18-month data cut-off. In Cohort A, 19/22 (86%) subjects tested to date had an IFN-g magnitude above baseline to one or more of the antigens INO-5401 (FIG. 16A). In Cohort B, 16/17 (94%) subjects tested to date had an IFN-g magnitude above baseline to one or more of the antigens in INO-5401 (FIG. 16B). Baseline values from the peak timepoint following treatment are plotted. Samples collected Q3 weeks×4 and then Q12 weeks.
Figure 16B:
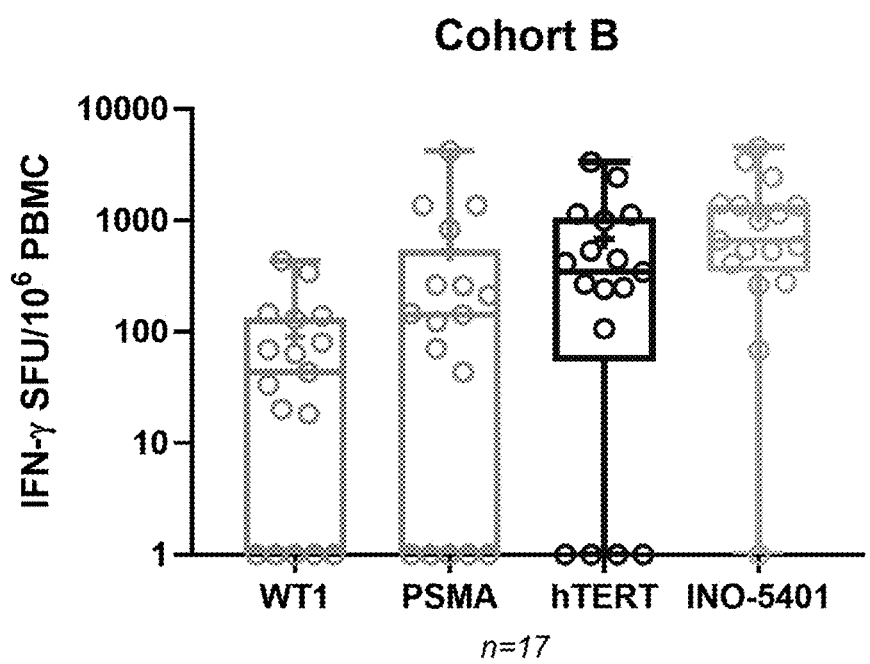

Assessment of post-INO-5401 peripheral immune responses by Cohort at the 18-month data cut-off revealed antigen-specific T cell responses by Interferon gamma ELISpot (cytokine production in response to each component of INO-5401). Results of assessment of post-INO-5401 peripheral immune responses by ELISpot at by Cohort are provided in FIG. 16A and FIG. 16B. Baseline values from the peak timepoint following treatment are plotted. In Cohort A, 19/22 (86%) subjects tested to date had an IFN-g magnitude above baseline to one or more of the INO-5401 antigens (FIG. 16A). In Cohort B, 16/17 (94%) subjects tested to date had an IFN-g magnitude above baseline to one or more of the INO-5401 antigens (FIG. 16B).

Lytic Granule Loading

Figure 5A:
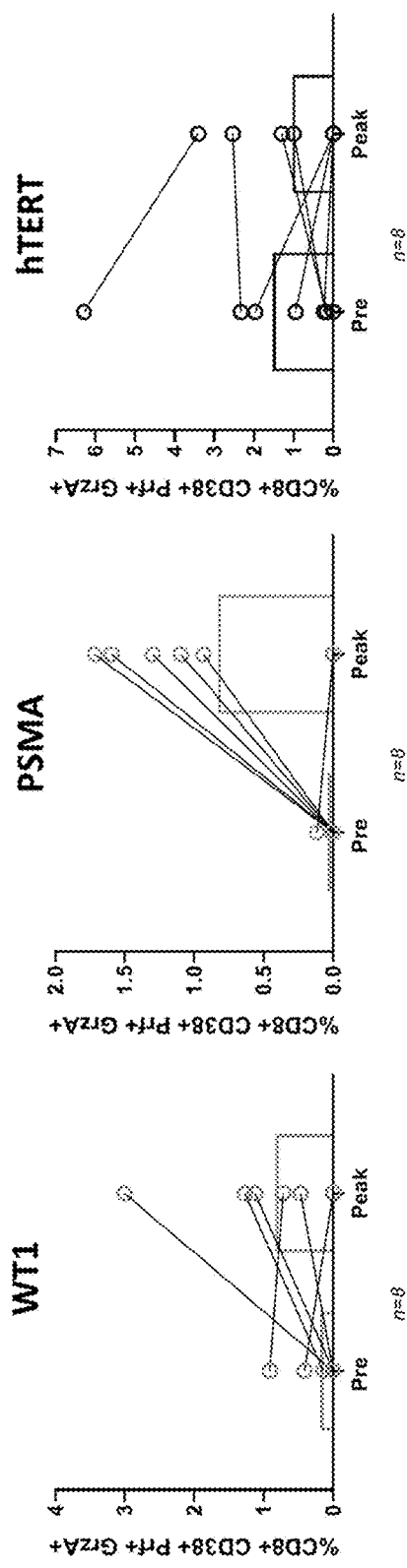
FIG. 5A, FIG. 5B, and FIG. 5C show the lytic granule loading assay results demonstrating frequencies of live, antigen-specific, activated (CD38+) CD3+CD8+ T cells with lytic potential (expressing Granzyme A, Perforin) obtained at the 12-month data cut-off.
Figure 5C:
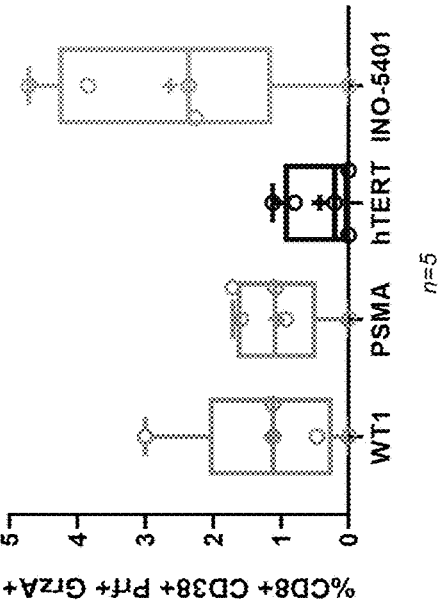
Figure 5B:
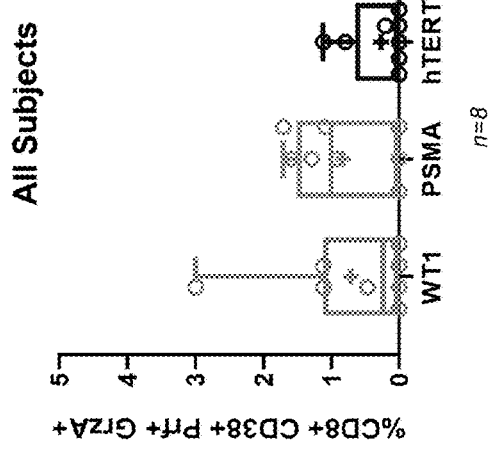

A lytic granule loading assay was performed to explore the activation status and lytic potential of antigen specific T cells present in PBMC samples collected from subjects at study weeks 0, 3, 6, 9, 12, and 24. PBMCs were stimulated with overlapping peptide libraries for INO-5401 antigens (hTERT, PSMA and WT1) or relevant controls in the absence of any exogenous cytokines. After 5 days, cells were stained with antibodies and assessed by flow cytometry. Frequencies of live, antigen-specific, activated (CD38+) CD3+CD8+ T cells with lytic potential (expressing Granzyme A, Perforin) are shown from before treatment at baseline (pre) and the highest magnitude (peak) after treatment with INO-5401 and cemiplimab-rwlc from 8 subjects for each antigen (FIG. 5A). Each subject is represented by an open circle, bars represent the mean. The difference from pre to peak, delta, is shown for each antigen as well as INO-5401 at the 12-month data cut-off for 8 subjects assayed (FIG. 5B) and for the 5/8 subjects with sample available to week 12 (FIG. 5C). INO-5401 is the sum of WT1, PSMA and hTERT. Box plots extend from the 25th to 75th percentile, with a horizontal line at the median, and "+" at the mean. Five subjects had a frequency of activated CD8+T cells with lytic potential (CD38+Prf+GrzA+) above baseline (pre) to more than one antigen; three subjects had a frequency of activated CD8+T cells with lytic potential (CD38+Prf+GrzA+) above baseline to all three antigens. Three subjects did not have a response above baseline to any antigen at any time.

Figure 17A:
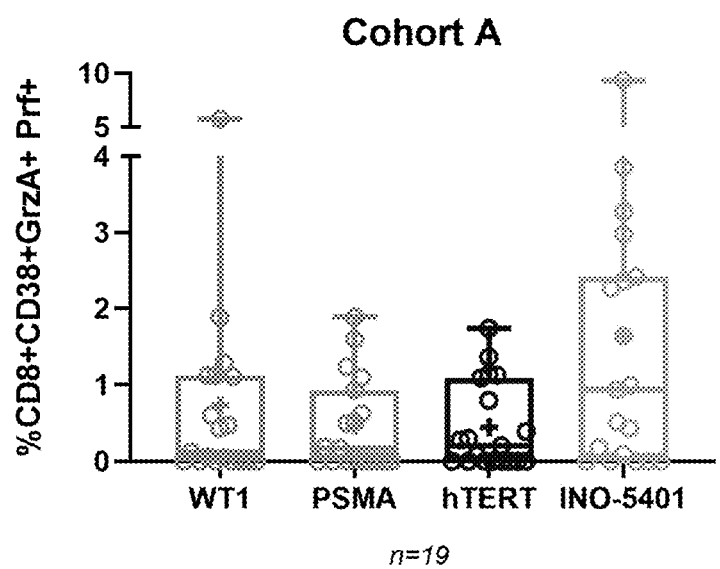
FIG. 17A and FIG. 17B provide results of assessment of post-INO-5401 peripheral immune responses by Cohort by flow cytometry (the expansion of antigen specific CD8+ T cells with lytic potential) at the 18-month data cut-off. In Cohort A, 13/19 (68%) subjects tested to date had a frequency of CD38+GrzA+Prf+CD8+T cells above baseline to one or more of the antigens in INO-5401 (FIG. 17A). In Cohort B, 8/10 (80%) subjects tested to date had a frequency of CD38+GrzA+Prf+CD8+T cells above baseline to one or more of the antigens in INO-5401 (FIG. 17B). Baseline values from the peak timepoint following treatment are plotted. Samples were collected Q3 weeks×4 and then Q12 weeks.
Figure 17B:
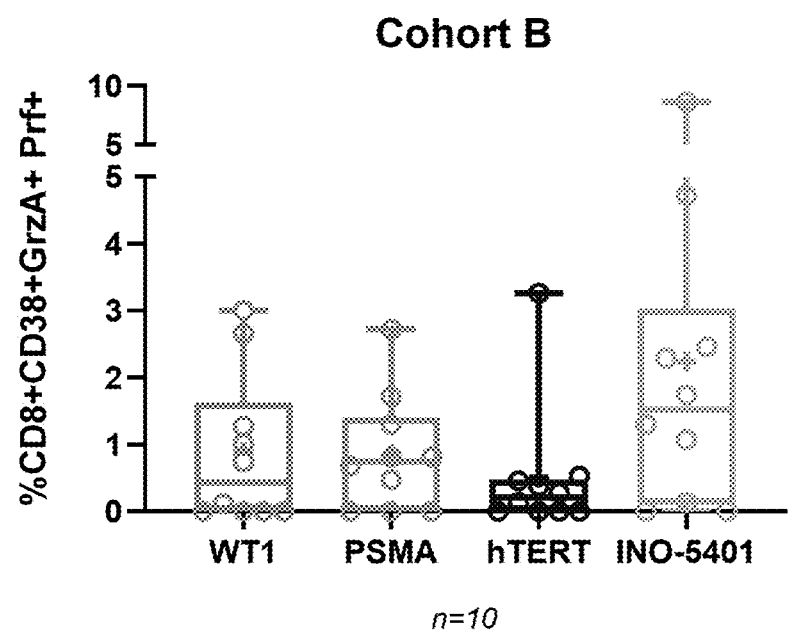

Assessment of post-INO-5401 peripheral immune responses by Cohort at the 18-month data cut-off revealed antigen-specific T cell responses by flow cytometry (the expansion of antigen specific CD8+T cells with lytic potential). In Cohort A, 13/19 (68%) subjects tested to date had a frequency of CD38+GrzA+Prf+CD8+T cells above baseline to one or more of the INO-5401 antigens (FIG. 17A). In Cohort B, 8/10 (80%) subjects tested to date had a frequency of CD38+GrzA+Prf+CD8+T cells above baseline to one or more of the INO-5401 antigens (FIG. 17B). Samples were collected Q3 weeks×4 and then Q12 weeks. Baseline values from the peak timepoint following treatment are plotted.

Progression-Free Survival

FIG. 6 shows the visual representation of the Kaplan-Meier estimator of the progression-free survival at six months (PFS6) for Cohort A, patients with the O6-methylguanine methyltransferase gene promoter unmethylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 7 shows the visual representation of the Kaplan-Meier estimator of the progression-free survival at six months (PFS6) for Cohort B, patients with the O6-methylguanine methyltransferase gene promoter methylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 8 shows the visual representation of the Kaplan-Meier estimator of the progression-free survival at six months (PFS6) for Cohort A and Cohort B, patients with the O6-methylguanine methyltransferase gene promoter unmethylated or methylated in their tumor cells. The curve shows the probability of an event at a certain time interval. The probability of the event is represented numerically on the y-axis, and the time interval on the x-axis. The event shown is progression-free survival. Progression-free survival is the absence of progression of disease at a given time point for a given subject.

FIG. 9 shows the tabular representation of the Kaplan-Meier estimator of the progression-free survival at six months (PFS6) for Cohort A, Cohort B, and both cohorts combined. The total number of subjects per cohort, number of events, estimation of the event (PFS6), and the 95% confidence interval (CI) in which the numerical estimate of the event (PFS6) exists are all provided.

Confirmed progressive disease (PD) is determined by confirmation by consecutive PD scan ≥4 weeks from original PD event, or progressed according to biopsy surgery. Subjects who terminated for any reason prior to 6 months other than PD included as confirmed progressive events, including two (2) subjects in Cohort B who came off-study at week three (3), and declined long-term follow-up.

Overall Survival

All efficacy analyses (OS12, OS18, & Kaplan-Meier) were analyzed on subjects in the modified intent-to-treat (mITT) population which is defined as all subjects who received at least one dose of planned treatment. Overall Survival at twelve months (OS12) was tabulated as the proportion of subjects alive at 12 months out of all subjects at risk of death at the start of the study. Subjects who dropped out were considered failures (that is deaths). All subjects in Cohort A who dropped out prior to 12 months also died before 12 months of follow-up. The 95% confidence intervals (CIs) are calculated using the Clopper-Pearson exact method. Overall Survival at eighteen months (OS18) was tabulated as the proportion of subjects alive at 18 months out of all subjects at risk of death at the start of the study. The 95% confidence intervals (CIs) are calculated using the Clopper-Pearson exact method.

Figure 10A:
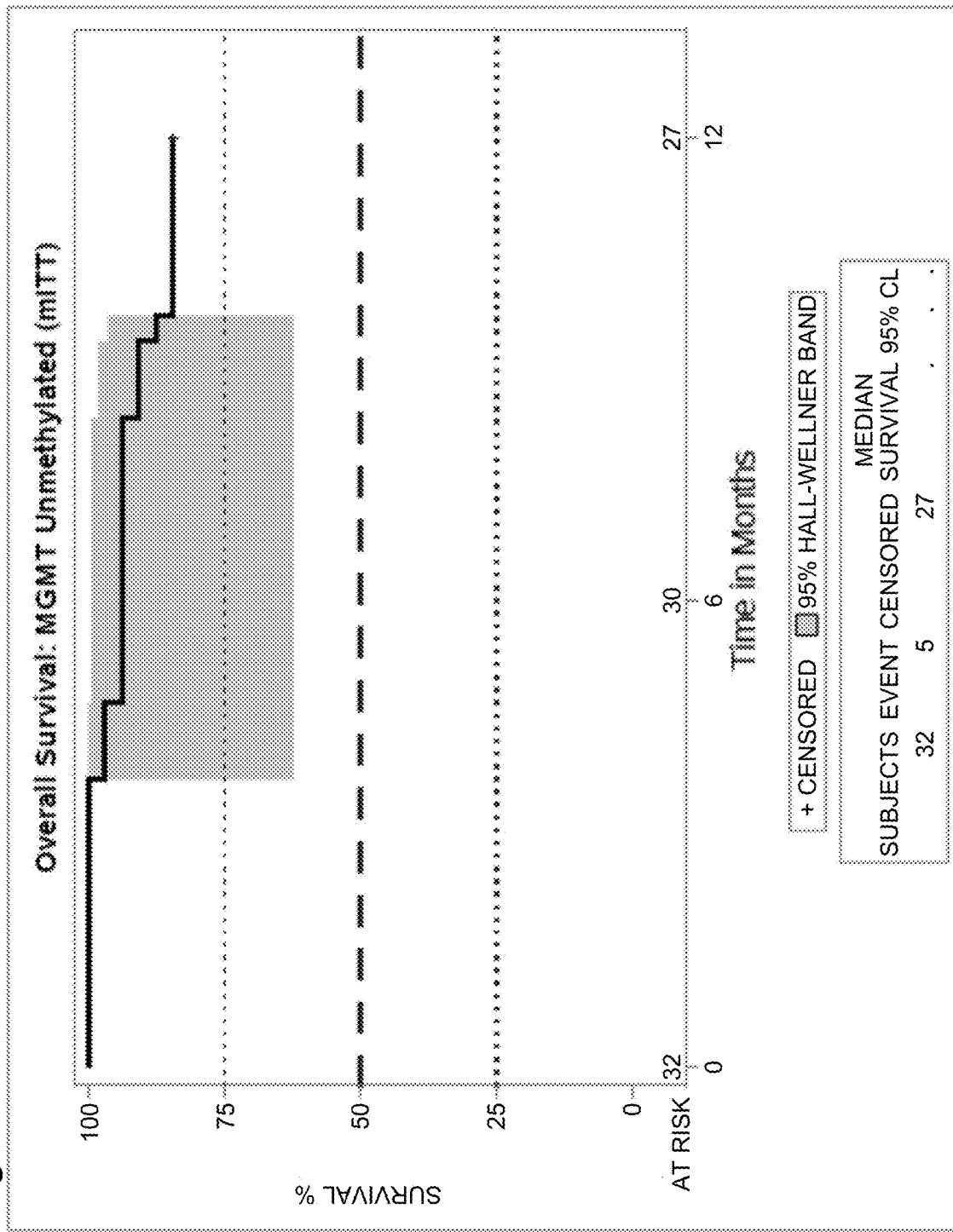
FIG. 10A shows the visual representation of the Kaplan-Meier estimator of the overall survival probability over twelve months for Cohort A, for patients with the O6-methylguanine methyltransferase gene promoter unmethylated in their tumor cells. The stepwise curve shows the probability of surviving up to and beyond a specific time point. The survival probability is represented numerically on the y-axis, and survival time in days on the x-axis.
Figure 10B:
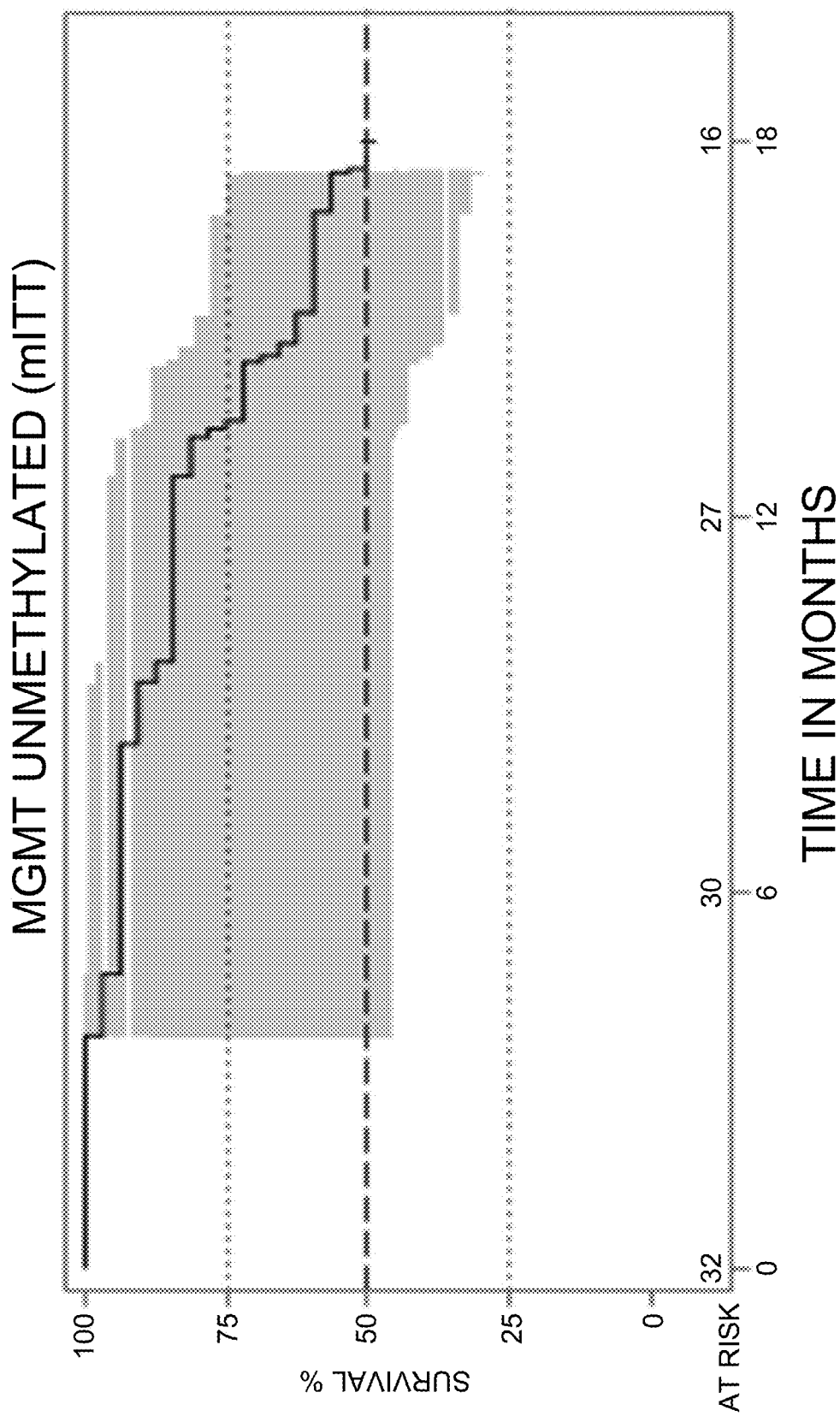
FIG. 10B shows the visual representation of the Kaplan-Meier estimator of the overall survival probability over eighteen months for Cohort A, for patients with the O6-methylguanine methyltransferase gene promoter unmethylated in their tumor cells. The stepwise curve shows the probability of surviving up to and beyond a specific time point. The survival probability is represented numerically on the y-axis, and survival time in days on the x-axis. Median follow-up in Cohort A is 17.8 months. mITT includes any subject who received ≥1 dose of study therapy. Shading represents confidence band on point estimate for survival at that timepoint.

FIG. 10A shows the visual representation of the Kaplan-Meier estimator of the overall survival probability over twelve months for Cohort A, for patients with the O6-methylguanine methyltransferase gene promoter unmethylated in their tumor cells. The stepwise curve shows the probability of surviving up to and beyond a specific time point. The survival probability is represented numerically on the y-axis, and survival time in days on the x-axis. FIG. 10B shows the visual representation of the Kaplan-Meier estimator of the overall survival probability over eighteen months for Cohort A, for patients with the O6-methylguanine methyltransferase gene promoter unmethylated in their tumor cells. The stepwise curve shows the probability of surviving up to and beyond a specific time point. The survival probability is represented numerically on the y-axis, and survival time in days on the x-axis. Median follow-up in Cohort A is 17.8 months. mITT includes any subject who received ≥1 dose of study therapy. Shading represents confidence band on point estimate for survival at that timepoint.

Figure 10C:
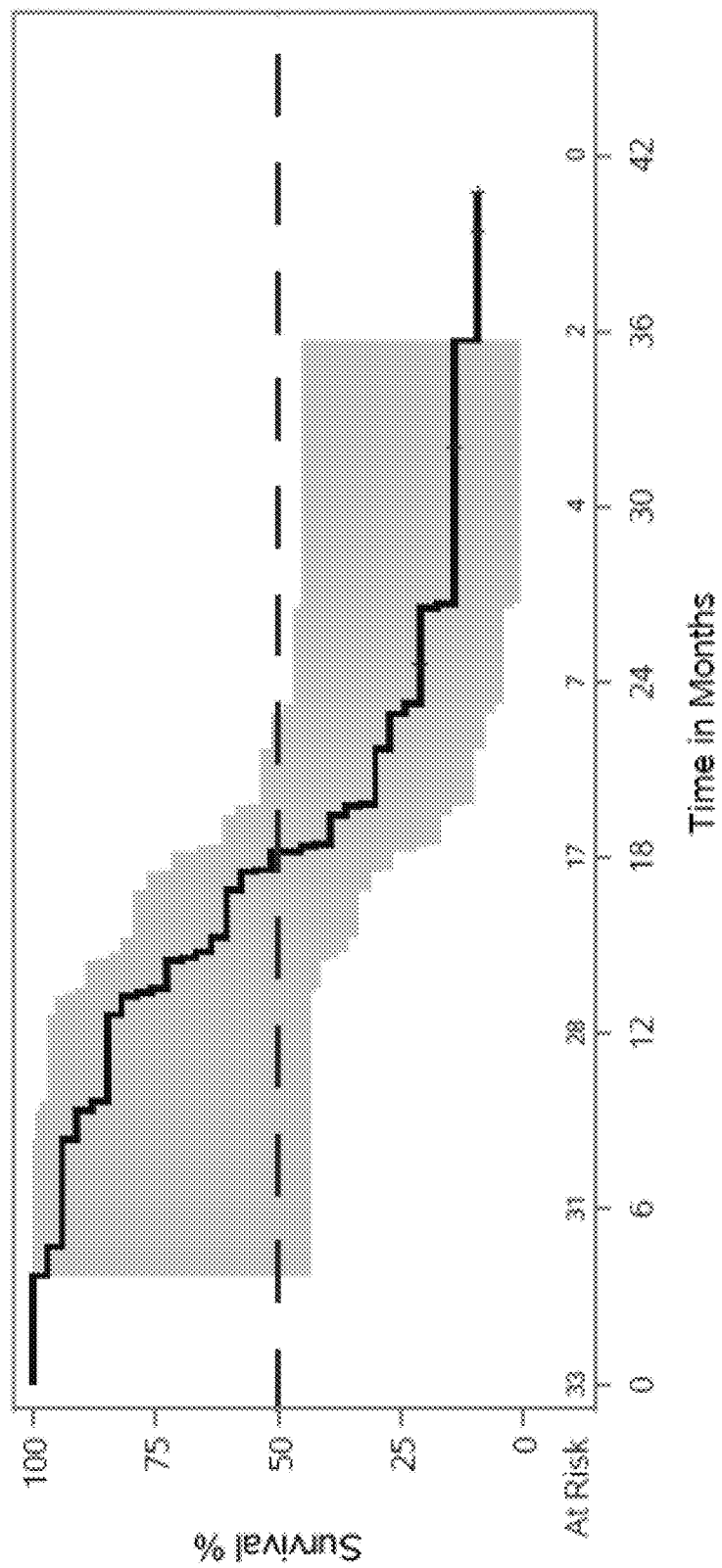
FIG. 10C shows the visual representation of the Kaplan-Meier analysis of the overall survival for MGMT unmethylated (miTT) patients up to 42 months (cohort A).
Figure 11A:
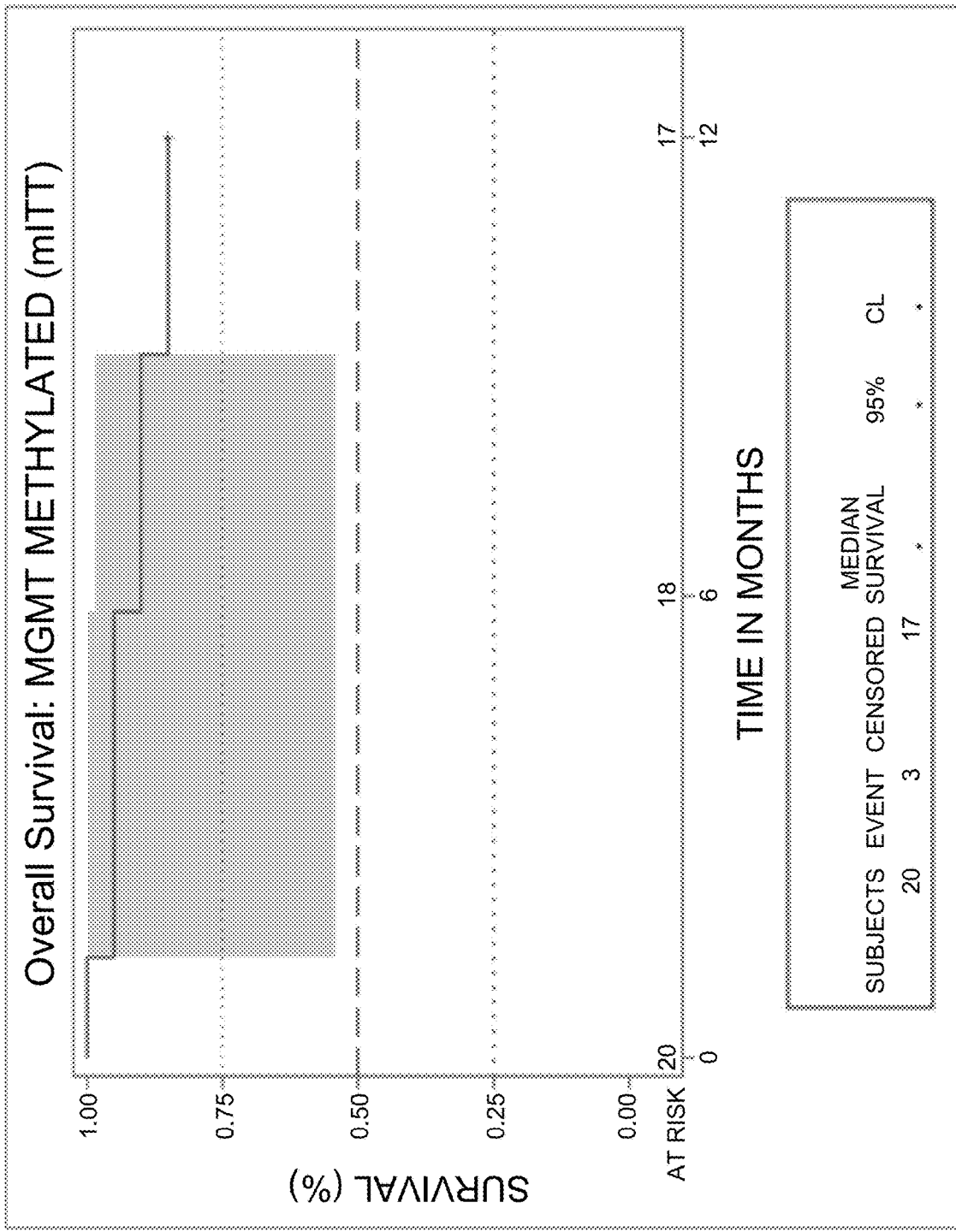
FIG. 11A shows the visual representation of the Kaplan-Meier estimator of the overall survival probability over twelve months for Cohort B, for patients with the O6-methylguanine methyltransferase gene promoter methylated in their tumor cells. The stepwise curve shows the probability of surviving up to and beyond a specific time point. The survival probability is represented numerically on the y-axis, and survival time in days on the x-axis.
Figure 11B:
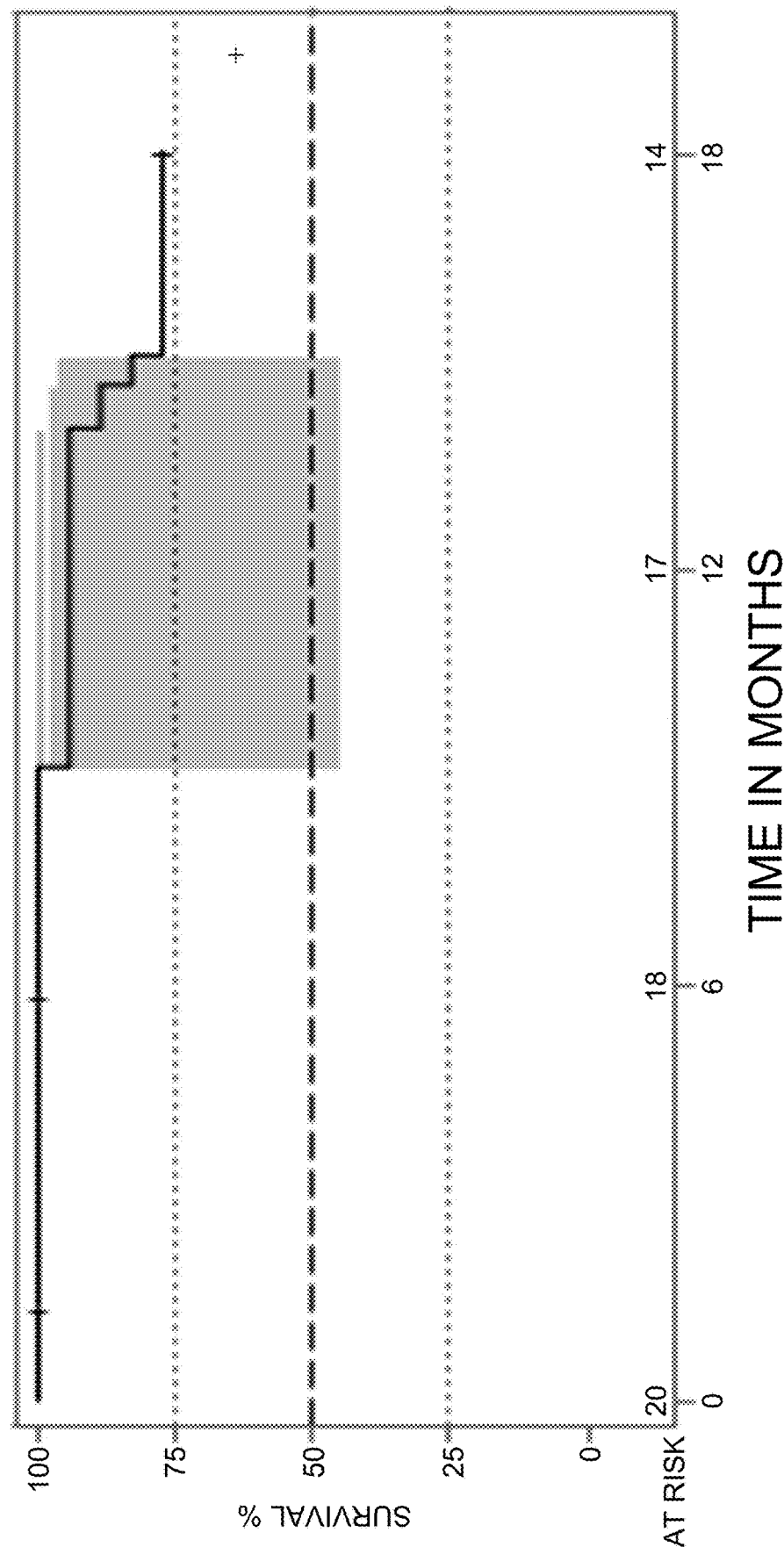
FIG. 11B shows the visual representation of the Kaplan-Meier estimator of the overall survival probability over eighteen months for Cohort B, for patients with the O6-methylguanine methyltransferase gene promoter methylated in their tumor cells. The stepwise curve shows the probability of surviving up to and beyond a specific time point. The survival probability is represented numerically on the y-axis, and survival time in days on the x-axis. Median follow-up in Cohort B is 15.6 months. Censored; two subjects in Cohort B withdrew consent for follow-up at Week 3. mITT includes any subject who received ≥1 dose of study therapy. Shading represents confidence bands on point estimate for survival at that timepoint.
Figure 11C:
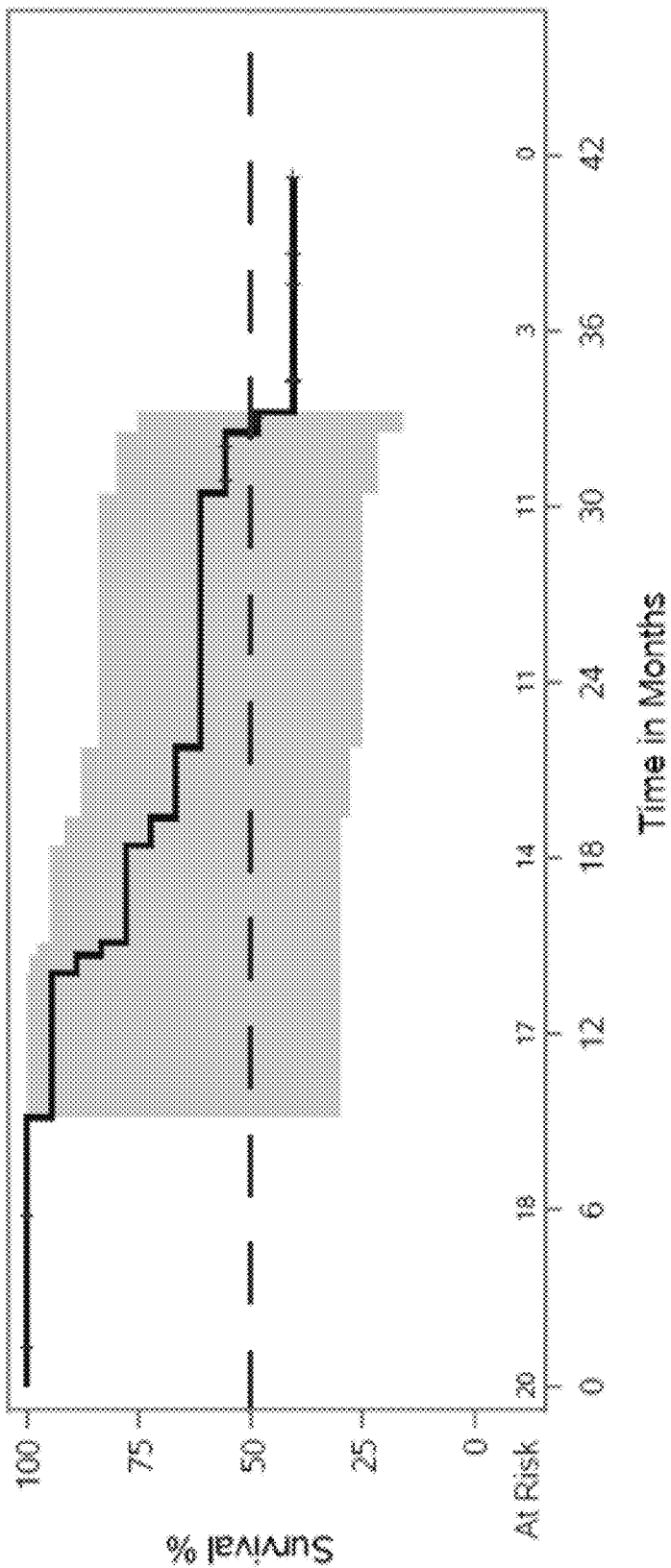
FIG. 11C shows the visual representation of the Kaplan-Meier analysis of the overall survival for MGMT methylated (miTT) patients up to 42 months (cohort B).

FIG. 10C shows the visual representation of the Kaplan-Meier analysis of the overall survival for MGMT unmethylated (miTT) patients up to 42 months (cohort A). At risk=number who have not met OS endpoint or have not been censored by a given timepoint. NR=not reached. FIG. 11A shows the visual representation of the Kaplan-Meier estimator of the overall survival probability over twelve months for Cohort B, for patients with the O6-methylguanine methyltransferase gene promoter methylated in their tumor cells. The stepwise curve shows the probability of surviving up to and beyond a specific time point. The survival probability is represented numerically on the y-axis, and survival time in days on the x-axis. FIG. 11B shows the visual representation of the Kaplan-Meier estimator of the overall survival probability over eighteen months for Cohort B, for patients with the O6-methylguanine methyltransferase gene promoter methylated in their tumor cells. The stepwise curve shows the probability of surviving up to and beyond a specific time point. The survival probability is represented numerically on the y-axis, and survival time in days on the x-axis. Median follow-up in Cohort B is 15.6 months. Censored; two subjects in Cohort B withdrew consent for follow-up at Week 3. mITT includes any subject who received ≥1 dose of study therapy. Shading represents confidence bands on point estimate for survival at that timepoint. FIG. 11C shows the visual representation of the Kaplan-Meier analysis of the overall survival for MGMT methylated (miTT) patients up to 42 months (cohort B). At risk=number who have not met OS endpoint or have not been censored by a given timepoint. NR=not reached.

FIG. 12 shows the visual representation of the Kaplan-Meier estimator of the overall survival probability over twelve months for Cohorts A+B combined. The stepwise curve shows the probability of surviving up to and beyond a specific time point. The survival probability is represented numerically on the y-axis, and survival time in days on the x-axis.

FIG. 13 shows the efficacy data of the overall survival at 12 months and 18 months for Cohort A, for Cohort B, and combined. The figure shows the total number of subjects who were reported alive at 12 months and at 18 months. The total number of subjects, estimation of the event (OS12 or OS18), and the 95% confidence interval (CI) in which the numerical estimate of the event (OS12 or OS18) exists are all provided. The 95% CI were calculated using the exact Clopper-Pearson method.

Median overall survival values for Cohorts A and B for over a period of 42 months are provided in Table A.

TABLE A

| | | |
|---|---|---|
| Median OS; unmethylated (A) | 17.9 months (14.5-19.8) | Historical 14.6-16 months |
| Media OS; methylated (B) | 32.5 months (18.4-NR) | Historical 23.2-25 months |
| Median OS; combined (A + B) | 19.5 months (16.9-23.3) | — |

Conclusions

In patients with newly diagnosed GBM, INO-5401+INO-9012 in combination with cemiplimab-rwlc, given with radiation and temozolomide, has an acceptable safety profile, is immunogenic and is potentially efficacious in patients with newly diagnosed GBM. Common AEs included injection site administration events; ≥Grade 3 AEs were primarily due to TMZ or radiation, and immune-related AEs were consistent with the profile of cemiplimab-rwlc. SAEs were consistent with those seen in patients with GBM (seizure).

Antigen-specific T cell responses were seen to one or more of the antigens included in INO-5401 in almost all patients tested to date. PFS6 exceeds that of historical controls in this study, in patients with and without MGMT promotermethylation, and OS12 exceeds that of historical controls in patients without MGMT promoter methylation [Stupp R, Mason W P, van den Bent M J, et al. Radiotherapy plus concomitant and adjuvant temozolomide for glioblastoma. N Engl J Med 2005, 352:987-996]. Treatment of subjects without methylation of the promoter region of the MGMT gene with INO-5401 resulted in an Overall Survival rate of 50% at 18 months following resection of tumor.

Example 2: Biomarker Analysis

Biomarker assessments were performed from peripheral and tissue samples referenced in the phase 1/2 trial described in Example 1, above, and collected per lab manual instructions. Immunohistochemical assessment of the expression of the hTERT, WT1 and/or PSMA proteins within tissue samples from enrolled subjects occurred contingent on the presence of sufficient sample quantity and continued relevance as supported by available data. IDH-1 status was performed on tumor tissue if available. MicroRNA signatures in blood plasma and/or sera were assessed in order to determine disease and/or therapy specific signatures that predict disease course and/or response to treatment with INO-5401 as well as INO-5401 driven changes. RNAseq may be used for this method.

MicroRNA Signature
miRNA as a Novel Prognostic Marker of Clinical Response to INO-5401 for Treatment of Glioblastoma Plasma samples taken from Cohort A in trial described in Example 1 were assessed in a post-hoc fashion for the presence of miRNAs using an RNA sequencing platform for the purpose of exploration of dynamic regulation of miRNAs during the treatment process. However, and surprisingly, analysis of miRNA data taken prior to treatment with INO-5401 suggested that the presence and amount of particular miRNAs could be prognostic for response to treatment in the form of survival out to 18 months post tumor resection.

Figures 18A, 18B:
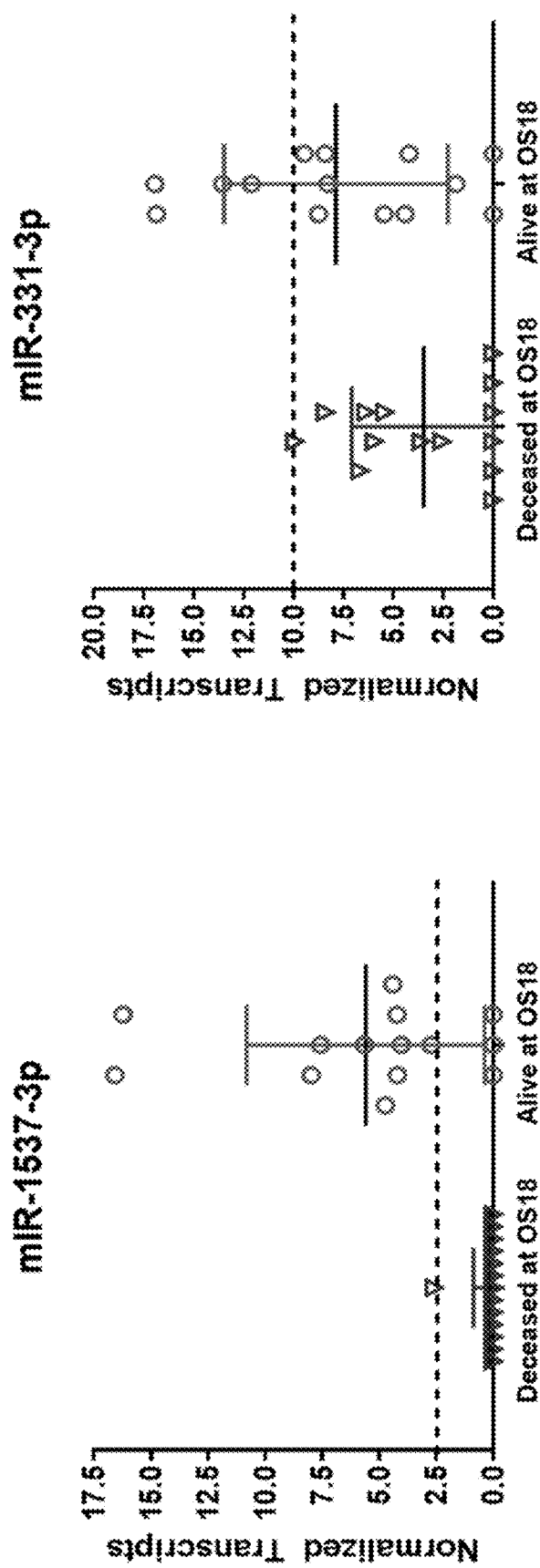
FIG. 18A and FIG. 18B show the normalized transcripts for miR-1537-3p (FIG. 18A) and miR-331-3p (FIG. 18B) for subjects deceased at 18 months post tumor resection versus subject alive at 18 months post tumor resection.
Figure 19:
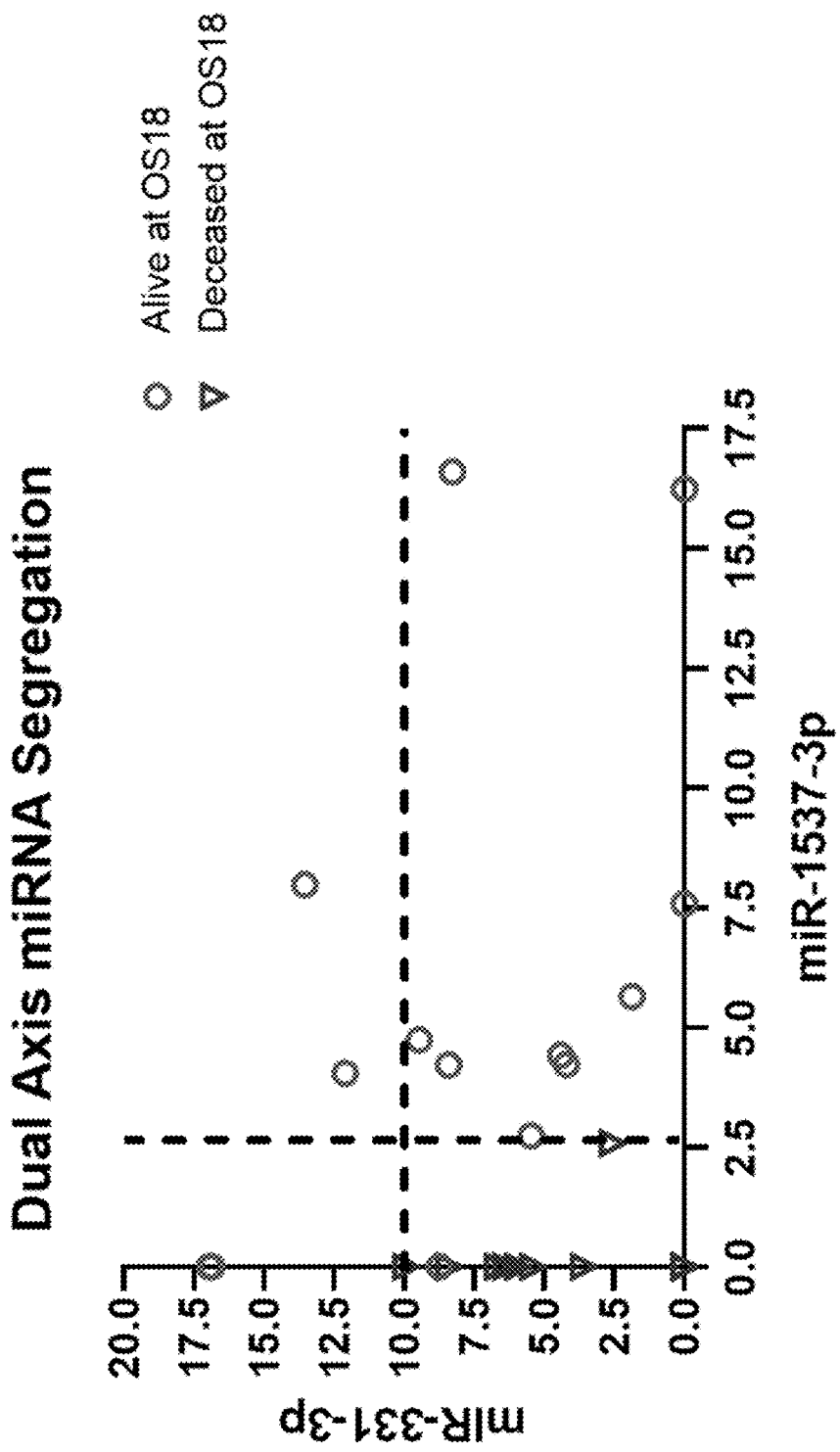
FIG. 19 shows the dual axis miRNA segregation data for miR-1537-3p (x-axis) miR-331-3p (y-axis) for subjects deceased at 18 months post tumor resection versus subject alive at 18 months post tumor resection.

Final Selection of Specific Prognostic miRNA Species for Response to INO-5401, Including Graphical Representations of Quantitative Differences and Tabular Outputs:

Final selection of miRNA species for use as a pre-treatment indicator overall survival at 18 months during treatment with INO-5401 using post-hoc data was achieved by requiring both Negative and Positive Predictive Values as well as Sensitivity and Specificity to exceed 70%. Once miRNA species meeting these requirements were identified, TMM values for the group exhibiting each clinical outcome were individually graphed along with data outputted in tabular form. These single miRNA species, when put together into a "composite" signature, result in a high prognostic value. Graphs of miR-1537-3p normalized transcripts and miR-33-3p normalized transcripts are provided in FIG. 18A and FIG. 18B, respectively. A graph of dual axis miRNA segregation for miR-331-3p and miR-1537-3p showing relative levels of each miRNA species based on survival to 18 months is provided in FIG. 19. For both miRNA species, subjects that survived at least 18 months had higher levels of a given miRNA species than those that were deceased. Table 3 provide the metrics and outcomes for the dual axis miRNA segregation for miR-331-3p and miR-1537-3p

TABLE 3

| Metric | Outcome |
|---|---|
| Accuracy | 96.43% |
| Negative Predictive Value | 93.33% |
| Positive Predictive Value | 100.00% |
| Sensitivity | 92.86% |
| Specificity | 100.00% |

Transcriptome Analysis
RNA Sequencing

RNA Sequencing was performed on tumor samples from Cohort A collected in the phase 1/2 trial described in Example 1, above, to evaluate gene expression levels. Formalin-fixed, paraffin-embedded (FFPE) tissue taken during initial resection of the primary tumor and second/third resection upon suspected progression was processed for RNA Sequencing. Briefly, one section was H&E stained and annotated by a pathologist for tumor content. H&E annotations were transferred to adjacent sections and macrodissection was performed where possible to remove surrounding non-tumor tissue. Dual isolation of nucleic acids was performed utilizing the AllPrep DNA/RNA FFPE Tissue kit (Qiagen), followed by quality control (QC) of extracted nucleic acids using Agilent Tape Station for size distribution assessment and fluorometric method for quantification. RNA Sequencing libraries were prepared using the Stranded RNA Sequencing kit (Kapa Biosystems) and followed by QC metrics. RNA Sequencing was performed on NovaSeq™ 6000 (Illumina, San Diego, CA, USA) sequencers with paired-end 2×150 bp read lengths and Illumina's proprietary reversible terminator-based method. Tumor specimens were sequenced to an average output of 100 million paired end reads (total of 200 M reads). Reads that mapped to the preferred transcript of each gene were counted to measure expression levels for genes from each tumor sample. Raw strand-specific counts per gene were generated by the STAR aligner. Counts per Million mapped reads (CPM) were calculated and globally normalized across samples using trimmed mean of M values (TMM). Transcriptome analysis was performed.

Transcriptome Analysis—Primary Tumor Samples

Figure 20:
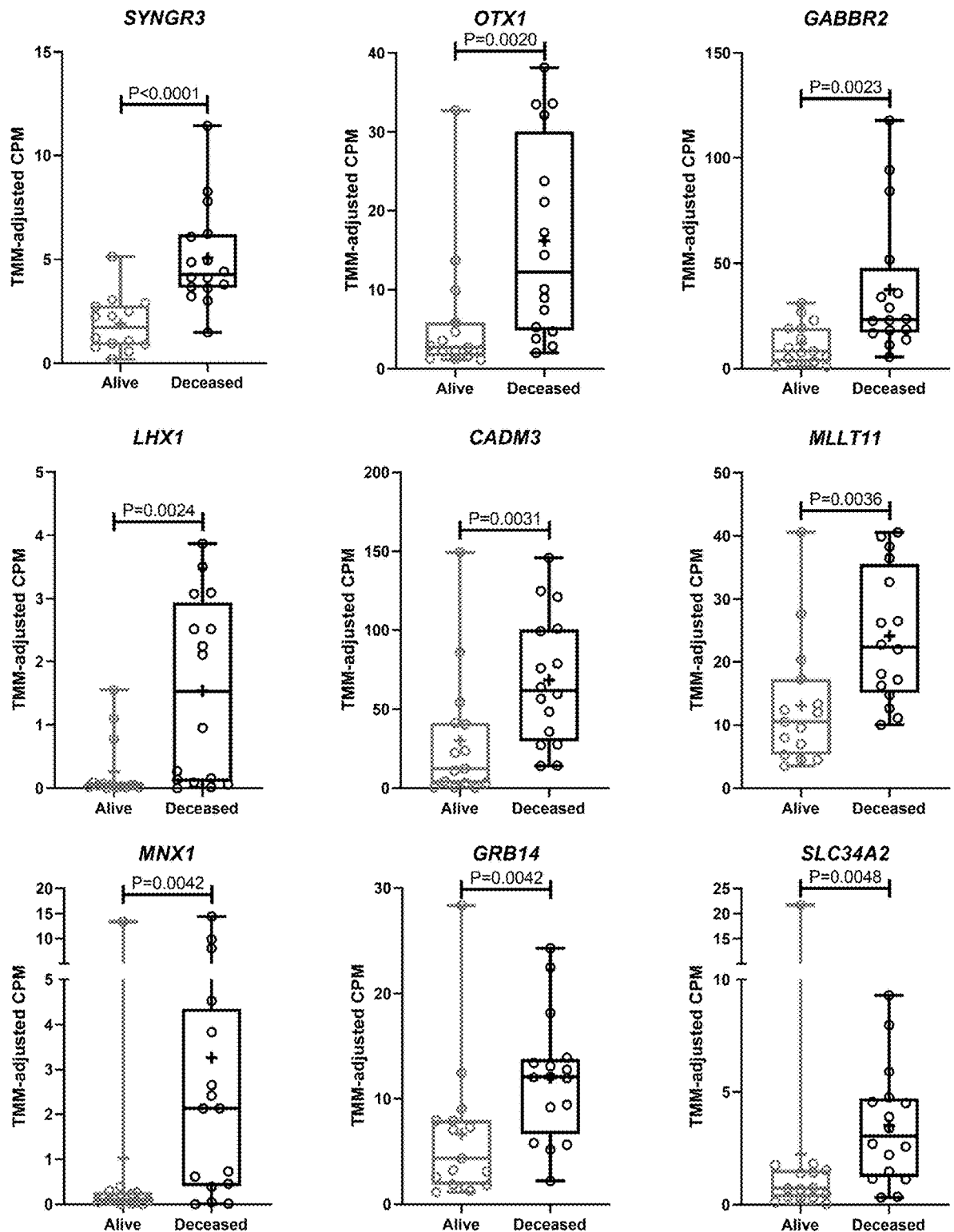
FIG. 20 provides the transcriptome analysis of primary tumors from Cohort A (MGMT Unmethylated) patients grouped according to OS18 assessment (n=31 patients) (15 alive, 16 deceased). Each subject is represented by an open circle. Box plots extend from the 25th to 75th percentile, with a horizontal line at the median, and "+" at the mean.
Figure 20:
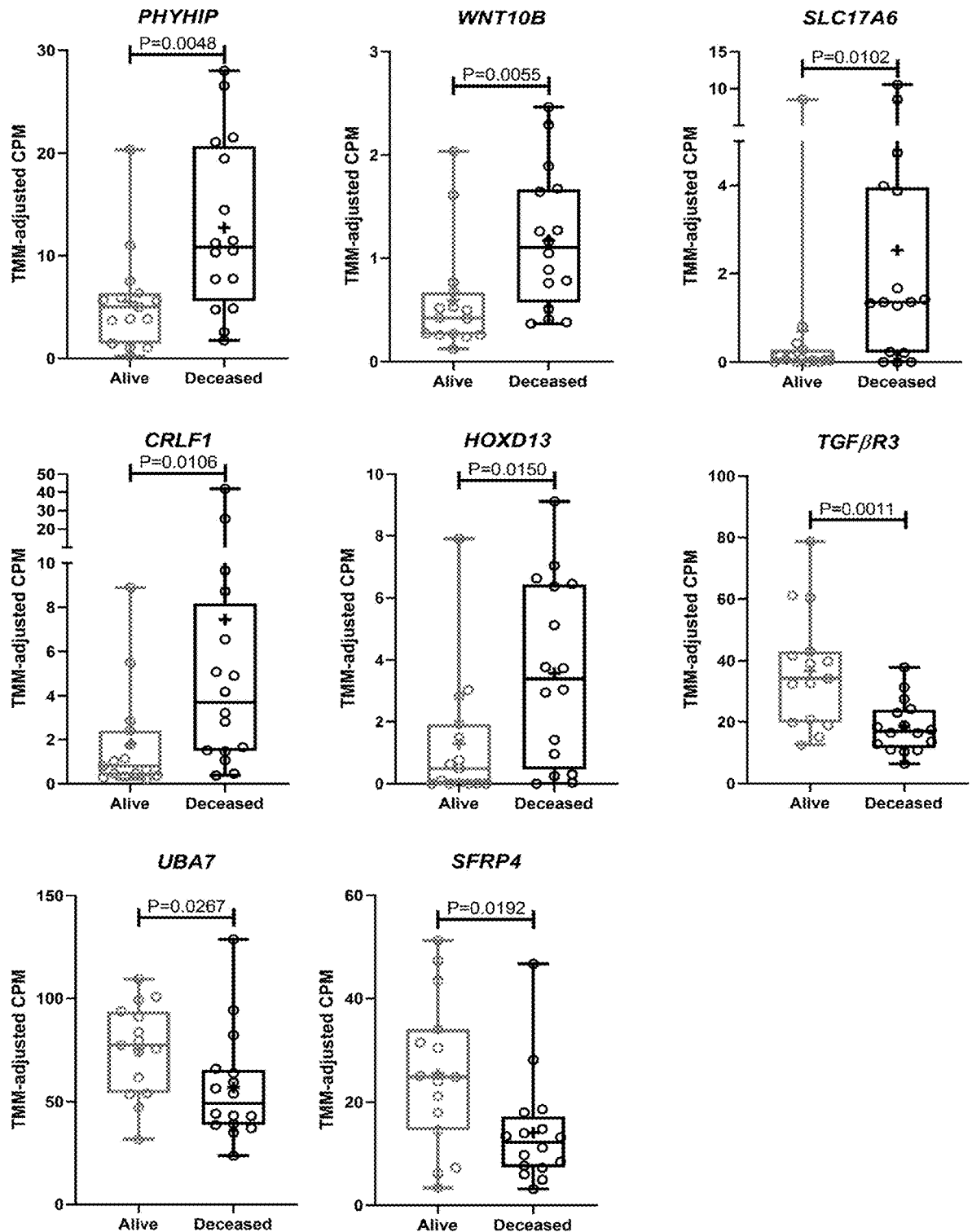

Patients in Cohort A (MGMT Unmethylated) were divided into two groups, those who were alive (n=15) or deceased (n=16) at the OS18 assessment. Gene transcripts were compared on a group basis and statistically significant differences in gene expression were assessed using the Wilcoxon rank sum (Mann-Whitney U) test. Differentially expressed genes (DEGs) were interrogated for function and relevance and a gene expression signature that may be associated with survival at OS18 in response to treatment with INO-5401 and INO-9012, in combination with cemiplimab, was identified. Patients who were alive at OS18 displayed reduced expression of SYNGR3, OTX1, GABBR2, LHX1, CADM3, MLLT11, MNX1, GRB14, SLC34A2, PHYHIP, WNT10B, SLC17A6, CRLF1 and HOXD13, and enhanced expression of TGFβR3, UBA7, SFRP4, in comparison to patients who were deceased at OS18 (FIG. 20).

Transcriptome Analysis—Paired Tumor Samples

Figure 21:
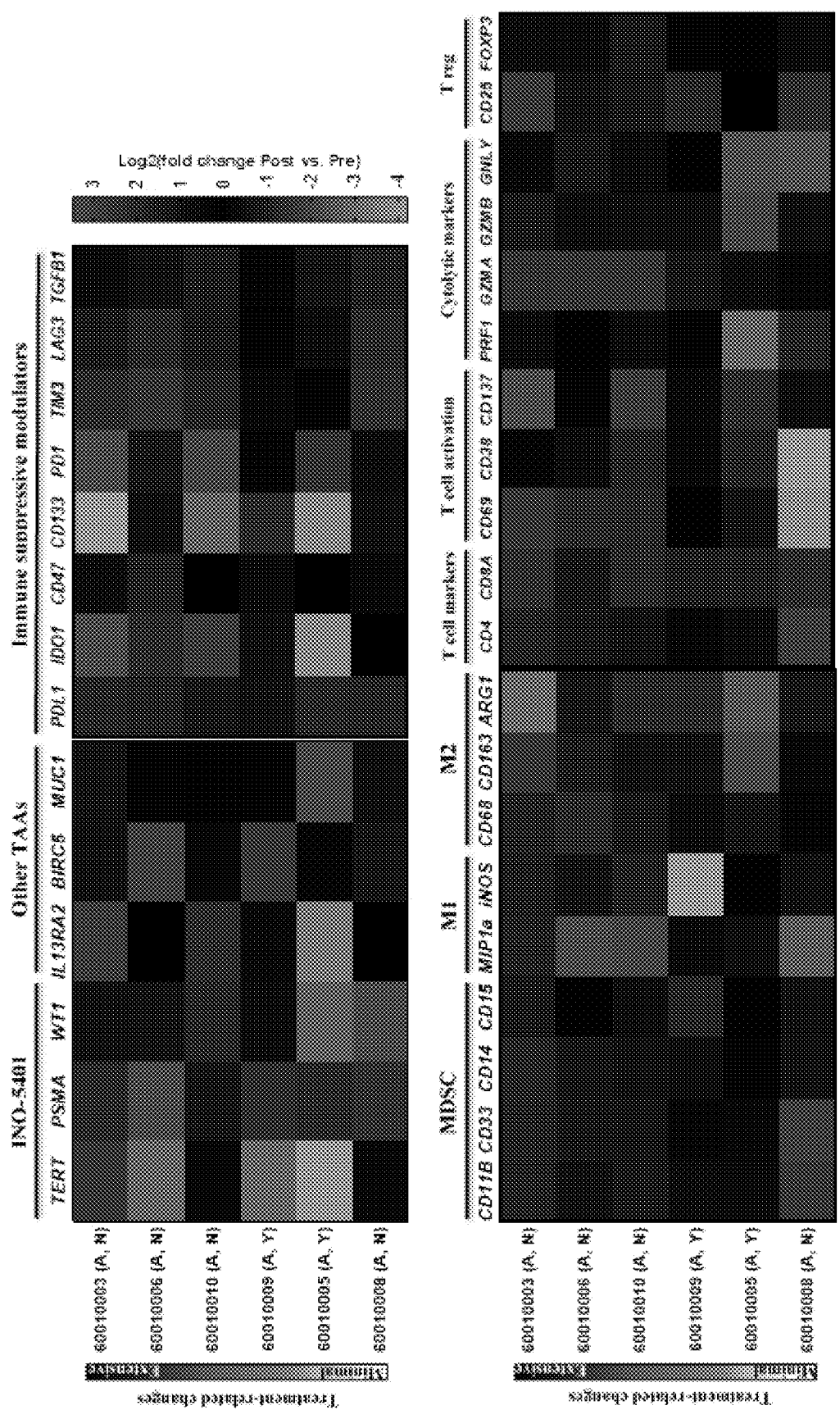
FIG. 21 shows changes in gene expression levels for tumor antigen targets and markers for immune cell modulators and subsets from six patients in Cohort A (MGMT Unmethylated) in progression (Post-) versus primary (Pre-) tumor tissue is expressed as log 2 (fold change); red indicates an increase and green indicates a decrease in gene expression levels.

Paired samples (primary and progression tissue) were analyzed from six patients in Cohort A (MGMT Unmethylated) and gene transcripts were compared on a per subject basis. Gene expression was assessed for tumor antigen targets and markers for immune cell modulators and subsets (FIG. 21).

Six patients had 'treatment-related changes' noted in pathology reports for their second/third resections. Each patient displayed altered gene expression of at least two tumor antigen targets encoded by INO-5401 in progression vs. primary tumor tissue. Extent of treatment-related changes (extensive to minimal) noted in pathology reports from second/third resections correlated with changes in expression levels of immune-related genes, especially those for T cell markers, in progression vs. primary tumor tissue: Three patients (60010003, 60010006, 60010010) displayed overall enhanced expression, one patient (60010009) displayed mildly enhanced or relatively unchanged expression, and two patients (60010005, 60010008) displayed overall reduced expression of immune cell modulators and subsets in progression vs. primary tumor tissue.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed:

1. A method of treating glioblastoma characterized by an unmethylated 06-methylguanine methyltransferase (MGMT) gene promoter in a subject having an increased pre-treatment expression level of a miR-331-3p miRNA or isomiRs thereof and a miR-1537-3p miRNA or isomiRs thereof relative to a control population of subjects, comprising:

administering to said subject:
 an anti-programmed cell death receptor 1 (PD-1) antibody;
 interleukin-12 (IL-12); and
an immunogenic composition comprising a DNA plasmid comprising a nucleic acid sequence encoding human telomerase reverse transcriptase (hTERT) antigen, a DNA plasmid comprising a nucleic acid sequence encoding Wilms Tumor-1 (WT-1) antigen, and a DNA plasmid comprising a nucleic acid sequence encoding prostate specific membrane antigen (PSMA) antigen,
 wherein the control population of subjects is a population of subjects having glioblastoma characterized by an unmethylated MGMT promoter administered IL-12; the immunogenic composition comprising a DNA plasmid comprising a nucleic acid sequence encoding hTERT antigen, a DNA plasmid comprising a nucleic acid sequence encoding WT-1 antigen, and a DNA plasmid comprising a nucleic acid sequence encoding PSMA antigen; and the anti-PD-1 antibody that is deceased at 18 months post tumor resection.

2. The method of claim 1, wherein administration of IL-12; the immunogenic composition comprising a DNA plasmid comprising a nucleic acid sequence encoding hTERT antigen, a DNA plasmid comprising a nucleic acid sequence encoding WT-1 antigen, and a DNA plasmid comprising a nucleic acid sequence encoding PSMA antigen; and the anti-PD-1 antibody results in survival at 18 months post tumor resection administration.

3. The method of claim 1, wherein hTERT, WT-1, and PSMA are encoded by the same DNA plasmid; two of hTERT, WT-1, and PSMA are encoded by the same DNA plasmid; or wherein hTERT, WT-1, and PSMA are each encoded by a different DNA plasmid.

4. The method of claim 1, wherein the anti-PD-1 antibody:
 comprises the heavy chain complementarity determining regions (HCDR1, HCDR2 and HCDR3) of a heavy chain variable region (HCVR) comprising the amino acid sequence of SEQ ID NO: 1 and three light chain complementarity determining regions (LCDR1, LCDR2 and LCDR3) of a light chain variable region (LCVR) comprising the amino acid sequence of SEQ ID NO: 2;
 comprises three HCDRs (HCDR1, HCDR2 and HCDR3) and three LCDRs (LCDR1, LCDR2 and LCDR3), wherein HCDR1 comprises the amino acid sequence of SEQ ID NO: 3, HCDR2 comprises the amino acid sequence of SEQ ID NO: 4, HCDR3 comprises the amino acid sequence of SEQ ID NO: 5, LCDR1 comprises the amino acid sequence of SEQ ID NO: 6, LCDR2 comprises the amino acid sequence of AA, and LCDR3 comprises the amino acid sequence of SEQ ID NO: 8;
 comprises a HCVR with 90% sequence identity to SEQ ID NO: 1;
 comprises a LCVR with 90% sequence identity to SEQ ID NO: 2;
 comprises a HCVR with 90% sequence identity to SEQ ID NO: 1 and a LCVR with 90% sequence identity to SEQ ID NO: 2;
 comprises a HCVR comprising the amino acid sequence of SEQ ID NO: 1 and a LCVR comprising the amino acid sequence of SEQ ID NO: 2;
 comprises a heavy chain comprising the amino acid sequence of SEQ ID NO: 9 and a light chain comprising the amino acid sequence of SEQ ID NO: 10; or
 is an IgG4 antibody.

5. The method of claim 1, wherein the anti-PD-1 antibody is administered intravenously or subcutaneously.

6. The method of claim 1, wherein 350 mg of the anti-PD-1 antibody is administered every three weeks.

7. The method of claim 1, wherein:
 the IL12 p35 subunit comprises the amino acid sequence of SEQ ID NO: 23;
 the IL12 p40 subunit comprises the amino acid sequence of SEQ ID NO: 25;
 the IL12 p35 subunit comprises the amino acid sequence of SEQ ID NO: 23 and the IL12 p40 subunit comprises the amino acid sequence of SEQ ID NO: 25;
 the IL12 p35 subunit is encoded by the nucleic acid sequence of SEQ ID NO: 22;
 the IL12 p40 subunit is encoded by the nucleic acid sequence of SEQ ID NO: 24; or
 the IL12 p35 subunit is encoded by the nucleic acid sequence of SEQ ID NO: 22 and the IL 12 p40 subunit is encoded by the nucleic acid sequence of SEQ ID NO: 24.

8. The method of claim 1, wherein:
 the hTERT comprises the amino acid sequence of SEQ ID NO: 20 or is encoded by the nucleic acid sequence of SEQ ID NO: 19;
 the WT-1 comprises the amino acid sequence of SEQ ID NO: 26 or is encoded by the nucleic acid sequence of SEQ ID NO: 27; and/or
 the PSMA comprises the amino acid sequence of SEQ ID NO: 28 or is encoded by the nucleic acid sequence of SEQ ID NO: 29.

9. The method of claim 8, wherein the method comprises administering to the subject 3 mg of the DNA plasmid encoding hTERT, 3 mg of the DNA plasmid encoding PSMA, 3 mg of the DNA plasmid encoding WT-1, and 1 mg of the plasmid encoding IL-12.

10. The method of claim 1, wherein the IL-12 and the immunogenic composition are co-administered by intramuscular injection every three weeks for four doses and then every nine weeks.

11. The method of claim 10, further comprising electroporation following each intramuscular injection.

12. The method of claim 1, further comprising administering to the subject one or more doses of radiation therapy.

13. The method of claim 12, wherein each dose of radiation therapy comprises 20-50 Gy.

14. The method of claim 13, wherein the radiation therapy is fractionated radiation therapy.

15. The method of claim 14, wherein the fractionated radiation therapy comprises 2-20 fractions.

16. The method of claim 15, wherein the fractionated radiation therapy comprises 40 Gy in 15 fractions.

17. The method of claim 16, wherein the fractionated radiotherapy is given over 21 consecutive days.

18. The method of claim 1, further comprising administering to the subject one or more doses of a chemotherapeutic agent; optionally wherein the chemotherapeutic agent is temozolomide.

19. The method of claim 18, comprising administering 75 mg/m² temozolomide to the subject daily for 21 consecutive days with the fractionated radiotherapy.

20. The method of claim 1, further comprising measuring the expression level of the miR-331-3p miRNA or isomiRs thereof and a miR-1537-3p miRNA or isomiRs thereof in a biological sample of the subject prior to said administering.

21. The method of claim 20, wherein the biological sample is taken from the subject prior to administration of the IL-12; the immunogenic composition comprising a DNA plasmid comprising a nucleic acid sequence encoding hTERT antigen, a DNA plasmid comprising a nucleic acid sequence encoding WT-1 antigen, and a DNA plasmid comprising a nucleic acid sequence encoding PSMA; and the anti-PD-1 antibody.

22. The method of claim 20, wherein the biological sample is a plasma sample.

23. The method of claim 20, wherein the measuring of the expression level of miRNA comprises RNA sequencing.

* * * * *